(12) United States Patent
Schroeppel et al.

(10) Patent No.: US 8,024,048 B2
(45) Date of Patent: Sep. 20, 2011

(54) METHOD AND DEVICE FOR TREATING CANCER WITH ELECTRICAL THERAPY IN CONJUNCTION WITH CHEMOTHERAPEUTIC AGENTS AND RADIATION THERAPY

(75) Inventors: Edward Schroeppel, Sugar Land, TX (US); Mark Kroll, Simi Valley, CA (US); Kai Kroll, Minneapolis, MN (US)

(73) Assignee: Ionix Medical Inc., Maple Grove, MN (US)

( * ) Notice: Subject to any disclaimer, the term of this patent is extended or adjusted under 35 U.S.C. 154(b) by 91 days.

(21) Appl. No.: 10/841,205

(22) Filed: May 7, 2004

(65) Prior Publication Data
US 2005/0004507 A1 Jan. 6, 2005

Related U.S. Application Data

(60) Provisional application No. 60/469,205, filed on May 8, 2003.

(51) Int. Cl.
*A61N 1/00* (2006.01)

(52) U.S. Cl. .................. 607/72; 607/3; 604/20

(58) Field of Classification Search ............... 607/3, 75, 607/72, 2, 50, 115, 116, 142, 148; 604/20, 604/27
See application file for complete search history.

(56) References Cited

U.S. PATENT DOCUMENTS

| | | | |
|---|---|---|---|
| 4,003,379 A | 1/1977 | Ellinwood, Jr. | |
| 4,026,304 A | 5/1977 | Levy | |
| 4,289,135 A | 9/1981 | Nordenstrom et al. | |
| 4,572,214 A | 2/1986 | Nordenstrom et al. | |
| 4,639,244 A * | 1/1987 | Rizk et al. | 604/19 |
| 4,679,561 A | 7/1987 | Doss | |
| 4,919,138 A | 4/1990 | Nordenstrom | |
| 4,974,595 A | 12/1990 | Nordenstrom | |
| 5,058,605 A | 10/1991 | Slovak | |
| 5,098,843 A | 3/1992 | Calvin | |
| 5,314,451 A | 5/1994 | Mulier | |
| 5,314,457 A | 5/1994 | Jetter et al. | |
| 5,458,627 A | 10/1995 | Baranowski | |
| 5,501,662 A | 3/1996 | Hofmann | |
| 5,507,724 A * | 4/1996 | Hofmann et al. | 604/501 |
| 5,536,267 A * | 7/1996 | Edwards et al. | 606/41 |
| 5,584,872 A | 12/1996 | LaFontaine et al. | |
| 5,611,350 A | 3/1997 | John | |
| 5,630,426 A | 5/1997 | Eggers et al. | |

(Continued)

FOREIGN PATENT DOCUMENTS

EP 1080731 3/2001

(Continued)

OTHER PUBLICATIONS

U.S. Appl. No. 10/792,256, filed Mar. 2, 2004, Schroeppel.

(Continued)

*Primary Examiner* — Carl H Layno
*Assistant Examiner* — Pamela M Bays
(74) *Attorney, Agent, or Firm* — Patterson Thuente Christensen Pedersen, P.A.

(57) ABSTRACT

A method for the electrical treatment of malignant tumors and neoplasms by applying a voltage to affected tissue. Devices and various adaptations therein are described for use in electrical therapy. Additionally, various chemotherapeutic agent and radiation therapies are described which may be advantageously used in conjunction with electrical therapy to ameliorate cancer.

38 Claims, 51 Drawing Sheets

U.S. PATENT DOCUMENTS

| | | | |
|---|---|---|---|
| 5,674,267 | A | 10/1997 | Mir et al. |
| 5,701,895 | A | 12/1997 | Prutchi et al. |
| 5,807,306 | A * | 9/1998 | Shapland et al. ............... 604/21 |
| 5,820,548 | A | 10/1998 | Sieben et al. |
| 5,869,326 | A * | 2/1999 | Hofmann .................... 435/285.2 |
| 5,919,187 | A | 7/1999 | Guglielmi et al. |
| 5,983,131 | A * | 11/1999 | Weaver et al. .................. 604/20 |
| 5,985,305 | A | 11/1999 | Peery et al. |
| 5,993,434 | A * | 11/1999 | Dev et al. ....................... 604/501 |
| 6,009,345 | A * | 12/1999 | Hofmann ........................ 604/20 |
| 6,021,347 | A | 2/2000 | Herbst |
| 6,049,733 | A * | 4/2000 | Phipps et al. ................... 604/20 |
| 6,051,017 | A | 4/2000 | Loeb et al. |
| 6,169,924 | B1 | 1/2001 | Meloy et al. |
| 6,171,787 | B1 | 1/2001 | Wiley |
| 6,269,270 | B1 | 7/2001 | Boveja |
| 6,278,895 | B1 * | 8/2001 | Bernard .......................... 604/20 |
| 6,366,808 | B1 | 4/2002 | Schroeppel |
| 6,391,026 | B1 | 5/2002 | Hung et al. |
| 6,591,133 | B1 | 7/2003 | Joshi |
| 6,599,274 | B1 | 7/2003 | Kucharczyk et al. |
| 6,600,953 | B2 | 7/2003 | Flesler et al. |
| 6,607,528 | B1 | 8/2003 | Quick et al. |
| 6,638,273 | B1 | 10/2003 | Farley et al. |
| 6,708,066 | B2 | 3/2004 | Herbst et al. |
| 6,713,291 | B2 | 3/2004 | King |
| 6,733,485 | B1 * | 5/2004 | Whitehurst et al. .......... 604/500 |
| 6,738,663 | B2 | 5/2004 | Schroeppel |
| 6,901,296 | B1 | 5/2005 | Whitehurst et al. |
| 2001/0021868 | A1 | 9/2001 | Herbst et al. |
| 2002/0026188 | A1 | 2/2002 | Balbierz et al. |
| 2002/0115957 | A1 * | 8/2002 | Sun et al. ........................ 604/20 |
| 2003/0191504 | A1 | 10/2003 | Meadows et al. |
| 2004/0010290 | A1 | 1/2004 | Schroeppel |
| 2004/0030334 | A1 | 2/2004 | Quick et al. |
| 2004/0172089 | A1 | 9/2004 | Whitehurst et al. |
| 2004/0254618 | A1 | 12/2004 | Schroeppel et al. |
| 2005/0222623 | A1 | 10/2005 | Schroeppel et al. |
| 2005/0222646 | A1 | 10/2005 | Schroeppel et al. |

FOREIGN PATENT DOCUMENTS

| | | |
|---|---|---|
| WO | 9847562 | 10/1998 |
| WO | 0152931 | 7/2001 |
| WO | 0162336 | 8/2001 |
| WO | WO-0162336 | 8/2001 |
| WO | 02098501 | 12/2002 |

OTHER PUBLICATIONS

U.S. Appl. No. 10/819,641, filed Apr. 6, 2004, Schroeppel.
U.S. Appl. No. 10/881,375, filed Jun. 29, 2004, Schroeppel.
www.genetronics.com, retrieved Jul. 29, 2003.
Electro-Cancer Treatment, http://www.st-georg.com/ect.html, retrieved Oct. 25, 1999.
J. Belehradek, Jr., S. Orlowski, L.H. Ramirez, G. Pron, B. Poddevin, L.M. Mir. Electropermeabilization of Cells in Tissues Assessed by the Qualitative and Quantitative Electroloading of Bleomycin, Biochimica et Biophysica Acta 1190 (1994): 155-163.
M. Belehradek, C. Domenge, B. Luboinski, S. Orlowski, J. Belehradek, Jr., L.M. Mir. Abstract of Electrochemotherapy, a New Antitumor Treatment. First Clinical Phase I-II Trial, Cancer Dec. 15, 1993;72(12):3694-700.
Berendson and D. Simonsson. Electrochemical Aspects of Treatment of Tissue with Direct Current, European Journal of Surgery 1994; Suppl 574: 111-115.
Brandisky, I. Daskalov. Abstract of Electrical Field and Current Distributions in Electrochemotherapy, Bioelectrochemistry and Bioenergetics Feb. 1999;48(1):201-8.
H. Buchwald and T.D. Rohde. Implantable Pumps; Recent Progress and Anticipated Future Advances, ASAIO Journal 1992, p. 772-778.
M. Cemazar, G. Sersa and D. Miklavcic. Electrochemotherapy with Cisplatin in the Treatment of Tumor Cells Resistant to Cisplatin, Anticancer Research 18: 4463-4466 (1998).
B. Chen, Z. Xie, F. Zhu. Experimental Study on Electrochemical Treatment of Cancer in Mice, European Journal of Surgery, 1994; Suppl 574: 75-77.
C.K. Chou, J.A. McDougall, C. Ahn, N. Vora. Abstract of Electrochemical Treatment of Mouse and Rat Fibrosarcomas with Direct Current. Bioelectromagnetics 1997; 18(1):14-24.
B. Damascelli, G. Patelli, L.R. Frigerio, R. Lanocita, G. Di Tolla, A. Marchiano, C. Spreafico, F. Garbagnati, M.G. Bonalumi, L. Monfardini, V. Ticha, A. Prino. First Clinical Experience with a High-Capacity Implantable Infusion Pump for Continuous Intravenous Chemotherapy, CardioVascular and Interventional Radiology (1999) 22:37-43.
S. L. David, D.R. Absolom, C.R. Smith, J. Gams, and M.A. Herbert. Effect of Low Level Direct Current on In Vivo Tumor Growth in Hamsters, Cancer Research 45, 5625-5631, Nov. 1985.
R.A. Gatenby. Abstract of Mathmatical Models of Tumour Invasion Mediated by Transformation-Induced Alteration of Microenvironment pH, Symposium 240; The Tumour Microenvironment: Causes and Consequences of Hypoxia and Acidity, p. 2-3, held at the Novartis Foundation, London, 240 10-12, Oct. 2000.
L.F. Glass, N. A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.
H.Y. Gong, G.Z. Liu. Effect of Electrochemical Therapy on Immune Functions of Normal and Tumour-Bearing Mice, European Journal of Surgery, Suppl 1994; (574): 73-74.
S.A. Grossman, P.S. Staats. Abstract of Current management of pain in patients with cancer. Oncology (Huntingt) Mar. 1994; 8(3):93-107.
M.B. Habal, M.D., M.K. Schauble, M.D. Clinical Device Note: An Implantable DC Power Unit for Experimental Tumor Growth in Hamsters, Journal of the Association for the Advancement of Medical Instrumentation, vol. 7, No. 5, Nov.-Dec. 1973, p. 305-306.
M.B. Habal. Effect of Applied DC Currents on Experimental Tumor Growth in Rats, Journal of Biomedical Materials Research, vol. 14, 789-801 (1980).
M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile. Anesthesiology Nov. 1999;91(5): 1232-8.
C. Hauton, M. Charbonnier, L. Cara and J.P. Salles. A New Type of Liposome for Electrochemical Treatment of Cancer: The Lipogelosomes, European Journal of Surgery 1994; Suppl 574: 117-119.
K.T. Heruth. Medtronic SynchroMed Drug Administration System. Ann NY Acad Sci 1988: 531: 72-75.
G.A. Hofmann, S.B. Dev, S. Dimmer and G.S. Nanda. Electroporation Therapy: A New Approach for the Treatment of Head and Neck Cancer, IEEE Transactions on Biomedical Engineering, vol. 46, No. 6, Jun. 1999.
G.A. Hofmann S.B. Dev, G.S. Nanda and D. Rabussay. Electroporation Therapy of Solid Tumors, Critical Reviews in Therapeutic Drug Carrier Systems, 16(6):523-569 (1999).
C.E. Humphrey, E.H. Seal. Biophysical Approach Toward Tumor Regression in Mice, Science, vol. 130, 1959.
D.L. Kirsch, F.N. Lerner. Electromedicine: The Other Side of Physiology. In: "Innovations in Pain Management: A Practical Guide for Clinicians", selections of Chapter 23, 1995, GR Press, Winter Park, FL.
M. Kraus and B. Wolf. Implications of Acidic Tumor Microenvironment for Neoplastice Growth and Cancer Treatment: A Computer Analysis, Tumor Biology 1996; 17: 133-154.
M. Kraus and B. Wolf. Physicochemical Microenvironment as Key Regulator for Tumor Microevolution, Invasion and Immune Response: Targets for Endocytotechnological Approaches in Cancer Treatment, Endocytobiosis & Cell Research, 12, 133-156 (1998).
Y.H. Lao, T.G. Ge, X.L. Zheng, J.Z. Zhang, Y.W. Hua, S.M. Mao and X. Feng. Electrochemical Therapy for Intermediate and Advanced Liver Cancer: A Report of 50 Cases, European Journal of Surgery 1994; Suppl 574: 51-53.
K.H. Li, Y.L. Xin, Y.N. Gu, B.L. Xu, D.J. Fan and B.F. Ni. Effects of Direct Current on Dog Liver: Possible Mechanisms for tumor Electrochemical Treatment, Bioelectromagnetics 18:2-7 (1997).
X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000;45(3): 509-514.

D. Liu, Y.L. Xin, B. Ge, F. Zhao, H.C. Zhso. Experimental Studies on Electrolytic Dosage of ECT for Dog's Oesophageal Injury and Clinical Effects of ECT for Oesophageal Anastomotic Opening Stenosis and Oesophageal Carcinoma, European Journal of Surgery Suppl 1994; (574):71-72.

Y. Matsushima, E. Takahashi, K. Hagiwara, C. Konaka, H. Miura, H. Kato and Y. Koshiishi. Clinical and Experimental Studies of Anti-Tumoural Effects of Electrochemical Therapy (ECT) Alone or in Combination with Chemotherapy, European Journal of Surgery 1994; Suppl 574: 59-67.

Miklavcic, D. An, J. Belehradek, Jr., L.M. Mir. Abstract of Host's Immune Response in Electrotherapy of Murine tumors by Direct Current, European Cytokine Network Sep. 1997; 8(3):275-9.

L.M. Mir, S. Orlowski, J. Belehradek Jr., and C. Paoletti. Electrochemotherapy Potentiation of Antitumour Effect of Bleomycin by Local Electric Pulses, European Journal of Cancer, vol. 27, No. 1, pp. 68-72, 1991.

D.M. Morris, M.D., A.A. Marino, Ph. D., and E. Gonzalez, M.D. Electrochemical Modification of Tumor Growth in Mice, Journal of Surgical Research 53, 306-309 (1992).

E. Nilsson. Modelling of the Electrochemical Treatment of Tumours, Dissertation, Department of Chemical Engineering and Technology, Applied Electrochemistry, Royal Institute of Technology, Stockholm 2000.

T. Nishi, S.B. Dev., K. Yoshizato, J. Kuratsu, Y. Ushio. Abstract of Treatment of Cancer Using Pulsed Electric Field in Combination with Chemotherapeutic Agents or Genes, Human Cell Mar. 1997; 10(1):81-6.

B. Nordenstrom. Preliminary Clinical Trials of Electrophoretic Ionization in the Treatment of Malignant Tumors, IRCS Medical Science: Biomedical Technology; Cancer; Cell and Membrane Biology; Clinical Medicine; Respiratory System; Pathology, 6, 537 (1978).

B. Nordenstrom. Biologically Closed Electric Circuits; Clinical, Experimental and Theoretical Evidence for an Additional Circulatory Systems, XVI., Tissue transformations over BCEC in cancer of the breast, p. 203-268; XVII., Application of the principle of BCEC for treatment of cancer, p. 269-317. 1983, Karolinska Institutet, Stockholm, Sweden, Nordic Medical Publications.

B. Nordenstrom, M.D. Biologically Closed Electric Circuits: Activation of Vascular Interstitial Closed Electric Circuits for Treatment of Inoperable Cancers, Journal of Bioelectricity, 3 (1&2), 137-153 (1984).

B.E.W. Nordenstrom, M.D. Electrochemical Treatment of Cancer. I: Variable Response. American Journal of Clinical Oncology (CCT) 12(6); 530-536, 1989.

B.E.W. Nordenstrom, M.D., S. Eksborg, Ph. D., and H. Beving, Ph. D. Electrochemical Treatment of Cancer. II: Effect of Electrophoretic Influence on Adriamycin, American Journal of Clinical Oncology (CCT) 13(1): 75-88, 1990.

B.E.W. Nordenstrom, M.D. Survey of Mechanisms in Electrochemical Treatment (ECT) of Cancer, European Journal of Surgery 1994; Suppl 574: 93-109.

G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.

M. Okino and H. Mohri. Effects of a High-Voltage Electrical Impulse and an Anticancer Drug on In Vivo Growing Tumors, Japan Journal of Cancer Research, (Gann) 78, 1319-1321; Dec. 1987.

S. Orlowski, J. Belehradek, Jr., C. Paoletti and L.M. Mir. Transient Electropermeablization of Cells in Culture; Increase of Cytotoxicity of Anticancer Drugs, Biochemical Pharmacology, vol. 37, No. 24, pp. 4727-4733, 1988.

W.R. Panje, M.P. Hier, G.R. Garman, E. Harrell, A. Goldman, I. Bloch. Abstract of Electroporation therapy of Head and Neck Cancer, Annals of Otology, Rhinology and Laryngology Sep. 1988;107 (9 Pt 1): 779-85.

A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574: 45-49.

K.H. Quan. Analysis of the Clinical Effectiveness of 144 Cases of Soft Tissue and Superficial Malignant Tumours Treated with Electrochemical Therapy, European Journal of Surgery 1994; Suppl 574: 37-40.

N. Raghunand. pH and Chemotherapy, Symposium 240: Abstract of the Tumour Microenvironment: Causes and Consequences of Hypoxia and Acidity, p. 5-6, held at the Novartis Foundation, London, Oct. 10-12, 2000.

L.H. Ramirez, S. Orlowski, D. An, G. Bindoula, R. Dzodic, P. Ardouin, C. Bognel, J. Belehradek Jr., J-N Munck, and L.M. Mir. Electrochemotherapy on Liver Tumours in Rabbits, British Journal of Cancer (1998) 77(12). 2104-2111.

V.V. Ranade, Ph. D. Drug Delivery Systems 4. Implants in Drug Delivery, Journal of Clinical Pharmacology 1990;30;871-889.

A. Reis, T. Henninger. Zerstorung maligner Wachstumsenergie durch anodische Oxydation. Klin Wochenschrift 1951; __:39.

L. Samuelsson, J. Harnek, S.B. Ewers and L. Jonsson. Electrochemical and Megavolt Treatment of Rat Tumours, European Journal of Surgery 1994; Suppl 574: 69-70.

M.K. Schauble, M.B. Habal. Electropotentials of Tumor Tissues. Journal of Surgical Research 9: 9, 1969.

M.K. Schauble, M.B. Habal, H. D. Gullick. Inhibition of Experimental Tumor Growth in Hamsters by Small Direct Currents, Archives of Pathology and Laboratory Medicine vol. 101, p. 294, Jun. 1977.

D.C. Schechter. Flashbacks: Containment of Tumors Through Electricity, Pacing and Clinical Electrophysiology, vol. 2, Jan.-Feb. 1979.

K. Seguchi, S. Kawauchi, Y. Morimoto, T. Arai, H. Asanuma, M. Hayakawa, M. Kikuchi. Abstract of Critical Parameters in the Cytotoxicity of Photodynamic Therapy Using a Pulsed Laser. Lasers Med Sci 2002;17(4):265-71.

D. Semrov, D. Miklavcic. Calculation of the Electrical Parameters in Electrochemotherapy of Solid Tumours in Mice, Computers in Biology and Medicine 28 (1998) 439-448.

G. Sersa, M. Cemazar, D. Miklavcic and D. J. Chaplin. Tumor Blood Flow Modifying Effect of Electrochemotherapy with Bleomycin, Anticancer Research 19: 4017-4022 (1999).

G. Sersa, Ph. D., S. Kranjc, B. Sc., and M. Cemazar, Ph. D. Improvement of Combined Modality Therapy with Cisplatin and Radiation Using Electroporation of Tumors, International Journal of Radiation-Oncology- Biology and Physics., vol. 46, No. 4, pp. 1037-1041, 2000.

B.N. Singh and C. Dwivedi. Antitumor Drug Delivery by Tissue Electroporation, Anti-Cancer Drugs 1999, 10, pp. 139-146.

Y. Song, C. Li, Y. Li, Q. Song, B. Chang, L. Song, C. Liu and T. Wang. Electrochemical Therapy in the Treatment of Malignant Tumours on the Body Surface, European Journal of Surgery 1994; Suppl 574: 41-43.

L.C. Song, C.Y. Liu, B.P. Zhang, T. Wang, Y.Q. Song and Y.W. Li. Electrochemical Therapy (ECT) for Thyroid Adenoma During Acupuncture Anaesthesia: Analysis of 46 Patients, European Journal of Surgery 1994; Suppl 574:79-81.

S. Srinivasan, G.L. Gahen Jr., G.E. Stoner. Electrochemistry in the Biomedical Sciences. In: Bloom H, Gumann F (eds): Electrochemistry The Last Thirty and The Next Thirty Years. New York: Plenum Press, 1977.

T.V. Taylor, P. Engler, B.R. Pullan and S. Holt. Ablation of Neoplasia by Direct Current, British Journal of Cancer (1994), 70, 342-345.

A. Turler, H. Schaeer, N. Schaefer, D. Maintz, M. Wagner, J.C. Qiao and A.H. Hoelscher. Local Treatment of Hepatic Metastases with Low-Level Direct Electric Current: Experimental Results, Scandinavian Journal of Gastroenterology Mar. 2000;35(3):322-328.

A.L. Vandenbogaerde, E.M. Delaey, A.M. Vantieghem, B.E. Himpens, W.J. Merlevede P.A. de Witte. Abstract of Cytotoxicity and Antiproliferative Effect of Hypericin and Derivatives After Photosensitization. Photochem Photobiol Jan. 1998;67(1):119-25.

P. Vaupel, D.K. Kelleher, M. Hockel. Abstract of Oxygen Status of Malignant Tumors: Pathogenesis of Hypoxia and Significance for Tumor Therapy. Semin Oncol Apr. 2001;28(2 Suppl 8):29-35.

L. Vodovnik, D. Miklavcic, G. Sersa. Modified Cell Proliferation Due to Electrical Currents, Medical and Biological Engineering and Computing, 1992, 30, CE21-CE28.

N. J. Vogelzang, M. Ruane, and T.R. DeMeester. Phase I Trial of an Implanted Battery-Powered, Programmable Drug Delivery System for Continuous Doxorubicin Administration, Journal of Clinical Oncology, vol. 3, No. 3 Mar. 1985.

H. von Euler. Electrochemical Treatment of Tumours, Doctoral Thesis, Uppsala 2002, Swedish University of Agricultural Sciences.

H.L. Wang. Electrochemical Therapy of 74 Cases of Liver Cancer, European Journal of Surgery 1994; Suppl. 574: 55-57.

J.C. Weaver. Electroporation: A General Phenomenon for Manipulating Cells and Tissues. J Cell Biochem 1993; 51 No. 4: 426-435.

B.D. Wigness, F.D. Dorman, H.J. Robinson, E.A. Arendt, T.R. Oegema Jr., T.D. Rohde, and H. Buchwald. Catheter with an Anchoring Tip for Chronic Joint Capsule Perfusion, ASAIO Trans. Jul.-Sep. 1991; 37(3): M290-2.

M. Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.

B. Wolf, M. Kraus and U. Sieben. Potential of Microsensor-Based Feedback Bioactuators for Biophysical Cancer Treatment, Biosensors & Bioelectronics vol. 12, No. 4, pp. 301-309, 1997.

B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.

Y.L. Xin, D. Liu. Electrostatic Therapy (EST) of Lung Cancer and Pulmonary Metastasis: Report of 15 Cases, European Journal of Surgery 1994; Suppl 574: 91-92.

Y.L. Xin. Organisation and Spread of Electrochemical Therapy (ECT) in China, Honorary Lecture. European Journal of Surgery 1994; Suppl 577: 25-30.

Y.L. Xin, F.Z. Xue, B.S. Ge, F.R. Zhao, B. Shi and W. Zhang. Electrochemical Treatment of Lung Cancer, Bioelectromagnetics 18:8-13 (1997).

Y.L. Xin, F.Z. Xue, F.G. Zhao. Effectiveness of Electrochemical Therapy in the Treatment of Lung Cancers of Middle and Late Stage, Chinese Medical Journal 1997; 110(5): 379-383.

Y. Yen, J.R. Li, B.S. Zhou, F. Rojas, J. Yu and C.K. Chou. Electrochemical Treatment of Human KB Cells In Vitro, Bioelectromagnetics 20:34-41 (1999).

M. Yokoyama, T. Itaoka, H. Nakajima, T. Ikeda, T. Ishikura, S. Nitta. Abstract of the Use of Direct Current in the Local Destruction of Cancer Tissues, Gan to Kagaku Tyoho Apr. 1989:16(4 Pt 2-2):1412-1417.

PCT/US03/14104. International Search Report. Nov. 18, 2004.

PCT International Preliminary Report on Patentability, PCT/US2005/011430, date mailed Oct. 19, 2006.

Office Action from U.S. Appl. No. 10/434,400 dated Jul. 12, 2007.

Examiner Interview Summary PTOL-413 from U.S. Appl. No. 10/434,400 dated Jul. 13, 2006.

Office Action from U.S. Appl. No. 10/434,400 dated Feb. 14, 2006.

Notice of Allowance from U.S. Appl. No. 09/524,405 dated Sep. 26, 2001.

Office Action from U.S. Appl. No. 09/524,405 dated May 21, 2001.

Notice of Allowance from U.S. Appl. No. 09/974,474 dated Dec. 22, 2003.

Office Action from U.S. Appl. No. 09/974,474 dated Jul. 11, 2003.

International Search Report, PCT/US2005/011430.

Office Action from U.S. Appl. No. 10/881,375 dated Apr. 11, 2007.

Office Action from U.S. Appl. No. 10/881,375 dated Sep. 13, 2006.

Office Action from U.S. Appl. No. 10/792,256 dated Jun. 25, 2007.

Office Action from U.S. Appl. No. 09/974,474 dated Apr. 29, 2003.

Office Action from U.S. Appl. No. 10/819,641 dated Apr. 13, 2007.

Office Action from U.S. Appl. No. 10/819,641 dated Nov. 3, 2006.

Office Action from U.S. Appl. No. 10/819,641 dated Aug. 29, 2006.

Office Action from U.S. Appl. No. 10/434,400 dated Dec. 10, 2007.

Schroeppel et al., Office Action for U.S. Appl. No. 10/881,375 mailed Apr. 16, 2008.

Schroeppel et al., Notice of Allowance for U.S. Appl. No. 10/434,400 dated Apr. 3, 2008.

Schroeppel et al., Office Action from U.S. Appl. No. 10/792,256 dated Mar. 25, 2008.

Schroeppel et al., European Search Report from EP05733003 mailed Apr. 11, 2008 (corresponds to U.S. Appl. No. 10/819,641).

Office Action from U.S. Appl. No. 10/881,375, mailed Apr. 16, 2008.

Notice of Allowance from U.S. Appl. No. 10/434,400, dated Apr. 3, 2008.

Office Action from U.S. Appl. No. 10/792,256, dated Mar. 25, 2008.

European Search Report from EP05733003, mailed Apr. 11, 2008.

European Patent Office, Office Action for 05 733003.7, mailed Aug. 13, 2008.

Final Office Action from U.S. Appl. No. 10/881,375, mailed Oct. 31, 2008.

Office Action from U.S. Appl. No. 10/881,375, mailed Jul. 2, 2008.

Office Action from U.S. Appl. No. 10/819,641, mailed Aug. 15, 2008.

Non-Final Office Action and Examiner Interview from U.S. Appl. No. 10/819,641, mailed Jan. 12, 2009.

Non Final Office Action from U.S. Appl. No. 10/792,256 mailed Apr. 30, 2009.

Non Final Office Action from U.S. Appl. No. 10/881,375 mailed Jun. 9, 2009.

European Examination Report for Application No. EP05733003.7 issued Apr. 21, 2009.

Final Office Action from U.S. Appl. No. 10/819,641 mailed Jul. 13, 2009.

European Search Report from the European Patent Office for Application No. 037997616 dated Feb. 2, 2010.

Notice of Allowance from U.S. Appl. No. 10/792,256 mailed Feb. 12, 2010.

* cited by examiner

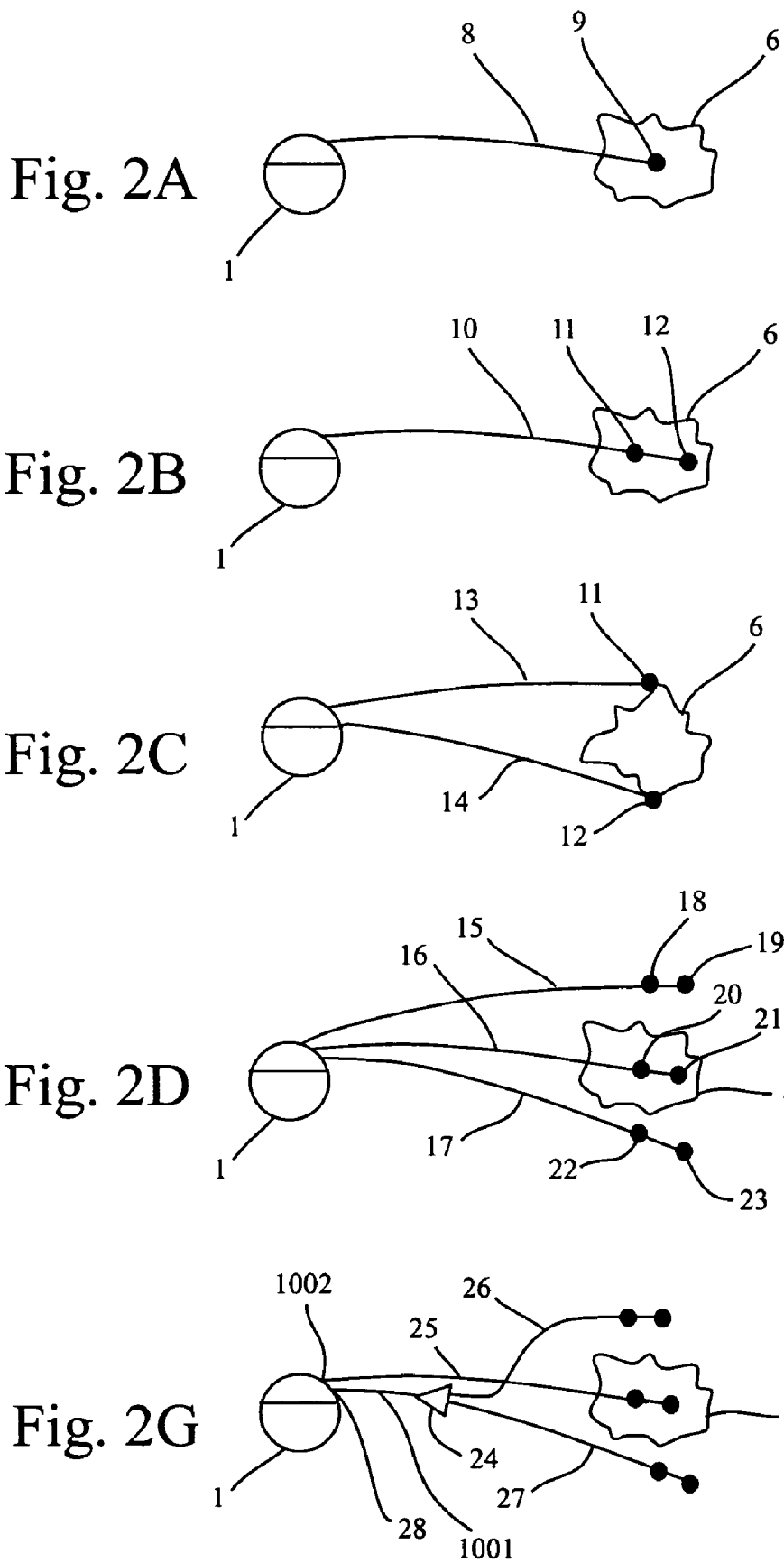

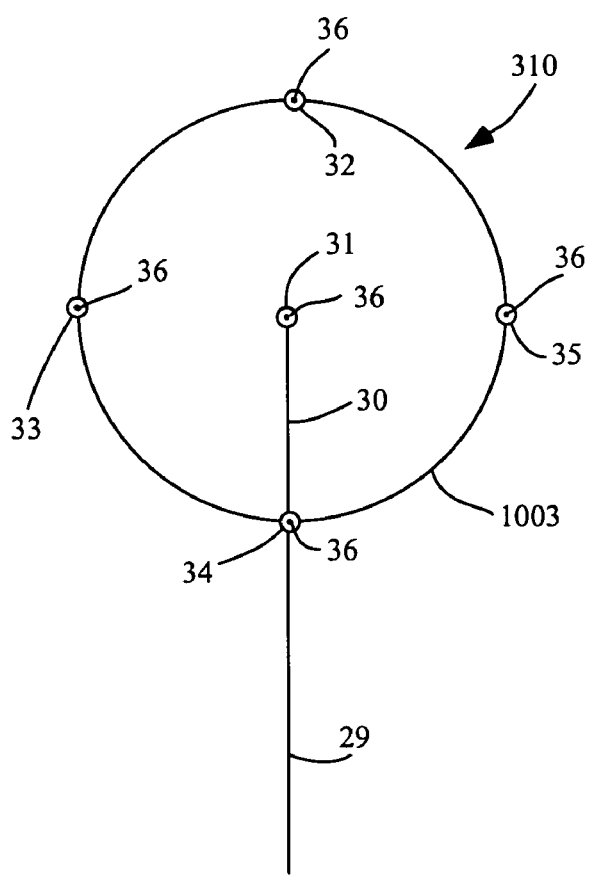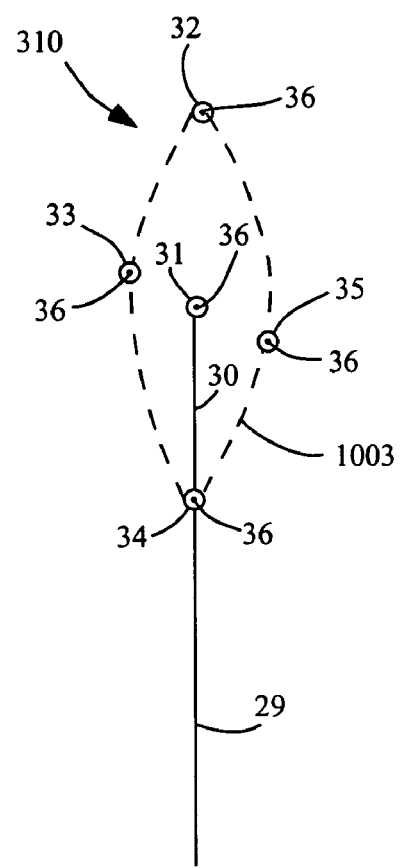
Fig. 3B                     Fig. 3C

Programmed Parameters

| Mode | Amplitude | Repetition | Duration | A polarity | B polarity | Ref polarity |
|---|---|---|---|---|---|---|
| Current | 10 mA | 1 | 30 min | + | - | 0 |
| Current | 100 µA | 1 | 22 hr | + | + | - |
| Voltage | 5V | 1 | 60 min | - | - | + |
| Voltage | 3V | 1 | 30 min | + | + | - |
| Pulses | 800V | 100 | 100 µs | | | 0 |

Measured Data

| Current | Voltage | Impedance | Time | pH | Temp | Charge Del. |
|---|---|---|---|---|---|---|
| 103 µA | 2.1V | 20.4 kΩ | 17.35 hr | 4.9 | 38.3°C | 6.43 Coulomb |

Fig. 49

METHOD AND DEVICE FOR TREATING CANCER WITH ELECTRICAL THERAPY IN CONJUNCTION WITH CHEMOTHERAPEUTIC AGENTS AND RADIATION THERAPY

CROSS REFERENCE TO RELATED APPLICATIONS

This application claims priority under 35 U.S.C. §119(e) to U.S. Provisional Patent Application Ser. No. 60/469,205 of Schroeppel et al. filed May 8, 2003, incorporated herein by reference.

RELATED APPLICATIONS

This application is related to U.S. Ser. No. 09/974,474 for "IMPLANTABLE DEVICE AND METHOD FOR THE ELECTRICAL TREATMENT OF CANCER" filed Dec. 14, 2001, which is a non-provisional application of provisional U.S. Ser. No. 60/238,609 for "IMPLANTABLE THERAPEUTIC DEVICE" filed Feb. 13, 2001 and also is a continuation-in-part (CIP) of U.S. Ser. No. 09/524,405 for "IMPLANTABLE DEVICE AND METHOD FOR THE ELECTRICAL TREATMENT OF CANCER" filed Mar. 13, 2000, now U.S. Pat. No. 6,366,808.

This application is also related to U.S. Ser. Nos. 60/238,612 for "ELECTROPHORETIC DRUG INFUSION DEVICE" filed Oct. 10, 2000; 60/255,184 for "METHOD FOR ELIMINATING POSSIBLE CORROSION OF ELECTRODES IN ELECTROCHEMICAL THERAPY AND ELECTROCHEMOTHERAPY" filed Dec. 12, 2000; 60/128,505 for "IMPLANTABLE DEVICE AND METHOD FOR THE ELECTRICAL TREATMENT OF CANCER" filed Apr. 9, 1999; 60/377,840 for "PROGRAMMER AND INSTRUMENT FOR ELECTROCHEMICAL CANCER TREATMENT" filed May 7, 2002; 60/377,841 for "METHOD OF ELECTRICAL TREATMENT FOR CANCER IN CONJUNCTION WITH CHEMOTHERAPY AND RADIOTHERPAY filed May 7, 2002; 60/378,209 for "LEAD CONDUIT METHOD FOR ECT THERAPY" filed May 7, 2002; 60/378,210 for "DIELECTRIC SENSOR FOR ELECTROCHEMICAL CANCER THERAPY" filed May 7, 2002; 60/378,211 "INDIVIDUALLY IDENTIFIABLE ELECTROES FOR ELECTROCHEMICAL CANCER THERAPY" filed May 7, 2002; 60/378,212 for "MULTIPLE TUMOR TREATMENT FOR CANCER BY ELECTRICAL THERAPY" filed May 7, 2002; 60/378,213 for "PATIENT CONTROL FOR ELECTROCHEMICAL CANCER THERAPY" filed May 7, 2002; 60/378,214 for "OPTICAL FIBER ECT SYSTEM FOR PHOTOACTIVATED CYTOTOXIC DRUGS" filed May 7, 2002; 60/378,215 for "SPECIALIZED LEAD FOR ELECTROCHEMICAL CANCER TREATMENT" filed May 7, 2002; 60/378,216 "THREE-AXIS ELECTRODE SYSTEM TO CHASE THE CENTER OF TUMOR MASS" filed May 7, 2002; 60/378,629 for "CLOSED LOOP OPERATION OF ELECTROCHEMICAL TREATMENT FOR CANCER" filed May 9, 2002; 60/378,824 for "METHOD OF IMAGING BEFORE AND AFTER ELECTROCHEMICAL TREATMENT" filed May 9, 2002; 60/379,793 for "ECT AND ELECTROPORATION ELECTRODE SYSTEM" filed May 13, 2002; and 60/379,797 for "FIXATION MEANS LOCATED OUTSIDE TUMOR MASS FOR ECT FOR CANCER" filed May 13, 2002 all of which are herein incorporated by reference.

BACKGROUND OF THE INVENTION

1. Field of the Invention

This invention relates generally to the electrical treatment of malignant tumors and neoplasms by applying a voltage to affected tissue. Devices and various adaptations therein are described for use in electrical therapy. Additionally, various chemotherapeutic agents and radiation therapies are described which may be advantageously used in conjunction with electrical therapy to ameliorate cancer.

2. Discussion of the Related Art

Cancer is one of the major causes of hospitalization and death worldwide. However, many of the therapies applied to cancer treatment are either ineffective or not well-tolerated by patients.

Cancer malignancies result in approximately 6,000,000 deaths worldwide each year. In 1995, 538,000 cancer related deaths were reported in the United States, representing over 23% of the total deaths in the United States. This number has increased since 1970 when 331,000 deaths occurred. The estimated number of new cases in the United States in 1997 was 1,382,000. An astounding 40% of Americans will eventually be stricken with the disease and more than 1 in 5 will die from it. The percentage is increasing at about 1% per year and cancer deaths will soon outstrip deaths from heart disease.

Much of the medical care cost associated with cancer results from hospitalization. In 1994 there were 1,226,000 hospital discharges in the United States related to cancer treatment. The cost of cancer in terms of both human suffering and monetary expenditures is staggering. Effective treatment methods, which result in fewer days of hospital care, are desperately needed.

Primary treatment methods currently used in cancer therapy include surgery, radiation therapy, chemotherapy, hormone therapy and many others including bone marrow replacement, biological response modifiers, gene therapy, and diet. Therapy often consists of combinations of these treatment methods. It is well known that these methods may result in sickness, pain, disfigurement, depression, spread of the cancer, and ineffectiveness. Despite recent announcements of potential pharmaceutical "cures", which announcements of potential pharmaceutical "cures", which may work well in animals and in humans in certain cases, researchers are cautious in overstating their effectiveness. In the case of radiation treatment, rapid decreases in the size of poorly differentiated tumors after treatment may be experienced; however, shortly thereafter the tumor often experiences re-growth. Unfortunately, following re-growth the tumor is generally more insensitive to future radiation treatment attempts.

The approaches previously described, as well as other prior approaches, are not sufficient to meet the needs of real patients. The present invention addresses the above and other needs.

SUMMARY OF THE INVENTION

This invention relates generally to a method of treating cancer. It involves a device, either partially or totally implanted, consisting of a generator and one or more wires (or leads) containing one or more electrodes. The electrodes are implanted in or near the tumor and the generator may be implanted subcutaneously as close to the tumor as practical. The device is powered either by an implantable generator or via an external electrical source. The implantation is typically performed under local anesthesia and the device is generally left implanted for a period of months. With implantation, the device permits electric current to be applied at low levels for long periods of time. In another embodiment, the implanted device may be connected to an external device for energy input, data input, and/or therapy regimen modifications. While the internal generator is useful for applying low levels of electrical current for long periods of time, the external electrical source may be advantageously used to generate high levels of electrical current over shorter periods of time. In a preferred embodiment the external generator may produce currents and pulses useful in electroporation therapy. Additionally, methods and devices directed to chemotherapy and radiation therapy are described for use in conjunction with electrical therapy. In a preferred embodiment, electricity is provided in the form of direct current.

BRIEF DESCRIPTION OF THE DRAWINGS

The above mentioned and other objects and features of this invention and the manner of attaining them will become apparent, and the invention itself will be best understood by reference to the following description of the embodiments of the invention in conjunction with the accompanying drawings, wherein:

FIG. 2a-2d are diagrams illustrating examples of unipolar and multipolar lead placements suitable for use in an electrical therapy system;

FIG. 2g is a drawing illustrating an example of a multipolar lead placement with an adapter, such as for use with an electrical therapy system;

FIG. 3a-3c are drawings in front perspective, top view, and side perspective illustrating an example of an array of multiple electrodes on a lead comprising a ring of electrodes, a separate top electrode, and a plurality of fixation needles that may be used with an electrical therapy system;

FIG. 49 is an example of a user friendly data chart that can be used to display current information and to input changes to the controller of an external device used in electrical therapy.

DETAILED DESCRIPTION OF THE PREFERRED EMBODIMENT

Figure 1:
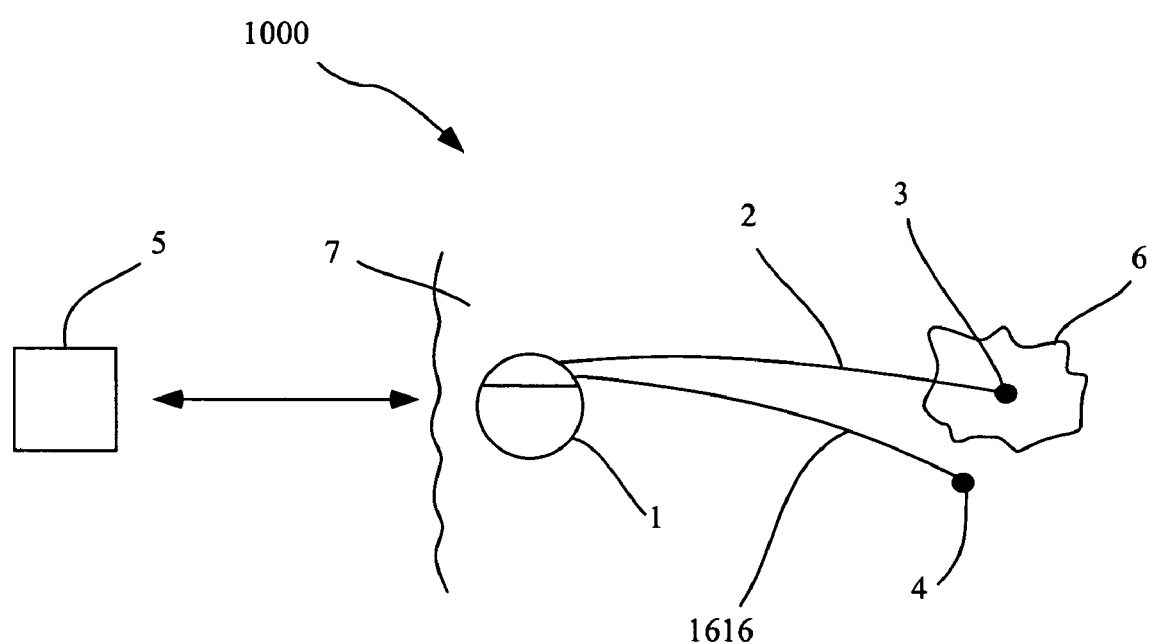
FIG. 1 is a diagram depicting an overall system in accordance with one embodiment.

The following description is of the best mode presently contemplated for practicing the invention. This description is not to be taken in a limiting sense, but is made merely for the purpose of describing the general principles of the invention. The scope of the invention should be ascertained with reference to the claims.

The devices and methods of the present embodiment are contemplated for use in patients afflicted with cancer or other non-cancerous (benign) growths. These growths may manifest themselves as any of a lesion, polyp, neoplasm (e.g. papillary urothelial neoplasm), papilloma, malignancy, tumor (e.g. Klatskin tumor, hilar tumor, noninvasive papillary urothelial tumor, germ cell tumor, Ewing's tumor, Askin's tumor, primitive neuroectodermal tumor, Leydig cell tumor, Wilms' tumor, Sertoli cell tumor), sarcoma, carcinoma (e.g. squamous cell carcinoma, cloacogenic carcinoma, adenocarcinoma, adenosquamous carcinoma, cholangiocarcinoma, hepatocellular carcinoma, invasive papillary urothelial carcinoma, flat urothelial carcinoma), lump, or any other type of cancerous or non-cancerous growth. Tumors treated with the devices and methods of the present embodiment may be any of noninvasive, invasive, superficial, papillary, flat, metastatic, localized, unicentric, multicentric, low grade, and high grade.

The devices and methods of the present embodiment are contemplated for use in numerous types of malignant tumors (i.e. cancer) and benign tumors. For example, the devices and methods described herein are contemplated for use in adrenal cortical cancer, anal cancer, bile duct cancer (e.g. periphilar cancer, distal bile duct cancer, intrahepatic bile duct cancer) bladder cancer, benign and cancerous bone cancer (e.g. osteoma, osteoid osteoma, osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell) esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin caner), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

Patients treated with the devices and methods of the present embodiment may be any living thing, but preferably a mammal such as, but not limited to, humans, monkeys, chimps, rabbits, rats, horses, dogs, and cats. Patients treated with the devices and methods of the present embodiment may be of any age (e.g. infant, child, juvenile, adolescent, adult, and even pregnant women and their unborn fetus, such as in the case of gestational trophoblastic disease).

The devices and methods of the present embodiment work to treat cancerous tumors by delivering electrical therapy continuously and/or in pulses for a period of time ranging from a fraction of a second to several days, weeks, and/or months to tumors. In a preferred embodiment, electrical therapy is direct current electrical therapy. For the purposes of discussion herein, the term "direct current (DC) electrical therapy" may be used interchangeably with "direct current (DC) ablation". Additionally, for the purposes of discussion herein, the term "electrical therapy" may refer to any amount of coulombs, voltage, and/or current delivered to a patient in any period of time. For example, coulombs, voltage, and/or current used at levels sufficient for DC ablation (which are generally lower coulombs, voltage, and/or current and longer periods of time) and coulombs, voltage, and/or current used at levels sufficient for electroporation (which are generally higher coulombs, voltage, and/or current and shorter periods of time) are both included in "electrical therapy". Furthermore, "electroporation" (i.e. rendering cellular membranes permeable) as used herein may be caused by any amount of coulombs, voltage, and/or current delivered to a patient in any period of time sufficient to open holes in cellular membranes (e.g. to allow diffusion of molecules such as pharmaceuticals, solutions, genes, and other agents into a viable cell).

Delivering electrical therapy to tissue causes a series of biological and electrochemical reactions. At a high enough voltage, cellular structures and cellular metabolism are severely disturbed by the application of electrical therapy. Although both cancerous and non-cancerous cells are destroyed at certain levels of electrical therapy, tumor cells are more sensitive to changes in their microenvironment than are non-cancerous cells. Distributions of macroelements and microelements are changed as a result of electrical therapy.

Electrical therapy produces various byproducts including hydrogen, oxygen, chlorine, and hydrogen peroxide. Hydrogen peroxide is known to destroy living tissues whereas the effect of the other reaction products on living tissues varies. The byproducts and changes in tissue that result from electrical therapy are differentially experienced throughout the tissue based on the positioning of the anode and cathode. For example, chlorine, which is a strong oxidant, is liberated at the anode, whereas hydrogen is liberated at the cathode. Additionally, the concentration of chlorine ions is high around the anode while the concentration of sodium and potassium ions is found to be higher around the cathode. pH changes due to electrical therapy cause the tissue around the anode to become strongly acidic, down to 2.1, while the tissue around the cathode becomes strongly basic, up to 12.9. Water migrates from the anode to the cathode while fat moves from the cathode to the anode, causing local hydration around the cathode and dehydration around the anode. Proteins may be denatured in electrical therapy. For example, hemoglobin is transformed into acidic hemoglobin around the anode and alkaline hemoglobin around the cathode.

Electrochemical reactions as a function of pH and electrode potential can be predicted by means of a Pourbaix diagram in *Aqueous Solutions*—Pergamon Press, 1986—by Pourbaix, which is herein incorporated by reference.

As is readily understood by those of ordinary skill in the art, the coulomb (C) is the basic unit of charge (e.g. the magnitude of the charge on an electron or a proton is $1.6 \times 10^{-19}$ coulombs—where the charge on an electron is negative and the charge on a proton is positive). Electrical therapy may be described as the application of voltage in volts (V), current in amperes (A), and/or total coulombs (C) delivered. Voltage is a measure of force per unit of charge. Voltage causes charge (i.e. current) to flow in a particular direction. Current, is the rate that charge passes through a medium. Moreover, charge delivered in coulombs is equal to the current level in amperes multiplied by the time in seconds (i.e. charge (C)=current (A)*time (s)). In a wire (or lead) current is carried by electrons. In extracellular fluid (such as in a tumor), current may be carried by an ion in solution.

Although electrical therapy examples described hereinbelow may be expressed in voltage (i.e. volts) and/or current (i.e. amperes), it should be understood that by applying Ohm's law, which states that voltage and current are proportional (i.e. V=IR), the equivalent voltage to current or current to voltage may be calculated. The proportionality constant is the resistance (R) in the electrode/tissue system. Resistance is measured in Ohms (O) and is equal to one volt per ampere. Resistance is the property of a material to resist current flow. In the electrical therapy system described herein, resistance may be caused by any number of factors including tumor density, tumor consistency, tumor volume, tumor location, pharmaceuticals utilized, wire(s) (or lead) utilized, electrode(s) utilized, and patient characteristics such as weight, age, gender, and diet. Because resistances may change with long-term electrical therapy, it may be advantageous to program the devices of the present embodiment in terms of current instead of voltage. For example in DC ablation, if 10 mA are applied to a tumor with a resistance of 100 O the corresponding voltage is 1 V. However, if 10 mA are applied to a tumor with a resistance of 25 Ω the corresponding voltage is 0.25 V. In another example consistent with electroporation, if 500 V are applied to a tumor with a resistance of 25 Ω the corresponding current is 20 A. However, if 500 V are applied to a tumor with a resistance of 100 Ω the corresponding current is 5 A.

Electrical therapy may also be described as total coulombs (C) delivered. As will be appreciated by those of ordinary skill in the art, describing electrical therapy in terms of total coulombs (C) delivered can apply to numerous ranges of volts and amperes dependent on the resistance of the system and the rate of delivery. Therefore, because resistance may vary widely from one tumor to another, each of the examples of the preferred embodiments described herein are merely examples and are not limiting. In each situation resistance of a tumor may be measured prior to application of electrical therapy to determine the appropriate voltage, current, and/or coulombs to be delivered.

For example, if a dose of 0.5 C is applied to a tumor the resulting voltage and current varies dependent on the rate at which the charge is delivered and the resistance of the system. If, for example, the resistance of the system is 100 Ω and the rate of delivery is over 10 seconds then the resulting current is 0.05 A (50 mA) and the resulting voltage is 5 V. In some circumstances it may be advantageous to deliver the charge over a longer time period such as in DC ablation. For example, if a dose of 25 C is applied to a tumor over 1 hour and the resistance is 100 Ω then the resulting current is 0.007 A (7 mA) and the resulting voltage is 0.7 V. In electroporation, electrical therapy is delivered over a short time period. For example, if 1 mC is applied to a tumor over 1 ms and the resistance is 1000 O then the resulting voltage is 1000 V and the resulting current is 1 A.

With regard to the preferred methods of the embodiment, single electrode and/or multi-electrode configurations of the preferred embodiment may be used in conjunction with electrical therapy regimens.

In the case of a single electrode configuration, high voltage may be applied for minutes to hours between a lead electrode and the generator housing, which generates a pH change of at least 2 in either direction to begin destruction of cancerous tissue. Following application of high voltage, a rest period, marked by idling of the device, is optionally entered. Later, low voltage is applied for hours to days, which may attract white blood cells to the tumor site. In this way, the cell mediated immune system may remove dead tumor cells and may develop antibodies against tumor cells. Furthermore, the stimulated immune system may attack borderline tumor cells and metastases. Molecular chlorine generated at the anode may kill additional local tumor cells.

Various adjuvants may be used to increase any immunological response, depending on the host species, including but not limited to Freund's adjuvant (complete and incomplete), mineral salts such as aluminum hydroxide or aluminum phosphate, various cytokines, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof.

In the case of a multi-electrode configuration, high voltage may be applied for minutes to hours between a first set of one or more electrodes and either a second set of one or more other electrodes, or the generator housing.

In any case, high voltage may be applied for minutes to hours between at least one anode and at least one cathode.

Any number and configuration of electrodes comprising either anodes or cathodes, or anodes and cathodes may be used.

In some embodiments the generator housing serves as either an anode or a cathode.

As with the single electrode configuration, the high voltage applied between at least one anode and at least one cathode generates a pH change of at least 2 in either direction to begin necrosis. Following application of high voltage, a rest period, marked by idling of the device, is optionally entered. Later, low voltage is applied for hours to days, which may attract white blood cells to the tumor site. In this way, the cell mediated immune system may remove dead tumor cells and may develop antibodies against tumor cells. Furthermore, the stimulated immune system may attack borderline tumor cells and metastases.

As previously described, various adjuvants may be used to increase any immunological response.

Additionally, electrical therapy may be used in conjunction with chemotherapy and radiation therapy. Steps relating to single electrode and/or multi-electrode therapies may be followed by steps specifically designed for chemotherapy and radiation therapy.

In the case of electrical therapy used in conjunction with chemotherapy, at least one remote cathode may be implanted near a chemotherapy administration site, or other site if the chemotherapy agent is administered systemically. Next, a chemotherapy agent is administered. Following administration of a (positively charged) chemotherapeutic agent, medium voltage is applied between at least one anode (e.g. the generator housing or first electrode coupled to the generator housing by a first lead) and at least one remote cathode (e.g. an electrode coupled to the generator by a lead or second electrode coupled to the generator by a second lead) to direct a chemotherapeutic agent to the tumor site. Alternatively, medium voltage may be applied between at least one cathode and at least one remote anode to direct a chemotherapeutic agent to the tumor site. Following the medium voltage step, the polarity of the generator housing (or first electrode) may switch with the polarity of the electrode (or second electrode) such that the generator housing (or first electrode) becomes cathodic and the electrode (or second electrode) becomes anodic. By reversing polarity of the generator housing (or first electrode) and electrode (or second electrode), the chemotherapeutic agent is dispersed throughout the peripheral tumor mass. Following polarity reversal, electroporation electrical therapy may be optionally administered to the tumor site in order to increase permeability of the cells to allow enhanced uptake of a chemotherapeutic agent. As is described hereinbelow, the devices and methods of the present embodiment may be adjusted for other variations, such as in the case of a negatively charged chemotherapy agent.

In the case of electrical therapy used in conjunction with radiation therapy, following the electrical therapy regimen as described for single electrode and/or multi-electrode configurations of the preferred embodiment, high voltage is applied to all electrodes, thereby forcing all electrodes anodic, for minutes to generate molecular oxygen. Alternatively, various substances may be administered to oxygenate tissue, as described hereinbelow. In this embodiment, localized hyperoxia significantly increases brachytherapy effectiveness. As such, brachytherapy may be applied concomitantly to enhance the effects of electrical therapy.

Each of the previously described methods and method steps therein may be used in conjunction with each other for increased effectiveness. For example, chemotherapy and radiation therapy may be used in conjunction with the methods for unipolar and/or bipolar treatments.

Complexity of the device and therapeutic regimen can vary considerably, depending upon its desired flexibility of use. The device in its simplest form may consist of a single lead permanently connected to a generator encapsulated in plastic or potting compound (with an embedded generator housing electrode) with a fixed DC output voltage. Alternatively, a complicated device may have numerous options and configurations ideal for any particular situation. Examples of the numerous options and configurations suitable for implementing various embodiments are described in full detail hereinbelow. A therapeutic regimen in its simplest form may consist of a single voltage applied to a single electrode for an amount of time. However, many complicated therapeutic regimens are also contemplated. Examples of the types of complex therapeutic regimens suitable for implementing various embodiments are apparent in the following description.

The cancer therapy system of several embodiments differs from implantable pacemaker systems in various ways. For example, pacemakers are generally implanted for years while the device of such embodiments is typically implanted for months, until the cancerous condition has been ameliorated. The cancer therapy system described herein is not life-supporting as opposed to pacemakers, which are relied on by patients to stimulate their heartbeat. The generator housing of cancer therapy systems may have lower hermeticity requirements (i.e. higher leak rate tolerance) in comparison to hermeticity requirements of housings used with pacemaker generators because the device of the present embodiment is designed to be implanted for months not years. The leads of the present embodiment may have less stringent mechanical requirements since they are not stressed by movement (such as by the movement created by a beating heart) to the degree of pacemakers and are required for shorter periods of time, again months not years. Additionally, in most cases electromagnetic interference is not a concern with the cancer therapy system of the present embodiment as it is with pacemaker systems. However, electromagnetic interference may be a concern in the case of highly specialized systems wherein certain sensors are employed.

Referring now to the drawings, further features and embodiments are now described.

1. Overview of Device

In FIG. 1, a system 1000 of the present embodiment for treating cancer is depicted. The system 1000 comprises a generator 1, one or more implanted wires or leads 2 and 1616, an anode electrode 3, a cathode electrode 4, and an external instrument 5. The generator 1 and the leads 2 and 1616 are implanted into a body 7 in a subcutaneous area as near as practical to a tumor 6, but out of a path of any potentially planned ionizing radiation. The leads 2 and 1616 may terminate with either an anode electrode 3 or a cathode electrode 4. The anode electrode 3 and the cathode electrode 4 are implanted inside or outside of the tumor 6. In a preferred embodiment, the anode electrode 3 is implanted in the center of the tumor 6 and the cathode electrode 4 is implanted outside the tumor 6 as shown, or in the tumor's internal periphery (i.e. in the vicinity of a cancerous tumor). The leads 2 and 1616 are tunneled subcutaneously from the generator 1 to the tumor 6. The lead 1616 terminating with the cathode electrode 4 may be alternatively placed into a blood vessel (not shown) near tumor 6. The system 1000 may also comprise an external instrument 5 used to communicate with the generator 1. The external instrument 5 is operably coupled to the generator 1 via coupling means, which coupling means may be physical and/or telemetric and may include any of a universal serial bus (USB), a serial port, a Personal Computer Memory Card International Association (PCMCIA) card, and a radio frequency (RF). The external instrument 5 may alter various parameters including rate, intensity, and duration of therapy. The external device 5 of the embodiment allows for inputting of data or manipulating of therapy non-invasively.

2. Leads

FIG. 2a-2d and FIG. 2g depict various options for leads to be used with the cancer therapy system of the present embodiment. Shown in FIG. 2a-2d and FIG. 2g are the generator 1; the tumor 6; a unipolar lead 8; a single electrode 9; a multipolar lead 10; two or more electrodes 11 and 12; multiple unipolar leads 13 and 14; multiple multipolar leads 15, 16, 17, and 25; multiple electrodes 18, 19, 20, 21, 22, and 23; an adapter 24; lead extensions 26 and 27; a same electrical connection 28; a common lead segment 1001; and a different electrical connection 1002.

In FIG. 2a, the unipolar lead 8 is depicted. The unipolar lead 8 of FIG. 2a may be permanently coupled to a generator 1 such as with a hermetic feedthrough or may, alternatively, be coupled with a detachable coupling means such as a hermetically sealed and/or biocompatible plug and socket connector. In any case, the unipolar lead 8 is operably coupled to the generator 1 such that the unipolar lead 8 is energized when the generator 1 is activated, thereby energizing electrode 9 as well. The end of the unipolar lead 8, opposite the generator 1, terminates with the single electrode 9. The single electrode 9 may be implanted in or adjacent to a tumor 6. In this case, the electrode 9 is shown implanted inside the tumor 6. In a preferred embodiment, the unipolar lead 8 terminates with an anode electrode while the generator housing serves as the cathode electrode. Alternatively, the unipolar lead 8 may terminate with a cathode electrode while the generator housing serves as the anode electrode. In a preferred embodiment, the generator 1 contains internal circuitry so that the polarity of the single electrode 9 and the polarity of the generator 1 may switch. For example, in the case that therapy begins with the single electrode 9 serving as an anode and the generator housing 1 serving as a cathode, later, after a time period, internal circuitry may switch the polarity so that the single electrode 9 serves as the cathode and the generator housing 1 serves as the anode.

FIG. 2b shows a multipolar lead 10. The multipolar lead 10 of FIG. 2b is operably coupled, either permanently or detachably, at one end with the generator 1 and terminates with the two or more electrodes 11 and 12, which may be implanted in or adjacent to (i.e. in the vicinity of) the tumor 6 such that when the generator 1 is activated, energy flows from the generator 1 through the multipolar lead 10 and to the two or more electrodes 11 and 12 which are then consequently energized. The electrodes 11 and 12 may interchangeably serve as the anode and the cathode. For example, at the beginning of treatment, the electrode 11 may be designated as the anode while the electrode 12 may be designated as the cathode, or vice versa. Then, during therapy, the polarity of the electrodes may change (reverse), such that the electrode 11 becomes the cathode and the electrode 12 becomes the anode. In another embodiment, both electrodes 11 and 12 of the lead may simultaneously serve as anodes while the generator housing serves as the cathode, or vice versa, and their polarities may change.

In FIG. 2c, multiple unipolar leads 13 and 14 are operably coupled, either permanently or detachably, at one end to the generator 1 and terminate at the end opposite the generator 1 with one or more electrodes 11 and 12. In this embodiment, the electrodes 11 and 12 are implanted adjacent to the tumor 6. However, in another embodiment, the electrodes 11 and 12 may be implanted into the tumor 6. The electrodes 11 and 12 each may serve as either an anode or a cathode (and may change polarity as described above). In another embodiment, both electrodes 11 and 12 may simultaneously serve as anodes while the generator housing serves as the cathode, or vice versa, and their polarities may change.

Referring now to FIG. 2d, three multipolar leads 15, 16, and 17 are shown. Each of the multipolar leads 15, 16, and 17 are operably coupled at one end to the generator 1. The multipolar leads 15, 16, and 17 may be permanently coupled to the generator 1 or may, alternatively, be coupled with a detachable means, such as described hereinabove. At the end of the multipolar leads 15, 16, and 17, opposite the generator 1, the multipolar leads 15, 16, and 17 terminate with multiple electrodes 18, 19, 20, 21, 22, and 23 (including tip electrodes 19, 21, 23 and ring electrodes 18, 20, 22). In one embodiment, the multiple electrodes 20 and 21 are anode electrodes and the multiple electrodes 18, 19, 22, and 23 are cathode electrodes. In another embodiment, the ring electrodes 20, 18, and 22 may each serve as an anode while the tip electrodes 21, 19, and 23 may each serve as a cathode, or vice versa. However, the multiple electrodes 18, 19, 20, 21, 22, and 23 may function in any combination of anodes and cathodes.

Figure 2E:
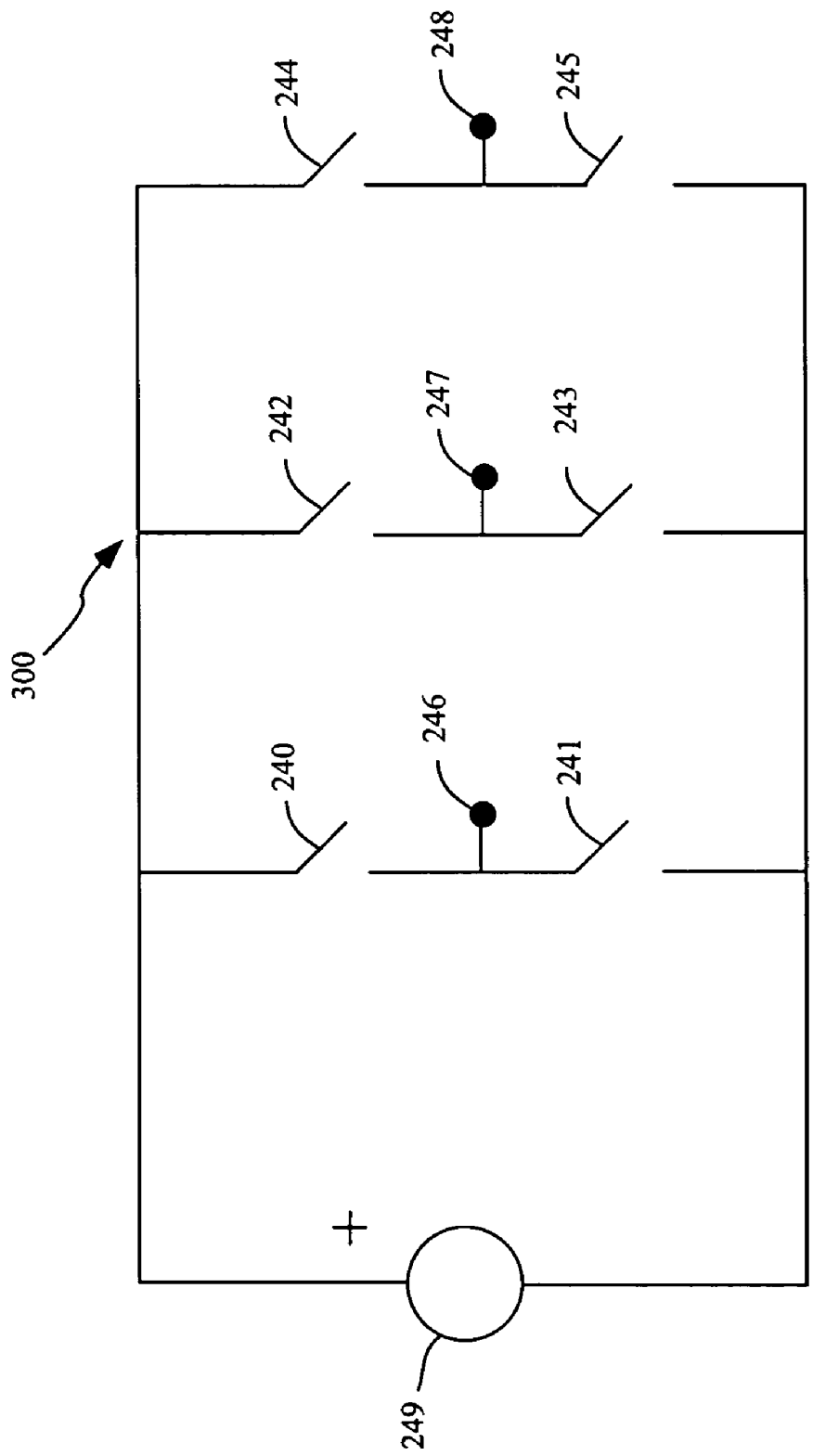
FIG. 2e-2f are schematic diagrams showing examples of circuitry for switching electrode polarity, such as for use with an electrical therapy system.
Figure 2F:
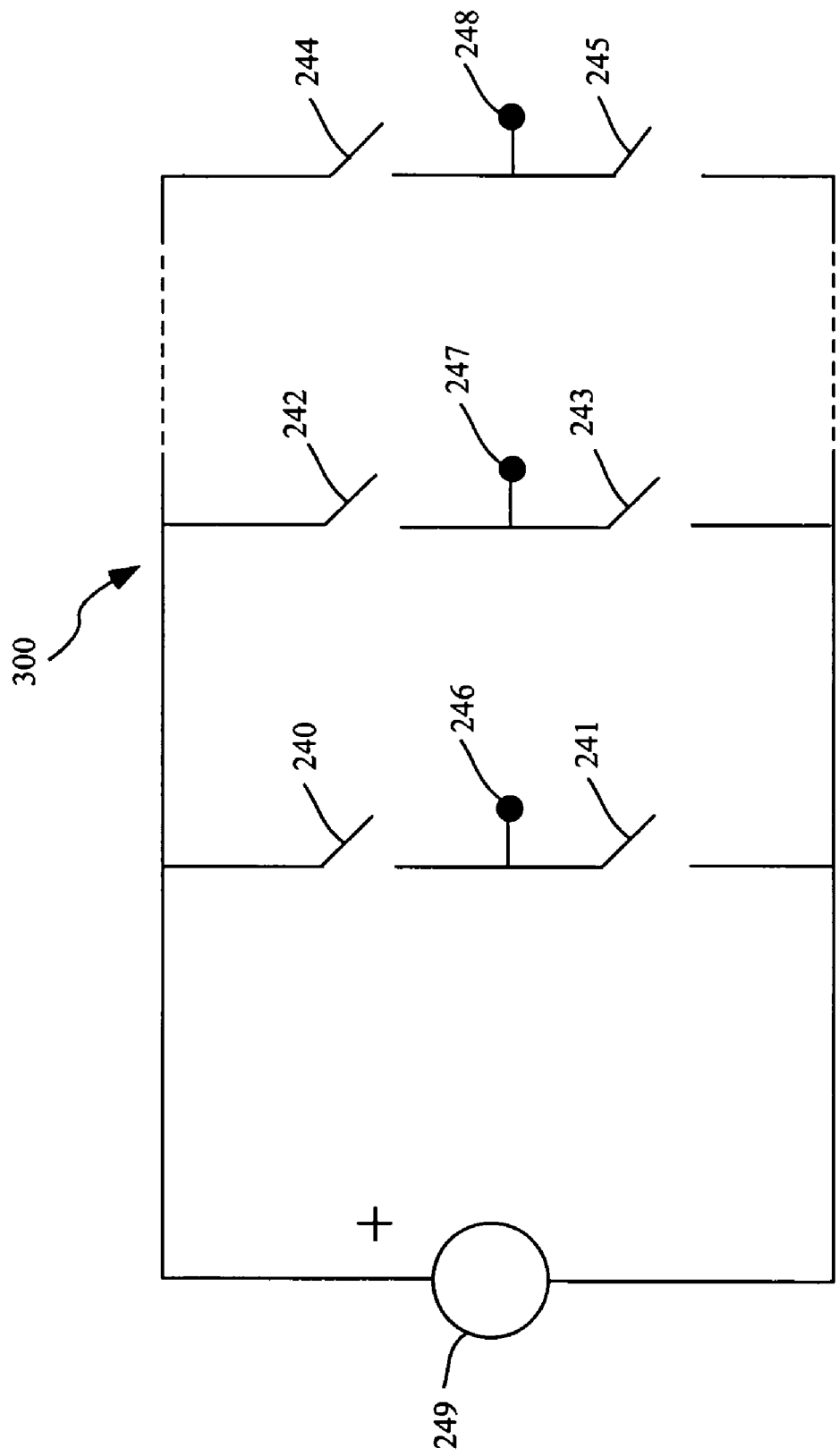

Internal circuitry permits electrode switching as previously described. Turning now to FIG. 2e-2f, a hex bridge 300 which may be advantageously used in conjunction with the embodiments described herein is illustrated. Shown are a hex bridge 300; current source 249 with the positive output shown on top; switches 240, 241, 242, 243, 244, and 245; electrodes 246 and 247; and a generator housing 248. By opening and closing switches 240, 241, 242, 243, 244, and 245, electrodes 246, 247, and the generator housing 248 may be switched from an anode to a cathode or vice versa. For example, by closing switch 240 and switch 243, current flows from the current source 249 through the switch 240 to the electrode 246 then passes through tissue (not shown) to the electrode 247, through the switch 243 and back to the current source 249. In this example, the electrode 246 serves as an anode while the electrode 247 serves as a cathode. In another example, by opening the switch 240, and the switch 243, and by closing switch 242 and switch 241, electricity flows from the current source 249 through the switch 242 to the electrode 247, then passes through the tissue to the electrode 246 through the switch 241 and back to the current source 249. In this example, the electrode 247 serves as the anode and the electrode 246 serves as the cathode.

As illustrated by the previous two examples, the electrode 246 may serve as either the anode or the cathode and the electrode 247 may serve as an anode or a cathode. The electrodes 246, 247 may be electrodes of separate unipolar leads, or may be tip and ring electrodes of a bipolar electrode.

As will be appreciated by those of ordinary skill in the art, numerous configurations of anode(s) and cathode(s) based on these principles may be achieved by the type of circuit illustrated in FIG. 2e-2f. For example, both of the electrodes 246, 247 may be configured as the anode or both of the electrodes 246, 247 may be configured as the cathode. And, in a similar manner, the generator housing 248 can be selectively configured as the anode or the cathode, either in addition to or instead of one of the electrodes 246, 247. Importantly, the circuit as illustrated in FIG. 2e-2f may have any number of switches and any combination of such switches may be closed or opened to treat tumors with electrical therapy. The switches described hereinabove may be discrete, or solid state and/or software controlled or electronically controlled. Furthermore, any number of electrodes and configurations are contemplated by the inventors. For example, as shown in FIG. 2f, any number of electrodes may be coupled to the hex bridge 300 electrically between switch 242 and switch 244 and electrically between switch 243 and switch 245, as is indicated by dashed lines. The electrodes of FIG. 2f, like the electrodes of FIG. 2e, may be of any configuration, especially such as those described herein.

Looking now to FIG. 2g, a common lead segment 1001 of the present embodiment comprising a lead adapter 24 is shown. The lead adapter 24 of this embodiment allows the lead extensions 26 and 27 to enter the generator 1 via the common lead segment 1001 at the same electric connection 28. The lead 25 enters the generator 1 in a different electric connection 1002 than lead extensions 26 and 27. The lead adapter 24 permits the use of additional leads such as lead extensions 26 and 27 under certain circumstances. The lead adapter 24 may be advantageously used when a large tumor and/or multiple tumors are being treated by a single generator 1. Importantly, the lead adapter 24 allows for adaptation during implantation or treatment. If, for example, an additional tumor is formed or found at a later date than at initial implant of the device of the preferred embodiment, use of the lead adapter 24 (or multiple lead adapters) allows flexibility in the implanted device. Adjusting the number of leads via a lead adapter may be preferable to extricating and replacing the entire implanted device or adding an additional implanted device. Leads used in conjunction with the lead adapter 24 may be unipolar and multipolar, anode and cathode, may contain any number of electrodes, and may be placed internally and externally relative to a tumor or both internally and externally. The lead adapter 24 may take on any form useful to electrically couple current from two or more leads to the same electric connection 28. However, in a preferred embodiment, the adapter may be shaped like a "Y".

Many variations of lead configurations are possible and, likewise, possibilities of electrode placement are equally numerous. The above are but a few examples of the types of lead configurations and electrode placements possible. As shown above, the leads of the present embodiment may be multipolar and unipolar and of various lengths, sizes, and shapes. Furthermore, the leads may terminate with electrodes that are anode and/or cathode, and be implanted into, adjacent to, and/or in the internal periphery of a tumor. In any event, the electrodes and leads of the preferred embodiment should be configured so that an electric field encompasses as much of the tumor as possible (or alternatively a target portion of the tumor) while excluding the majority of the surrounding tissue.

Figure 3A:
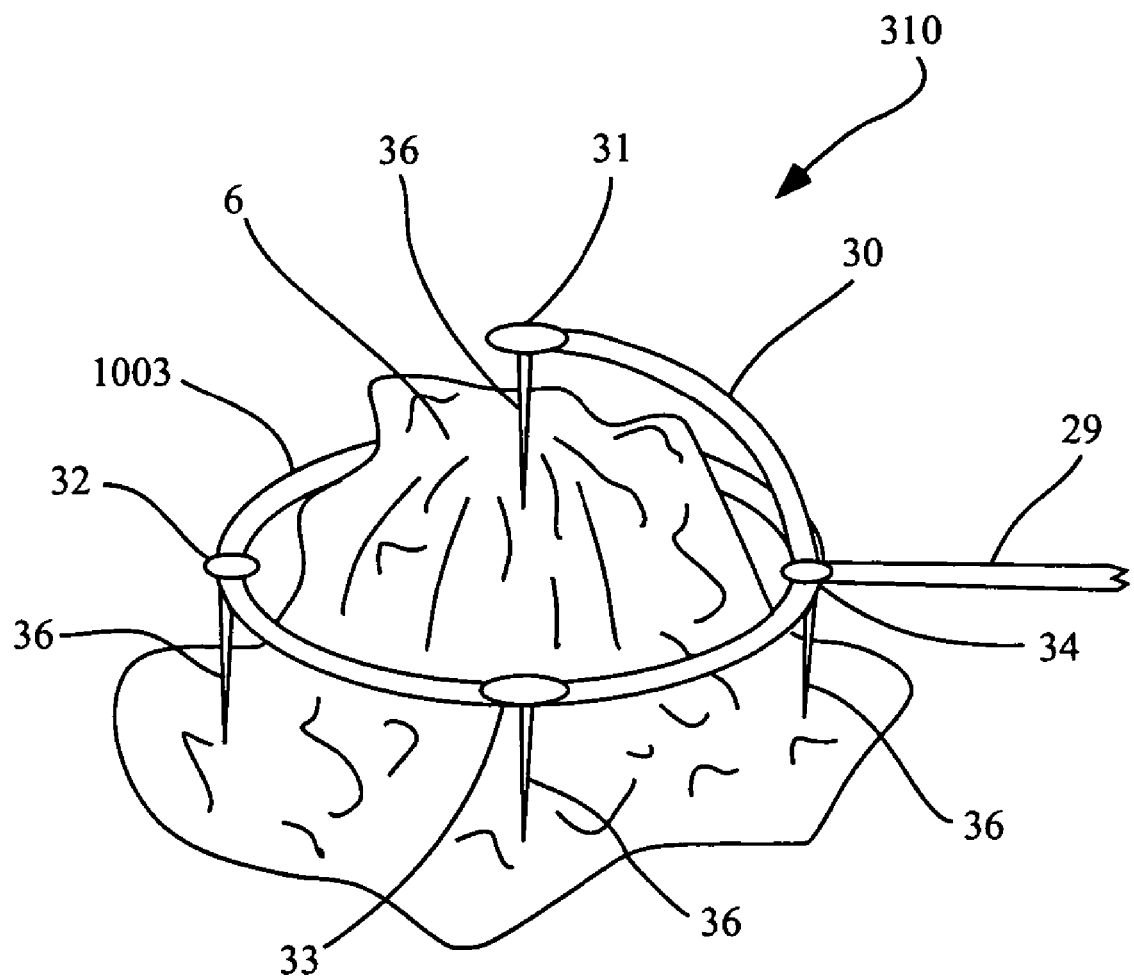

Depicted in FIG. 3a-3c is an electrode array 310. Shown are the electrode array 310; a tumor 6; a wire bundle 29; insulated wire segment 30; electrodes 31, 32, 33, 34, and 35; needles 36; and insulated wire ring 1003. FIG. 3a is a front perspective of the electrode array 310 wherein the entire mass of the tumor 6 is surrounded by the electrodes 31, 32, 33, 34, 35. The electrode 31 is placed at the top of the tumor 6 via insulated wire segment 30, while electrodes 32, 33, 34, and 35 surround the tumor 6 via insulated wire ring 1003. The electrode 35 is depicted behind the tumor 6 and is therefore not visible from the perspective of FIG. 3a. The electrodes 32, 33, 34, and 35 are coupled together in a ring via insulated wire ring 1003. The electrode 34 is coupled to a distal end of the wire bundle 29. The electrode 31 is electrically coupled to the wire bundle 29 via the insulated wire segment 30 through the electrode 34. A proximal end of the wire bundle 29 is coupled to a generator (such as in FIG. 1) which provides electrical therapy to the electrodes 31, 32, 33, 34, and 35. Current paths can be switched by the generator (not shown), such as by using circuitry similar to that depicted in FIG. 2e-2f, so that a current pulse can flow from the electrode 35 to the electrode 31, then from the electrode 34 to the electrode 31, then from the electrode 33 to the electrode 31, then from the electrode 32 to the electrode 31, and so on in any sequence by delivering pulses of current between successive pairs of the electrode 31 and a remaining one of the electrodes 32, 33, 34, and 35. Each electrode is fixed to tissue via the needles 36, which may or may not serve as part of the electrode. The electrodes 31, 32, 33, 34, and 35 may selectively comprise any combination of anodes and cathodes. In another embodiment, all of the electrodes 31, 32, 33, 34, and 35 may simultaneously serve as anodes while the generator housing (not shown) serves as the cathode, or vice versa.

FIG. 3b is a top view of the electrode array 310 comprising electrodes 31, 32, 33, 34, and 35; wire bundle 29; insulated wire segment 30; and insulated wire ring 1003 of FIG. 3a. The electrode 35, hidden in FIG. 3a is seen on FIG. 3b. FIG. 3c is a side perspective of the electrode array 310 comprising electrodes 31, 32, 33, 34, and 35; wire bundle 29; insulated wire segment 30; and insulated wire ring 1003 of FIG. 3a. The needles 36 are coupled to the electrodes 31, 32, 33, 34, and 35. Two or more electrodes may simultaneously be used as anodes or cathodes for electrical therapy. The electrodes 31, 32, 33, 34, and 35 comprise an electrode array 310 that can be used to increase the effectiveness of electrical therapy by establishing an electric field pattern that encompasses all of the tumor volume. In a preferred embodiment, this type of electrode array 310 can be used for electrochemical therapy and/or electroporation.

Figure 4:
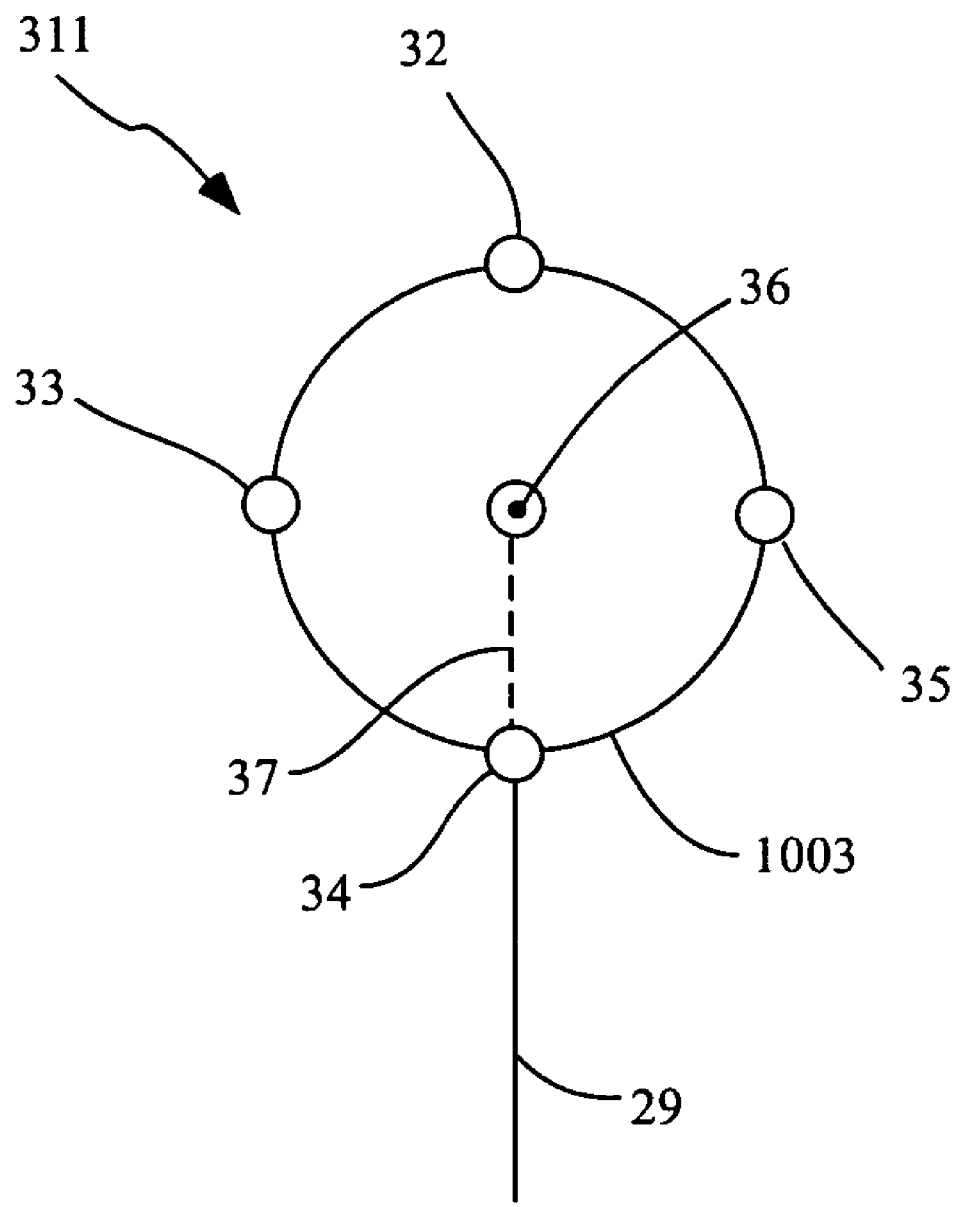
FIG. 4 is a drawing in top view illustrating an example of an array of multiple electrodes on a lead comprising a ring of electrodes and a fixation needle unattached to any electrode such as may be employed in an electrical therapy system.

Turning now to FIG. 4 a top view of an electrode array 311 is depicted. The electrode array 311 of FIG. 4 has been modified from the electrode array 310 of FIG. 3a-3c by including four electrodes 32, 33, 34, and 35 instead of five electrodes 31, 32, 33, 34, and 35 and coupling a single needle 36 for fixation to a central non-electrical connection 37. Shown are a wire bundle 29; the electrodes 32, 33, 34, and 35; the needle 36; the central non-electrical connection 37; and the insulated wire ring 1003. The electrodes 32, 33, 34, and 35 are anchored to a tissue via the needle 36, which is not directly associated with any one of the electrodes 32, 33, 34, and 35. Needle 36 is mechanically coupled to the electrode array 311 via the central non-electrical connection 37 but, as depicted, is electrically isolated from the electrodes 32, 33, 34, and 35.

Figure 5A:
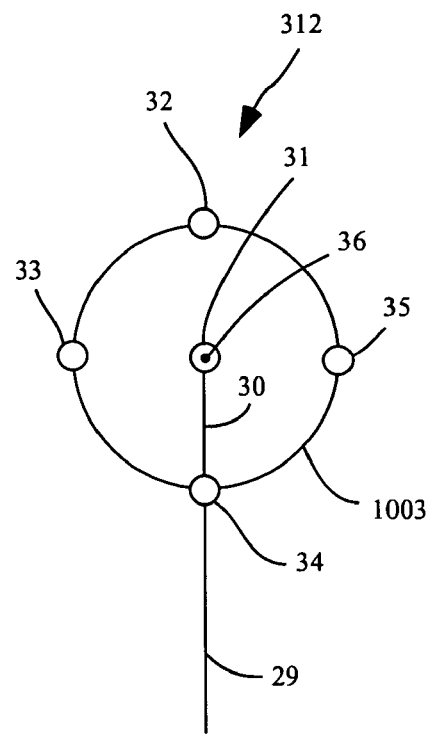
FIG. 5a-5b are drawings in top view and side perspective illustrating an example of an array of multiple electrodes on a lead comprising a ring of electrodes, a separate top electrode, and a single fixation needle such as may be employed in an electrical therapy system.
Figure 5B:
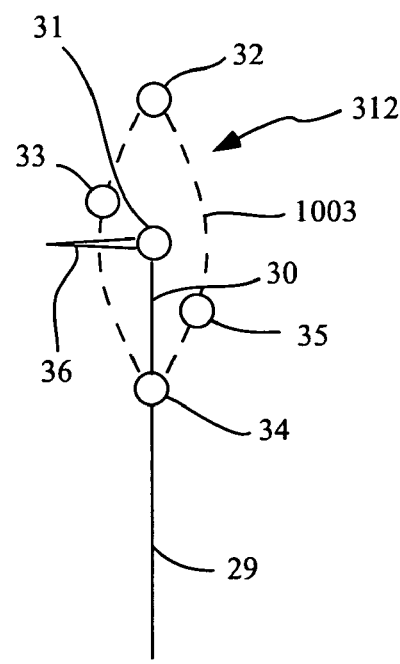

Illustrated in FIG. 5a-5b is an electrode array 312. The electrode array 312 of FIG. 5a-5b has been modified from the electrode array of FIG. 3a-3c 310 by utilizing a single needle 36 to anchor the electrode array 312. Shown are the electrode array 312; a wire bundle 29; an insulated wire segment 30; electrodes 31, 32, 33, 34, and 35; the needle 36; and an insulated wire ring 1003. FIG. 5a is a top view and FIG. 5b is a side perspective view. In FIG. 5a each of the electrodes 31, 32, 33, 34, and 35 is coupled to the wire bundle 29 via the insulated wire ring 1003. The electrodes 32, 33, 34, and 35 are coupled to the insulated wire ring 1003, while the electrode 31 is coupled independently to the wire bundle 29 via the insulated wire segment 30. Only the electrode 31 is mechanically coupled to the needle 36 as an anchoring means. The needle 36 may or may not serve as part of the electrode 31. FIG. 5b is a side perspective of FIG. 5a.

Figure 6A:
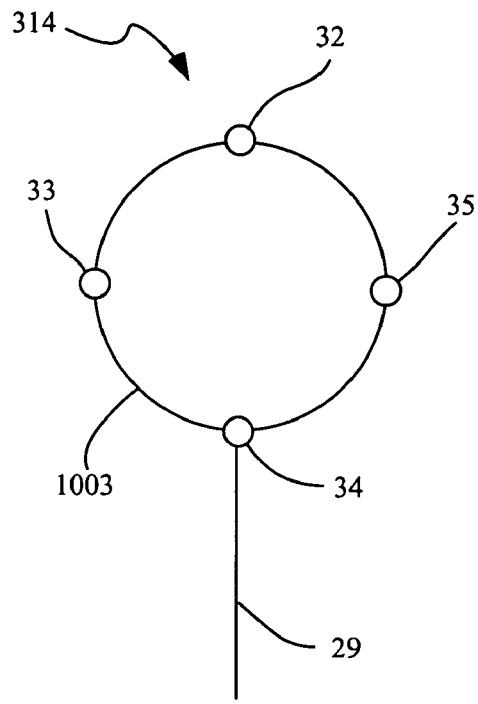
FIG. 6a-6b are drawings in top view and side perspective illustrating an example of an array of multiple electrodes on a lead comprising a ring of electrodes such as may be employed in an electrical therapy system.
Figure 6B:
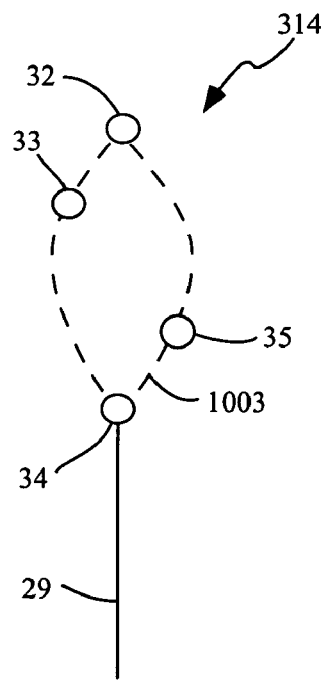

Shown in FIG. 6a-6b is an electrode array 314. The electrode array 314 of FIG. 6a-6b has been modified from the electrode array 310 of FIG. 3a-3c by including four electrodes 32, 33, 34, and 35 instead of five and by removing all fixation needles. Shown are the electrode array 314; the wire bundle 29; the electrodes 32, 33, 34, and 35; and an insulated wire ring 1003. FIG. 6a is a top view and FIG. 6b is a side perspective view. In FIG. 6a each of the electrodes 32, 33, 34, and 35 is coupled to the wire bundle 29 via the insulated wire ring 1003. No electrode is coupled to a needle for fixation means. In this case, the electrode array is placed on top of or around a tumor. In FIG. 6b, the electrodes 32, 33, 34, and 35 are shown coupled together via the insulated wire ring 1003 to the wire bundle 29. No electrode is coupled to a needle for placement or anchoring means.

Figure 7A:
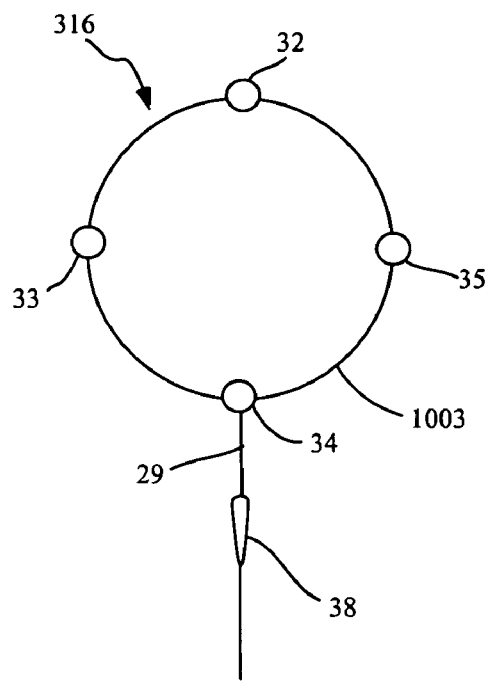
FIG. 7a-7b are diagrams shown in top view and side perspective illustrating an example of an array of multiple electrodes on a lead comprising a ring of electrodes and an anchoring hook such as may be used with an electrical therapy system.
Figure 7B:
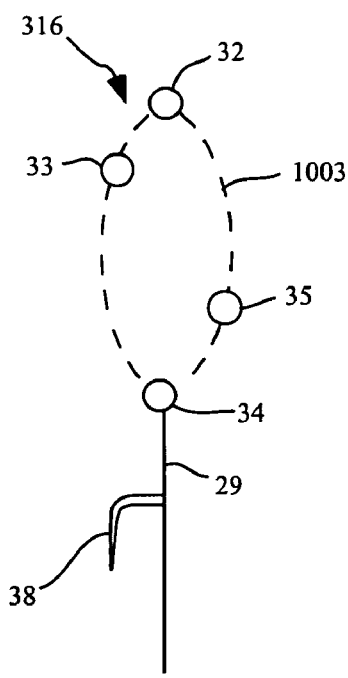

FIG. 7a-7b are illustrations of an electrode array 316. The electrode array 316 of FIG. 7a-7b has been modified from the electrode array 310 of FIG. 3a-3c by including four electrodes 32, 33, 34, and 35 instead of five and by using an anchoring hook in lieu of a fixation needle or needles. Shown are the electrode array 316; a wire bundle 29; electrodes 32, 33, 34, and 35; an anchoring hook 38; and an insulated wire ring 1003. FIG. 7a is a top view and FIG. 7b is a side perspective view. In FIG. 7a each of the electrodes 32, 33, 34, and 35 is coupled to the wire bundle 29 via the insulated wire ring 1003. No electrode is directly coupled to a needle for fixation. Instead, an anchoring hook 38 is coupled to the wire bundle 29; however, the anchoring hook 38 can be placed at any place on the electrode array 316. The anchoring hook 38 secures placement of the electrode array 316 by hooking into tissue. In one variation, the anchoring hook 38 may be secured to healthy tissue to increase stability. In FIG. 7b the electrodes 32, 33, 34, and 35 are shown coupled together via insulated wire ring 1003 to wire bundle 29. The anchoring hook 38 is shown coupled to wire bundle 29.

In accordance with further variations, the anchoring hook 38 or several anchoring hooks may be used either alone or in combination with a fixation needle or needles.

Figure 8A:
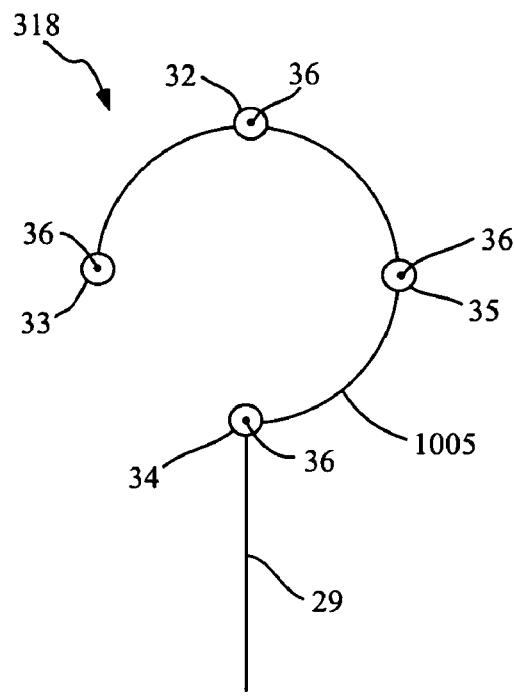
FIG. 8a-8b are illustrations in top view and side perspective depicting an example of an array of multiple electrodes on a lead comprising a segment of electrodes not in closed ring formation and a plurality of fixation needles such as may be employed in an electrical therapy system.
Figure 8B:
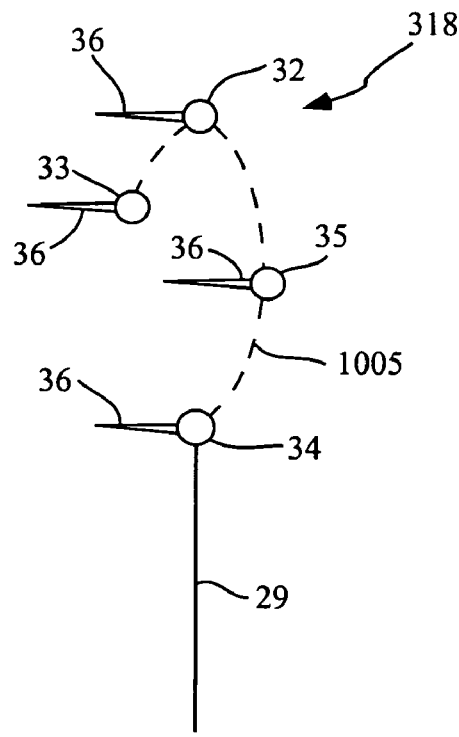

Looking now at FIG. 8a-8b, a non-continuous electrode array 318 is depicted. The non-continuous electrode array 318 of FIG. 8a-8b has been modified from the electrode array 310 of FIG. 3a-3c by not attaching electrodes in a complete circle, i.e. by substituting the insulated wire ring 1003 for a curved structure, or insulated wire "C" 1005. Shown are the electrode array 318; a wire bundle 29; the electrodes 32, 33, 34, and 35; fixation needles 36; and an insulated wire "C" 1005. The electrodes 32, 33, 34, and 35 are coupled together via the insulated wire "C" 1005. The fixation needles 36 are coupled to the electrodes 32, 33, 34, and 35. The needles 36 may or may not serve as part of the electrodes 32, 33, 34, and 35. The insulated wire may be flexible to allow any conformation of the insulated wire "C" 1005 and any relative position of the electrodes 32, 33, 34, and 35. For example, the electrodes 32, 33, 34, and 35 may be arranged in a partial circle or three-quarter circle (or "C"), as shown, a straight line or a line with a bend, such as a 90° bend, or the like, a complex curve, or the like. The non-continuous electrode array 318 of FIG. 8a-8b may be advantageously used when a tumor is awkwardly located or shaped, or difficult to surround with a ring of electrodes for any other reason. It is generally accepted that cancerous tumors should not be broken apart and, as such, a non-continuous electrode array 318 will allow flexibility in positioning.

Figure 9:
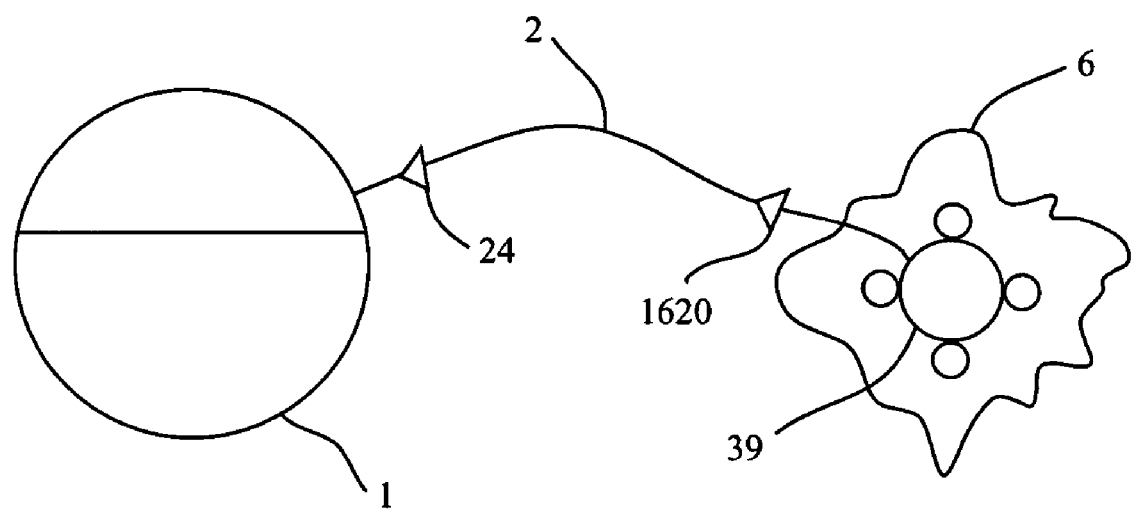
FIG. 9 is a diagram representing an example of an array of multiple electrodes on a lead comprising adapters that may be used with an electrical therapy system.

Referring now to FIG. 9, an electrode array 39 with lead adapters 24 and 1620 (such as shown above in FIG. 2f) is shown in connection with a tumor. Shown are a generator 1, a lead 2, a tumor 6, the lead adapters 24 and 1620, and a multiple electrode array 39. The electrode array 39 is electrically coupled to the generator 1. The multiple electrode array 39 may be placed on top of, around, and/or adjacent to the tumor 6. The multiple electrode array 39 may be anchored to the tumor 6 by any fixation means such as a needle, hook, barbed hook, "corkscrew", or any other suitable suture for mechanically securing the multiple electrode array 39 to the tumor 6 or to nearby tissue. Because the lead 2 and the multiple electrode array 39 together may be larger or bulkier than a single electrode lead, tunneling the lead to the tumor 6 may be problematic. To overcome this difficulty, the lead adapters 24 and 1620 may be used. The lead adapters 24 and 1620 are located at both ends of the lead 2 with lead adapter 24 lying closest to the generator 1 and the lead adapter 1620 lying closest to the electrode array 39. In this way, the multiple electrode array 39 can be placed on or proximate to the tumor 6 and connected to the generator 1 by way of the lead 2, which can be tunneled through tissue that may be interposed between a suitable implantation site for the generator 1 and the tumor 6, where the multiple electrode array 39 must be located.

As will be appreciated by one of ordinary skill in the art, many variations of electrode arrays may be used in electrical therapy. The examples described herein are by way of example and in no way limit the scope of the invention. Any combination of the numerous options described herein or otherwise suitable variations can be used to deliver electrical therapy.

For example, a non-continuous ring of electrodes may be used with an anchoring hook. In addition, two electrode arrays may branch from the same electrical connection on the generator 1 by way of, for example, a lead adapter. Therefore, any of a virtually infinite number of combinations of options, configurations, and features described herein are contemplated by the inventors.

Figure 10A:
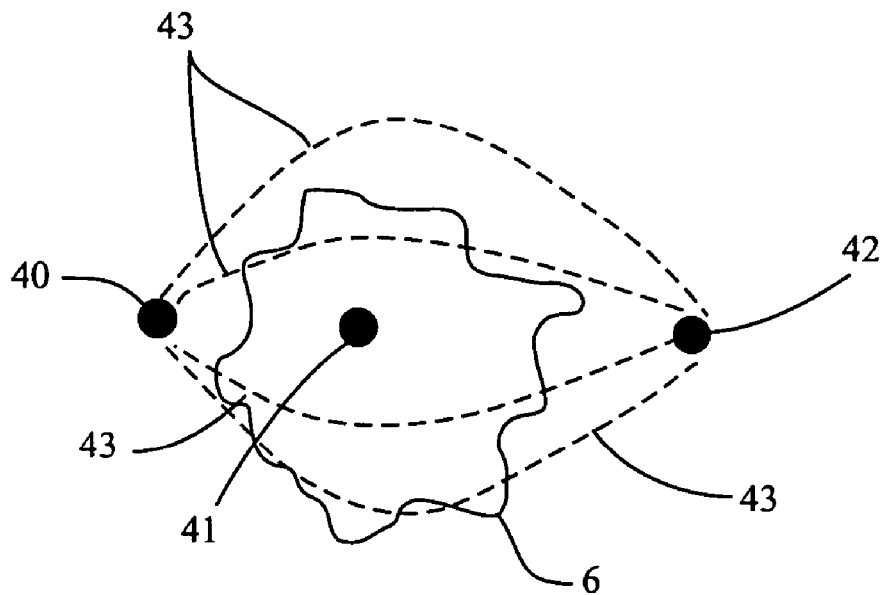
FIG. 10a-10b is an illustration depicting an example of an electrode arrangement which accommodates electrical therapy and electroporation such as may be employed in an electrical therapy system.
Figure 10B:
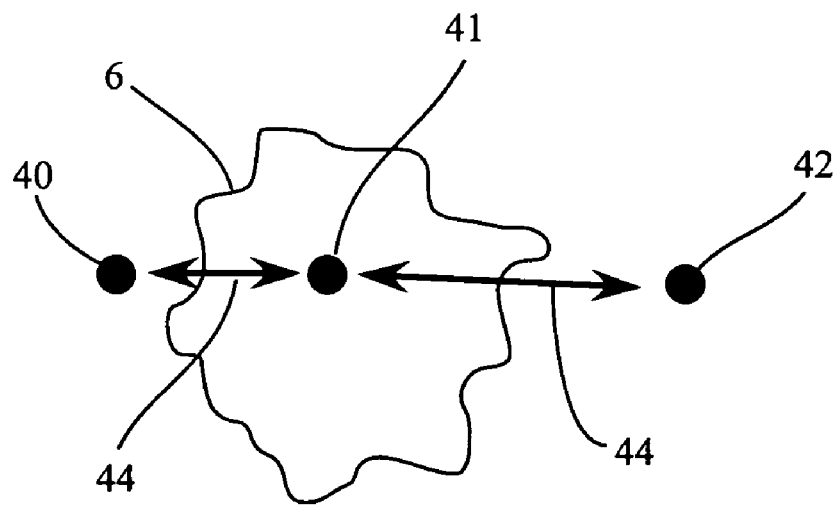

Shown in FIG. 10a-10b is an example of an electrode arrangement that accommodates electrical therapy and electroporation. Shown are a tumor 6; electrodes 40, 41, and 42; a DC ablation current 43; and an electroporation current 44. In this arrangement, three electrodes 40, 41, and 42 are placed in and around the tumor 6. The electrodes 40 and 42 lie at a periphery of the tumor 6 and the electrode 41 is placed at a center of, on top of, or below the tumor 6. By utilizing three electrodes, both DC ablation and electroporation can be performed. In a preferred embodiment, DC ablation current 43 occurs between the electrodes 40 and 42, as shown in FIG. 10a, and electroporation occurs between the electrodes 40 and 41, or between 41 and 42, as shown in FIG. 10b. Typically a set of electrode pairings having a greater interelectrode distance, such as between the electrodes 40 and 42, in comparison to electrodes 40 and 41, or 41 and 42, are used in electrical therapy to create the maximum electric field for encompassing large portions of a tumor, as shown in FIG. 10a. However, any combination of electrodes may be used for electrical therapy. Shown in FIG. 10b, two sets of electrode pairings with a smaller interelectrode distance may be optimally used for electroporation in order to increase the electric field intensity for a given pulse voltage amplitude. In a preferred embodiment, a chemotherapeutic agent may enter the electroporated area faster than cells in the surrounding area. The area between electrodes 40 and 41 and/or 41 and 42 will preferably consist of a large portion of the primary tumor whereas the area between the electrodes 40 and 42 might include metastases as well as the border of the primary tumor.

Figure 11:
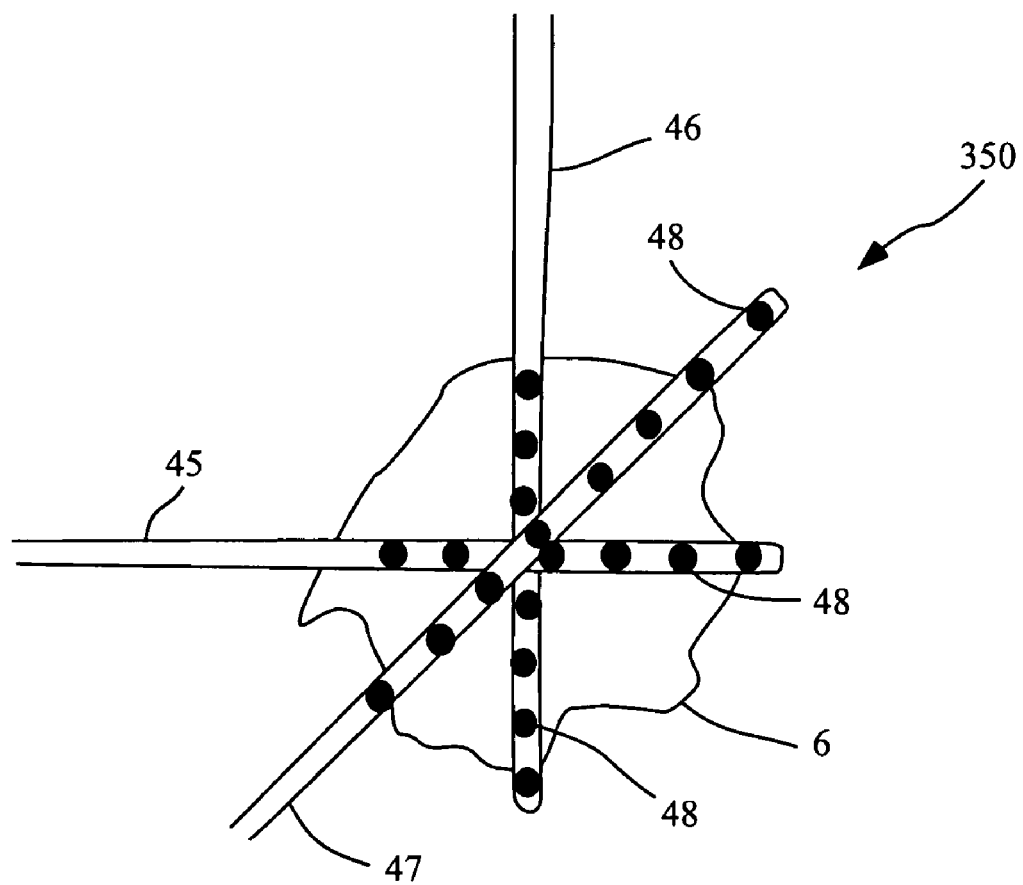
FIG. 11 is a drawing illustrating an example of three-axis electrode system such as may be employed in an electrical therapy system.

A three-axis electrode system 350 is shown in FIG. 11 and comprises a configuration of three leads 45, 46, and 47; multiple electrodes 48; and the three-axis system 350 for electrical therapy. The three-axis system 350 is electrically coupled to an internal and/or external power source (not shown). Each of the three leads 45, 46, and 47, which have a plurality of spaced apart electrodes 48 along a portion of their distal ends are implanted into a tumor 6 orthogonally and intersect near the center of the tumor 6. As the size, shape, density, and other characteristics of the tumor 6 change during application of electrical therapy, the central vector of current flow can be altered through selectively activating multiple electrodes 48 on the x, y, and z coordinates. In this way, the system can target the center of the tumor's mass. Additionally the system can selectively designate electrodes 48 as anodes or cathodes, or both anodes and cathodes in any sequence (such as using the hex bridge 300, such as shown in FIG. 2e-2f) and alter the 3-dimensional distribution of currents. The system can also pulse for more energy efficiency, such as by delivering one or more pulses of current between one or more pairs (or more) of the electrodes 48. In some cases it is more energy efficient to pulse at a low duty cycle than to maintain a steady current, even when the pulses may be at a higher voltage.

Figure 12A:
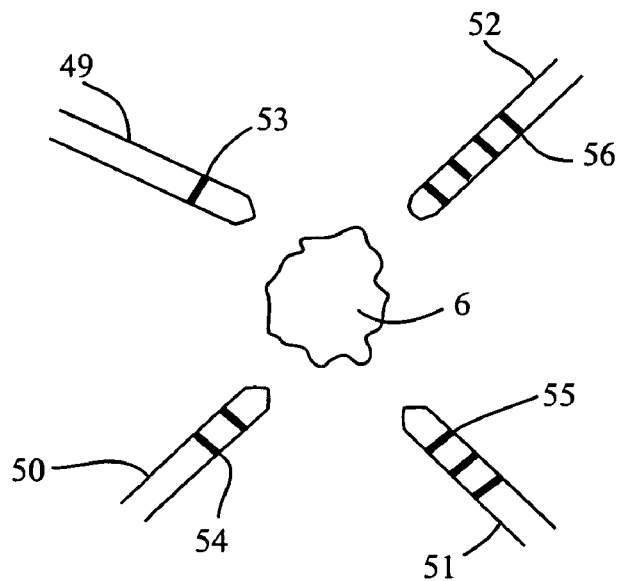
FIG. 12a-12b is a drawing depicting an example of a set of leads with unique identification markings that may be utilized with an electrical therapy system.
Figure 12B:
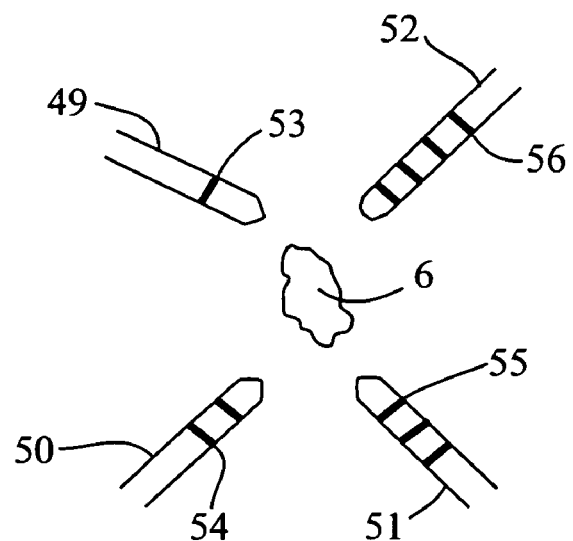

Turning now to FIG. 12a-12b leads 49, 50, 51, and 52 with unique identification marks 53, 54, 55, and 56 are illustrated. Shown are four leads 49, 50, 51, and 52; the unique markings 53, 54, 55, and 56; and a tumor 6. The leads 49, 50, 51, and 52 are electrically coupled to an internal and/or external power source (not shown). The leads 49, 50, 51, and 52 are coupled with any number and configuration of electrodes (not shown).

Each lead 49, 50, 51, and 52 is shown with its unique marking 53, 54, 55, and 56 respectively. The unique marking 53, 54, 55, and 56 is individually identifiable under imaging. The unique marking may be of a different material distinguishable from the lead material under imaging. By visually tracking the tumor 6 in relation to the leads 49, 50, 51, and 52, via their unique markings 53, 54, 55, and 56, during treatment, therapy can be reprogrammed, such as through transcutaneous telemetry, to deliver electrical therapy tailored to any changes in the tumor 6. For example, the leads and/or electrodes (not shown) may be shifted over time as the size, shape, or position of the tumor 6 changes. Referring to FIG. 12a, a set of four uniquely marked leads 49, 50, 51, and 52 surround the tumor 6. Then, in FIG. 12b, the same tumor 6 has changed size, shape, and position. In this case, based on the unique markings 53, 54, 55, and 56 of the leads 49, 50, 51, and 52, the leads 49, 50, 51, and 52 and/or electrodes (not shown) may be appropriately repositioned to target the center of the altered tumor. The markings may be a different number of stripes near the tip of each lead, such as shown in FIG. 12a-12b. However, any other type of unique marking that distinguishes one lead from another in the local tumor area may be used.

In another embodiment, imaging may also be accomplished by magnetic resonance imaging (MRI), computed tomography scan (CT), and ultrasound (echo imaging). The leads of the device may be adapted to withstand the radiation associated with MRI imaging by the addition of shunting and opening protection circuitry to prevent the induction of high currents through Faraday's law acting on the current loop of the electrodes. Alternatively, current loops may be generated from one wire and a return path through the tissue.

To enhance MRI and CT scanning, a contrast agent may be administered directly into the core of the tumor to be scanned. Alternatively, depending on the desired outcome of the MRI or CT scan, the contrast agent may be administered to the periphery of the tumor (i.e. in the vicinity of the tumor). The contrast agent may be injected with a needle or syringe, or it may be administered via any of the internal reservoirs and drug pumps described hereinbelow. The contrast agents may be for example, iodine compounds and solutions and charged micro spheres. Micro spheres are particularly advantageous in ultrasound imaging.

In another embodiment, the electrical therapy system may enhance imaging by applying current to increase the concentration of certain chemicals, such as oxygen. Oxygen concentration may be increased by forcing all electrodes anodal and/or by administering certain oxygenating substances, such as perfluorocarbons and/or any other oxygenators, such as, for example, any of the oxygenating substances described hereinbelow. Using this technique, the imaging device can read current distributions by back calculations from the oxygen and hydrogen concentrations, thereby rendering the tumor more visible.

Referring now to FIG. 13a-13e various types of lead anchoring mechanisms are illustrated. Shown are a tumor 6, a screw-in lead 57, a screw 58, pronged lead 59, two or more prongs 60, a telescoping lead 360, telescoping cylindrical electrode section 61, stationary electrode section 62, adjustable screw-in lead 1111, adjustable screw-in electrode 1113, adjusting means 1115, and rotatable coupling means 1117. Each of the leads 57, 59, 360, and 1111 is coupled to an internal and/or external power source (not shown).

Figure 13A:
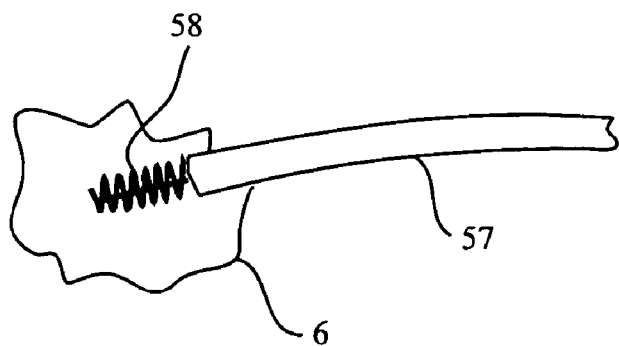
FIG. 13a-13e are drawings showing examples of lead anchoring systems such as may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.
Figure 13B:
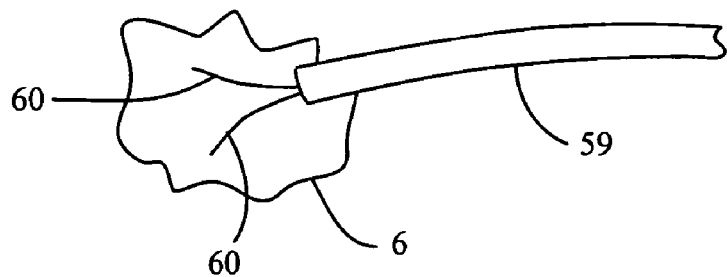
Figure 13C:
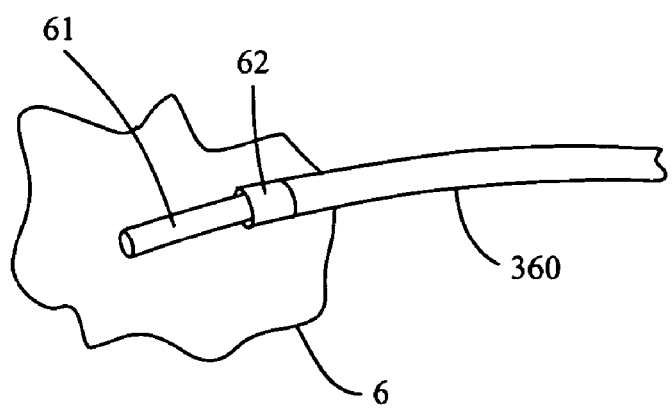

FIG. 13a shows the screw-in lead 57. Adapted with the screw 58, the screw-in lead 57 is designed to be left within a tumor 6 during therapy. Shown in FIG. 13b is the pronged lead 59 ending with two or more prongs 60, which are expanded into the tumor 6 during implantation and are left expanded throughout therapy. Depicted in FIG. 13c, is the telescoping lead 360. Shown are the telescoping lead 360 and one or more overlapping telescoping cylindrical electrode sections 61 and stationary electrode section 62, the telescoping cylindrical electrode section 61 has been extended from the stationary electrode section 62. The telescoping cylindrical electrode section 61 may be adjusted either pre- or postimplantation to an optimum length in order to anchor to the tumor 6 and create electrical contact therewith.

Figure 13D:
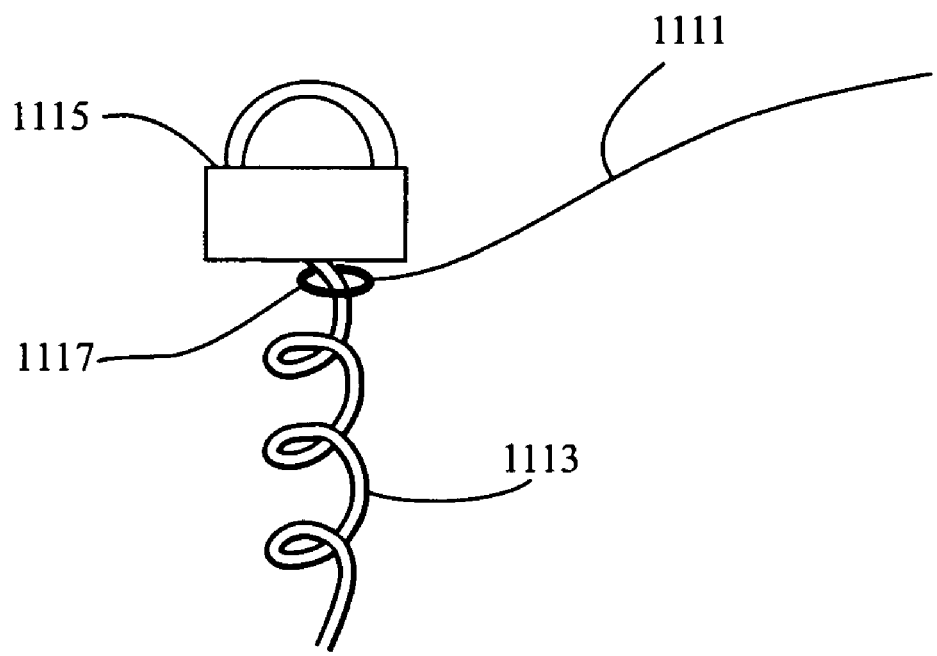
Figure 13E:
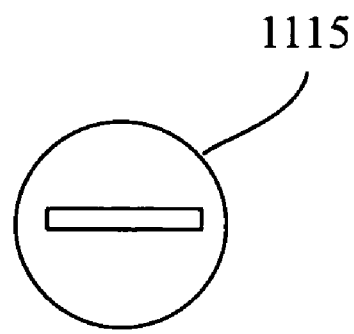

FIG. 13d depicts an adjustable screw-in lead 1111. The adjustable screw-in lead 1111 may be repositioned during electrical therapy as needed to "chase" a tumor. The adjustable screw-in lead 1111 is coupled at one end to a power source (not shown) such that the power source delivers electrical therapy to the adjustable screw-in lead 1111. At the other end, the adjustable screw-in lead 1111 is coupled with a rotatable coupling means 1117. The rotatable coupling means 1117 is electrically and mechanically coupled to an adjustable screw-in electrode 1113 such that the electrical therapy delivered by the power source (not shown), and carried by the adjustable screw-in lead 1111, is delivered to the screw-in electrode 1113 via the rotatable coupling means 1117. Rotatable coupling means 1117 may be, in one embodiment, a washer. The adjustable screw-in electrode 1113 may be in various sizes and lengths depending on the tumor characteristics (e.g. size, location, density, and composition). In a preferred embodiment, the adjustable fixation screw may be in the range of 0.2 to 2 inches in length and 0.1 to 1 inch in diameter. Coupled to the top of the adjustable screw-in electrode 1113 is an adjusting means 1115. Adjusting means 1115 allows the adjustable screw-in electrode 1113 to be easily inserted and removed from a tumor. Additionally, the adjusting means 1115 allows for easy repositioning during electrical therapy. Adjusting means 1115 may be designed with an elevated curve as shown. Alternatively, adjusting means 1115 may be shaped like a screw head or a bolt head. FIG. 13e is a top view of the adjusting means 1115.

Figure 14:
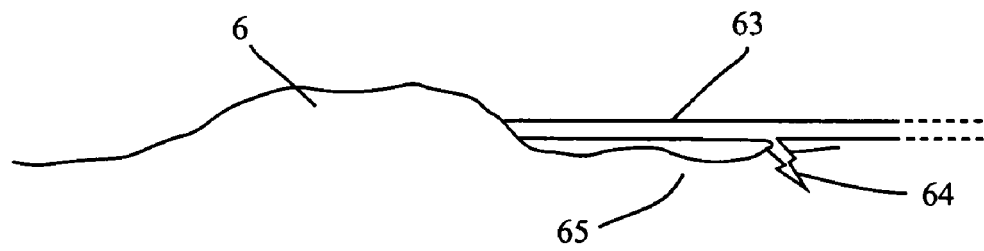
FIG. 14 is an illustration depicting an example of a fixation means for directly anchoring a lead to healthy tissue that may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.

Shown in FIG. 14 is a means for directly anchoring a lead to healthy tissue. Illustrated are a tumor 6, a lead 63, a fixation means 64, and healthy tissue 65. The lead 63 is coupled to an internal and/or external power source. The lead 63 may be coupled with any number and configuration of electrodes (not shown).

The lead 63 is shown inserted into the tumor 6. The lead 63 is held in position by means of a fixation device 64, which is directly anchored into the healthy tissue 65, which is peripheral to the tumor 6. Because tumor tissue may be soft and/or watery, a means for fixing a lead to nearby healthy, solid tissue, as shown, may be advantageous. In this case, the lead 63 remains fixed in place with no regard to any characteristics of the tumor 6. Additionally, as electrical therapy is applied, the tumor 6 may change size, shape, and density, thus anchoring the lead to healthy tissue may render readjusting the lead unnecessary. Fixation means may be a hook, needle, prongs, screw and any other device capable of anchoring a lead to healthy peripheral tissue.

Figure 15:
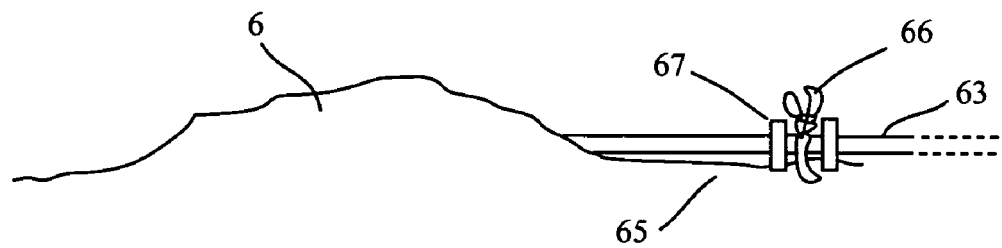
FIG. 15 is an illustration depicting an example of a fixation means for indirectly anchoring a lead to healthy tissue that may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.

Turning now to FIG. 15 a means for indirectly anchoring a lead to healthy tissue is illustrated. Shown are a tumor 6, a lead 63, healthy tissue 65, a suture 66, and a suture sleeve 67. The lead 63 is coupled with an internal and/or external source of power (not shown). The lead 63 may be coupled with any number and configuration of electrodes.

The lead 63 is shown inserted into a tumor 6. The lead 63 is held in position by means of the suture 66 in the suture sleeve 67. The suture 66 indirectly anchors the lead 63 into healthy tissue 65 peripheral to the tumor 6. Again, because tumor tissue may be soft and/or watery, a means for fixing a lead, either directly or indirectly, to nearby healthy solid tissue may be advantageous. In this case, despite any changes in size or composition occurring in the tumor 6, the lead 63 remains fixed in place. The lead 63 will remain in place regardless of changes occurring within the tumor 6.

The above illustrates only a few of the types of anchoring mechanisms possible for anchoring a lead to a tumor. The anchoring mechanisms may be of numerous shapes and sizes. Ideally, the anchoring mechanism is selected relative to the size, density, and location of the tumor in each circumstance. Importantly, tumor tissue, such as the tissue to which a lead of the present embodiment is anchored proximately, is quite different from heart muscle to which a pacemaker is anchored. Tumor tissue tends to be soft and retracting and, therefore, the anchoring device should permit penetration of this type of cancerous tissue while allowing safe removal. Anchoring leads of the present embodiment are akin to active fixation pacing leads rather than passive fixation leads. The anchoring mechanism may or may not also act as one or more of the electrodes. For example, in one embodiment, the anchoring means may double as the electrodes; both anode and cathode configurations are contemplated. Alternatively, the anchoring mechanism may not serve as an electrode, in which case the electrode may be at the end of the lead distal to the anchoring mechanism.

Figure 16:
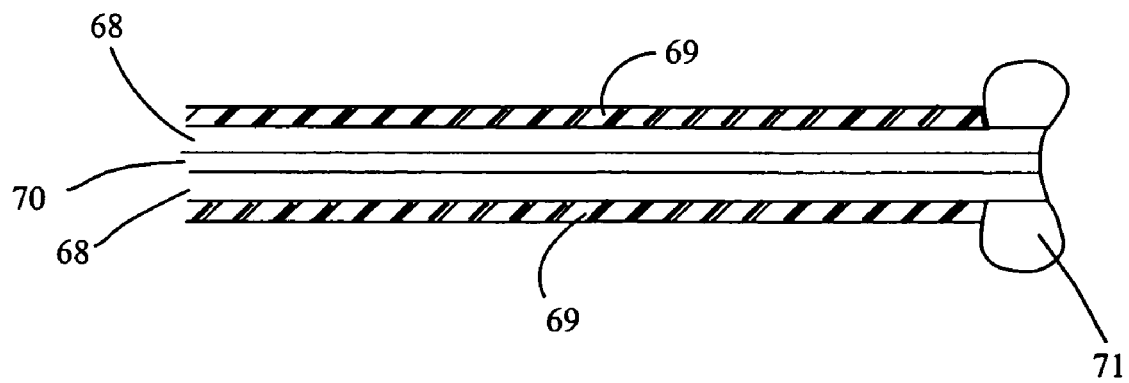
FIG. 16 is an illustration depicting an example of a lead with various options including a lumen, non-stick surface, and an inflatable balloon that may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.

The lead depicted in FIG. 16 has additional features and options that may be advantageous in certain circumstances. Shown are lead 68, a non-stick coating 69, a lumen 70, and an inflatable balloon 71. The lead 68 is coupled to an internal and/or external source of power (not shown). The lead 68 may be coupled with any number and configuration of electrodes (not shown).

The lead 68 of FIG. 16 features the non-stick coating 69 on an external surface of the lead 68. Additionally, the lumen 70 runs lengthwise along a distance of the lead 68. The inflatable balloon 71 is coupled to a distal end of the lead 68. The lumen 70, running the entire length of the lead 68, is useful for insertion, extraction, gas removal, and liquid removal. Because metabolic changes in a tumor may cause gas and liquid production, the lead 68, comprising the lumen 70 configured to remove both gases and liquids may be advantageous. During periods of high current injection, when gas and liquid production are likely to be greatest, gas and liquid removal may be particularly advantageous because excess gas and/or excess liquid may interfere with electrical therapy and/or cause bloating and/or pain.

In another embodiment, the lumen 70 may be completely open from end to end for a so-called "over the wire" insertion technique. Alternatively, the lumen 70 may be partially closed at a distal end, opposite the inflatable balloon 71, to block a stylet. The non-stick coating 69, which is applied to the outer surface of the lead 68, renders insertion and removal of the lead 68 easier. The inflatable balloon 71 is optionally coupled with the distal end of the lead 68 for securing the distal end of the lead 68 in a tumor. Additionally, the inflatable balloon 71 may be conductive such that by controlling the radius (through inflation or deflation) current density can also be regulated. Holes of any number, but preferentially two, may be associated with the distal end of the lumen 68 comprising the inflatable balloon 71 to allow for gas and liquid removal. However, the holes should be small enough to prevent a stylet from escaping. Any of the variations described herein may be used singly, together, or in any combination.

Figure 17:
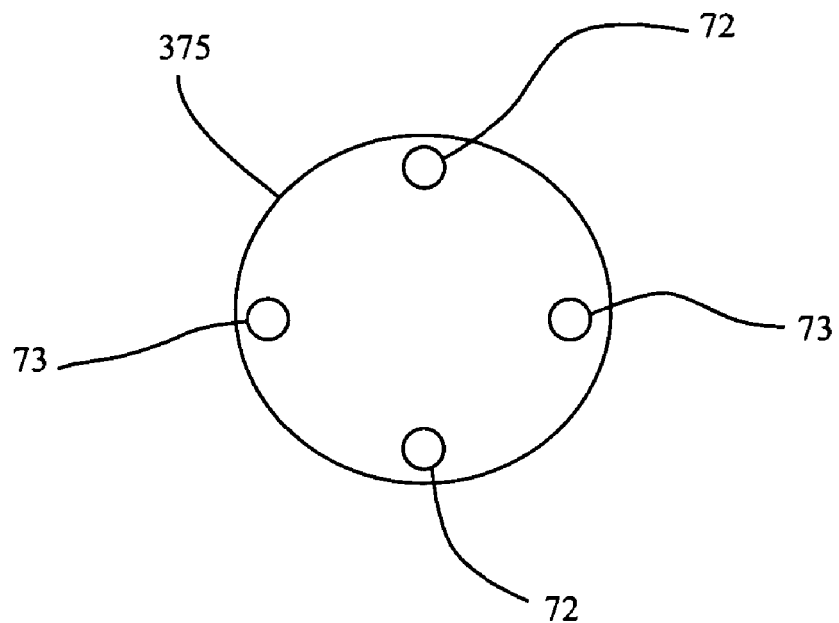
FIG. 17 is a drawing illustrating an example of a lead with various options including optical fibers and thermocouples that may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.
Figure 18:
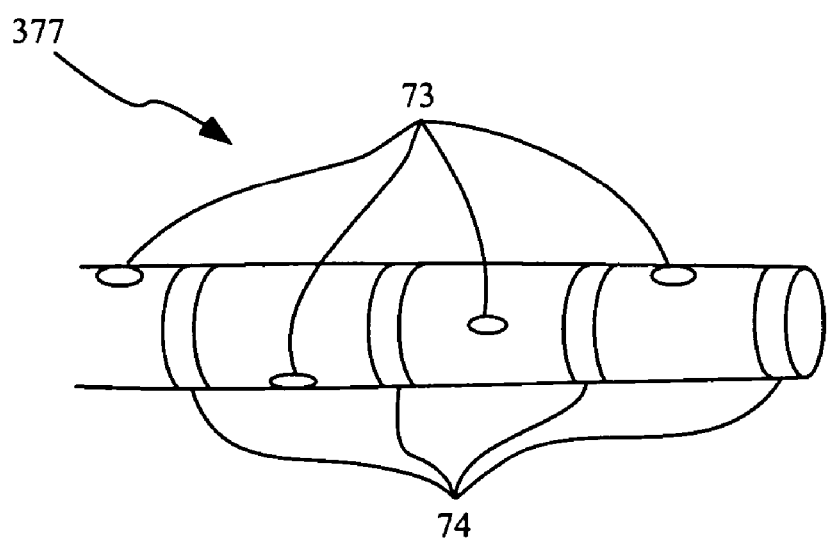
FIG. 18 is a drawing illustrating a side view of an example of a lead with thermocouples that may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.

Referring to FIG. 17-18 additional features and options that may be advantageous in various circumstances are depicted. Shown features include optical fibers 72, temperature sensors 73, electrodes 74, and leads 375 and 377. The leads 375 and 377 are coupled to an internal and/or external source of power. Furthermore, the leads 375 and 377 may be coupled with any number and configuration of electrodes.

FIG. 17 shows a distal end of a lead 375 comprising the ends of each of two optical fibers 72 and two temperature sensors 73. The optical fibers 72 allow for visualization under acute imaging. Acute imaging can be accomplished indirectly by using a Charge Coupled Device (CCD) inside a generator (not shown, but such as in FIG. 1) for imaging tumor regression or chemical sensing. For example, the absorption or transmission of various infrared light frequencies by blood is strongly influenced by a level of oxygen saturation. Therefore, optical fibers 72 may be useful for monitoring oxygen levels, by delivering light through one fiber and then monitoring the transmitted light through the other fiber. Temperature sensors 73 are also coupled to the end of a lead to allow monitoring of the temperature in and around a tumor. Temperature sensors 73 may be of any variety such as thermistor and thermocouple temperature sensors. As tumors tend to have an elevated temperature in comparison to healthy body tissues, the progression or regression of a tumor can be monitored by monitoring variations in temperature at or near the electrodes over time (excluding localized heating that may briefly accompany electrical therapy). In another embodiment, the temperature sensors 73 may be placed on the sides of the lead or a catheter such as shown in FIG. 18. Shown in FIG. 18, temperature sensors 73 are placed along lead 377 to allow for temperature-monitoring at various positions within the tumor.

In another embodiment, the tip electrodes and one or more ring electrodes on the lead and/or the catheter may be roughened by, for example, sandblasting, chemical surface modulation, physical surface modulation, or any other means of modification in order to produce a high microscopic surface area to minimize polarization and corrosion.

Figure 19A:
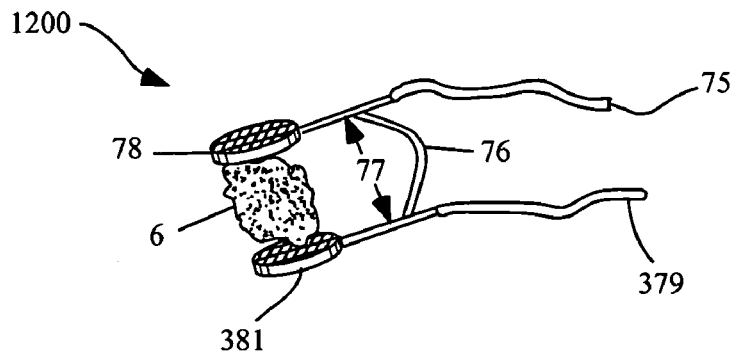
FIG. 19a-19c is a drawing showing several examples of a lead modified for measuring capacitance and resistance that may be used with any of the leads described in FIG. 2a-2d, FIG. 2g, FIG. 3a-3c, FIG. 4, FIG. 5a-5b, FIG. 6a-6b, FIG. 7a-7b, FIG. 8a-8b, FIG. 9, FIG. 11, and FIG. 12a-12b.
Figure 19B:
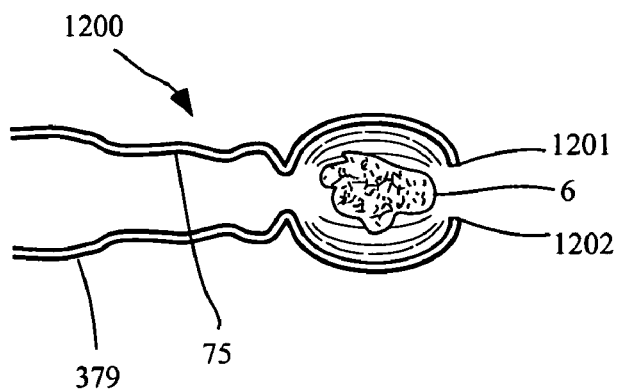
Figure 19C:
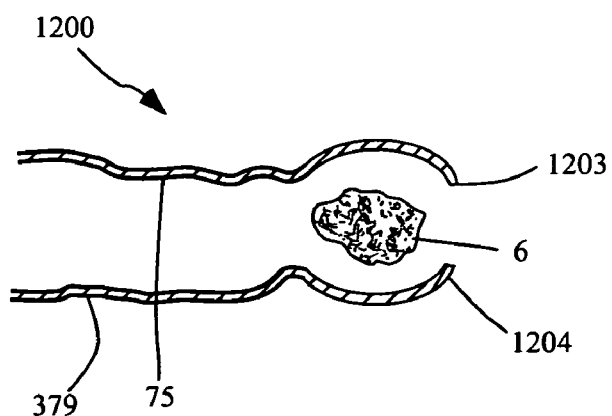

Depicted in FIG. 19a-19c is a dielectric sensor 1200 for measuring capacitance and reistance. Shown are two leads 75 and 379, a spacer 76, a fixed distance 77, cylindrical electrodes 78 and 381, spherical electrodes 1202 and 1204, and a tumor 6. The leads 75 and 379 are coupled to an internal and/or external source of power (not shown).

Turning to FIG. 19a, leads 75 and 379 are coupled to cylindrical electrodes 78 and 381, which are held at the fixed distance 77 by the spacer 76. The spacer 76 holds the electrodes 78 and 381 at the fixed distance 77 ensuring that the electrodes do not migrate during the course of therapy. The resulting non-migrating or rigid structure should cover a maximum area of the tumor 6. In this arrangement, the electrodes 78 and 381 are used to deliver electrical therapy to tumor 6, but may also serve as a capacitor with the tumor as a dielectric, allowing for the measurement of the capacitance and resistance of the tumor 6. These values can be used to measure necrosis, tumor size, tumor density, and other characteristics.

Shown in FIG. 19b-19c, leads 75 and 379 are coupled to spherical electrodes 1202 and 1204. Leads 75 and 379 are coupled at one end to a power source (not shown) such that the leads 75 and 379 may deliver electrical therapy to spherical electrodes 1202 and 1204. Spherical electrodes 1202 and 1204 are designed to "cup" or surround the tumor 6 in order to measure capacitance and resistance of the tumor 6 and/or deliver electrical therapy. FIG. 19c is a cross-sectional view of FIG. 19b.

Because tumors vary in both shape and size, or may change shape and size during the process of electrical therapy, it is envisioned that different sizes and shapes of electrodes, such as the cylindrical electrodes 78 and 381 (as shown in FIG. 19a) and the spherical electrodes 1202 and 1204 (as shown in FIG. 19b-19c), may be used to maximize tumor surface area exposed to the electrical field. Additionally, because tumors may vary in size, it is envisioned that the spacer 76 may be adjusted appropriately to accommodate a tumor of any size.

Figure 20:
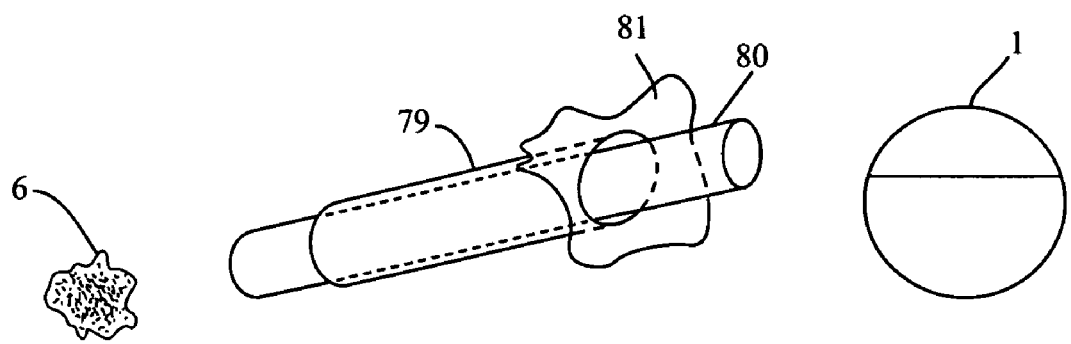
FIG. 20-21 are representations of an example of a method and device for creating a conduit for leads to pass through to a tumor for use in electrical therapy systems.
Figure 21:
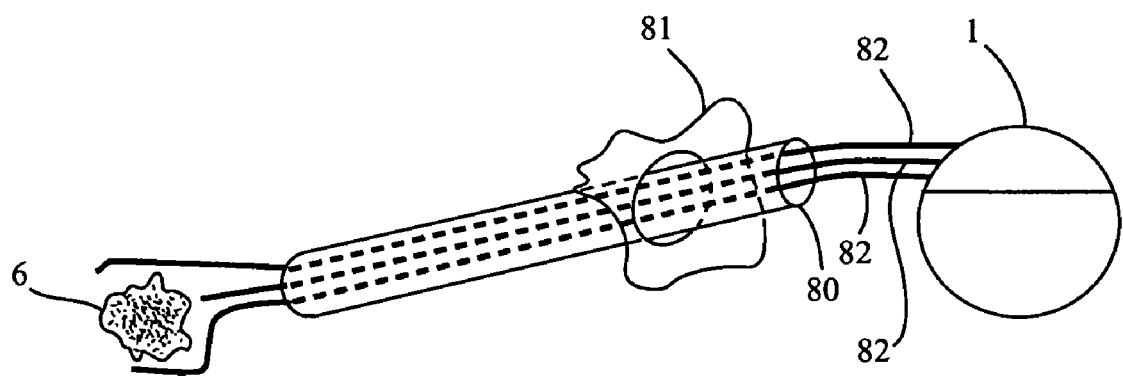

Represented in FIG. 20-21 is a method and device for creating a conduit for leads to pass through tissue to a tumor. Shown are a generator 1, a tumor 6, a tunnel 79, a conduit 80, surrounding tissue 81, and leads 82. The leads 82 are coupled to generator 1.

A trocar or other surgical tool is used to create the tunnel 79 through surrounding tissue 81. The conduit 80 is then passed through the tunnel 79. Looking to FIG. 21, the leads 82 attached at proximal ends to the generator 1 can be easily fed through the conduit 80 to the tumor 6. Following therapy, the leads 82 can be easily extracted through the conduit 80. The conduit 80 can be made of various materials including inert and/or non-reactive metals, such as platinum and stainless steel. In a preferred embodiment, the conduit 80 is made of absorbable material which the body can safely dissolve over time. In the case of non-absorbable conduits, the conduit 80 should be removed from a patient's body when the leads 82 are removed.

The leads contemplated in variations of the present embodiment may be coupled either permanently or detachably to a generator or other power source (internal and/or external). Each particular situation will determine the need for a permanently coupled system versus a detachably coupled system. For example, depending on the desired cost versus system flexibility, a permanent or detachable system may be desired. A low cost system could employ leads of fixed length and optionally means for anchoring the leads to the tissue. In the low cost system, the leads are permanently attached to the generator.

The leads and the electrodes of the device may be comprised of platinum or other noble metal, and alloys thereof. For example, the electrodes of the present embodiment may be made of a few strands of platinum iridium coated with insulation. Furthermore, the leads and the electrodes of the present embodiment may be formed of high-strength, non-reactive metals, such as titanium and stainless steel. The leads and the electrodes made of conductive oxides and semiconductors can also be used. Additionally, any metal used in implantable pacemakers may also be used in the device of the present embodiment. Unlike pacemakers, however, there will generally be no need for sophisticated non-polarizable electrodes in the device of the present embodiment.

Determining the type of material which a lead should be made of may be case specific. A material's expense, strength, and flexibility should be considered. Depending on the severity of a case and location of a tumor, strength and flexibility of a material may make one type of metal a better choice than another. For example, the major stress placed on the lead is generally during implantation, in which case the lead's strength should be a compromise between reducing the diameter and being able to withstand kinking during implant. Alternatively, a tumor located in an active part of the body, such as a sarcoma in the arm or leg, may experience more stress after implantation, in which case a lead with a larger diameter or a material of greater strength should be used.

The leads of the present embodiment may be supplied in various lengths or in a single length, with excess lead being wrapped around the generator housing.

A lumen or stylet aperture is optional.

3. Generator

Figure 22:
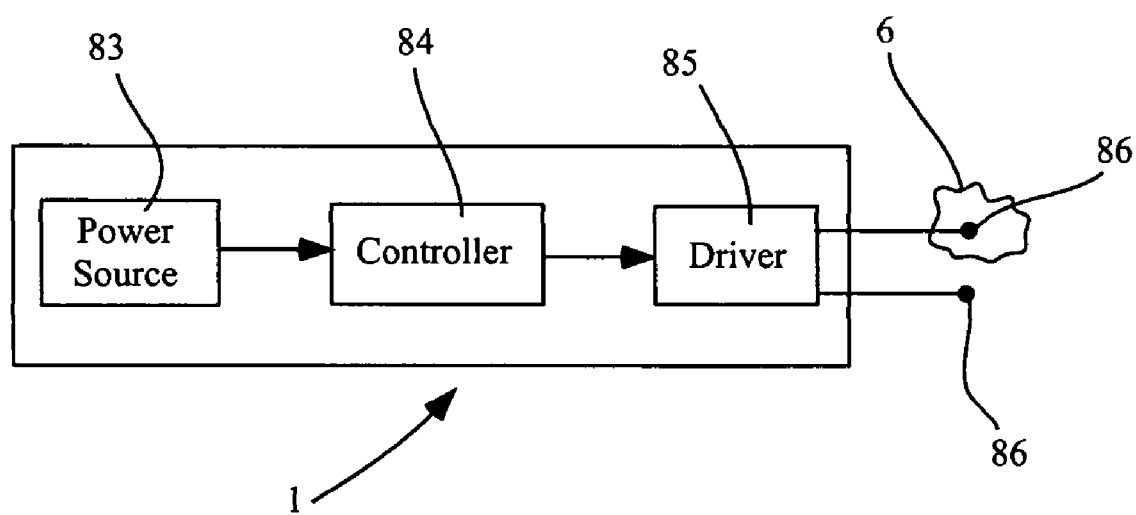
FIG. 22 is a block representation of an exemplary basic generator such as may be utilized in an electrical therapy system.

Looking now at FIG. 22 a block diagram of a basic generator 1 of the present embodiment is depicted. Shown are the generator 1, a tumor 6, a power source 83, a controller 84, a driver 85, and lead electrodes 86.

In the generator 1 of FIG. 22, the power source 83 is coupled to the controller 84 which is coupled to the driver 85. In turn, the driver 85 is coupled to the lead electrodes 86. The power source 83 may be a primary battery, a rechargeable battery, or a receiver of radio frequency (RF) or inductive energy coupled from outside the body.

In a preferred embodiment, battery voltage is available to the driver 85, which provides electrical therapy to the lead electrodes 86. In a preferred embodiment, direct current is provided to the lead electrodes 86. The controller 84 permits the voltage/current/coulombs to be turned on or off and may consist of a magnetic reed switch activated by an external permanent magnet. The driver circuit 85 delivers regulated voltage or constant current to the electrodes 86 to compensate for changes in impedance seen at the electrodes 86. Alternatively, electrical therapy may be delivered to a patient via total amount of coulombs.

Figure 23:
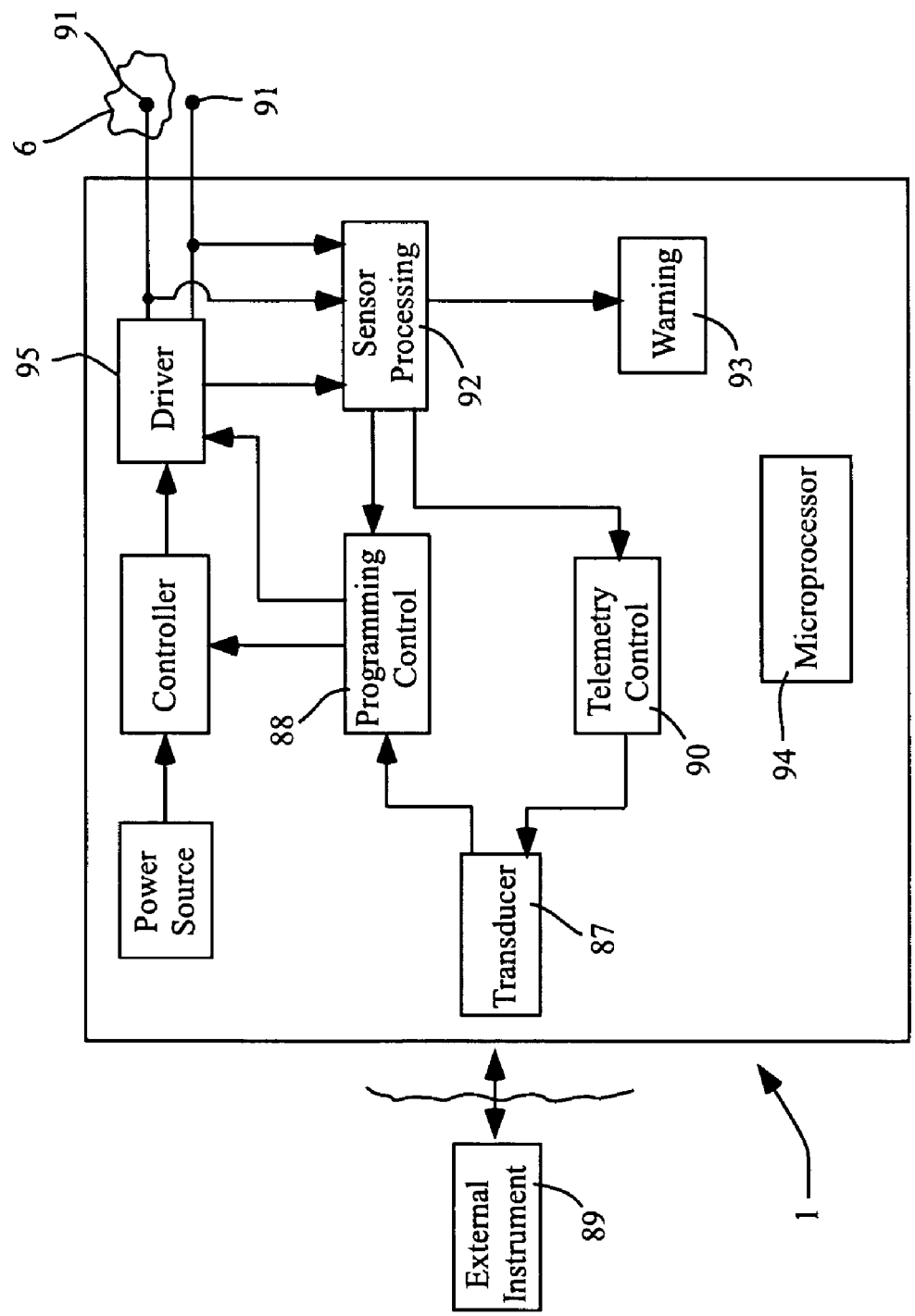
FIG. 23 is a block representation of an exemplary advanced generator such as may be utilized in an electrical therapy system.

Shown in FIG. 23 is a block diagram of an enhanced generator 1 of the present embodiment in which many parameters can be programmed, such as voltage amplitude, current amplitude, output polarity (to switch anodes and cathodes), and total number of coulombs to be delivered to the electrodes. The generator 1 of FIG. 23 comprises a transducer 87, a controller 88, an external instrument 89, a telemetry circuit 90, electrodes 91, a sensor processor 92, a warning signal 93, a microprocessor 94, and a driver 95. Commands may be transmitted by the external instrument 89 to the transducer 87 and the controller 88. The telemetry circuit 90 permits data to be transmitted to the external instrument 89. Perceived data may include battery life remaining, coulombs delivered, and sensor information from a tumor 6, such as tumor size, density, or chemistry data (e.g. pH). Other embodiments include pressure measurements as the tumor 6 shrinks or grows, an index of tumor regression or proliferation, and an electrode displacement indication. This type of information can be detected by the electrodes 91 and specialized sensors such as physical, impedance, pressure, optical, and chemical sensors. Sensors can be designed to tolerate radiation ionization if radiation therapy is probable. Sensed information is processed at the sensor processor 92 and can be telemetered by the telemetry circuit 90 to the external instrument 89 via the transducer 87 and may be used to control the generator 1 directly. For example, sensing of excessive heating or gas buildup can cause the therapy to be halted until the tissue cools or the gas is reabsorbed. Other features of the generator may include defibrillation protection, a controller 88 adapted to gradually increase voltage at the start of treatment, a programmable timer to control duration of therapy and sequence of therapy, and the warning signal 93, which can be audible or vibration, to the patient to signal battery depletion, an open or short circuit, and other conditions warranting attention. The entire device is preferably under control of the microprocessor 94, although its simplicity may not require computer control. The driver 95 may have several sections, each suitable for a different therapy depending on the voltage and current levels required. Preferably, the driver includes the hex driver of FIG. 2e-2f. Portions of the entire device may be operated in a "sleep" mode to conserve energy when not in use.

The sensor processor 92 is preferably a direct current amplifier which detects intrinsic body currents. The generator 1 can begin the therapy process by "priming the pump" with a short duration direct current which helps the body initiate its own therapeutic currents. Output current levels may be either programmed or adjusted automatically to optimum levels to minimize tumor cell proliferation.

In another embodiment, the external instrument 89 may communicate with the implanted electrical therapy device. Among the many advantages of this particular conformation, this variation will allow for testing of the implanted leads prior to unsealing the sterile implantable device from its packaging. The sterile electrical therapy device may have short electrode jumpers extending out from the connection head to allow for temporary connections (in application, the leads are inserted into or near to tumors during surgery). The outside box holding the implantable device may be "jumped" to previously implanted electrodes. A programmer may then communicate with the unopened (sterile) device in order to verify appropriate positioning of the electrode leads 91.

The programmer may also display various data including the waveforms of impedance, voltage/current/coulombs, and pH in and around the tumor(s), which may be downloaded into the programmer from the implantable device. These data or "oncogram" information are valuable in tracking the patient's prognosis. For example, voltage and current are correlated with malignant activity, impedance and pH are related to the progression or regression of malignancies, and the impedance spectrum (i.e. the Z(f)) which is the impedance across the tumor at various frequencies, will allows estimation of tumor size.

Various parameters, such as, for example, impedance, voltage/current, pH, oxygen, and temperature may be stored long term using analog to digital conversion and compression. Alternatively, the device may use a delta modulation scheme or store voltages/current directly onto a charge storage device such as a capacitor array or one or more gates of complementary metal oxide semiconductor devices.

Waveform morphology may be controlled by one or more parameters entered into the programmer thereby allowing storage of the exact desired wave shape that may be advantageously used until the patient's next clinical exam.

The programmer may also administer and control instantaneous voltages and currents for testing and shorter-term therapy. For example, it may be desirable to deliver the first hour of therapy such that extreme pH changes are accomplished (this may be done for example at a clinic). Because extreme pH changes are generally associated with higher levels of electrical therapy, this step may be advantageously accomplished via an external power source thereby reducing current drain on the implanted device battery. Furthermore, early monitoring of the tumor response may be available because the initial therapy may take place in a clinic (or other medical facility).

Furthermore, the programmer may also accept data from other sources. For example, an MRI or CT scan may locate a tumor and approximate size (as described hereinabove) and input the data to the programmer. By inputting such information, the programmer may select or recommend various parameters such as waveform, voltage, current, and time durations to optimize electrical therapy. The programmer may send a simplified outline of the tumor and electrode positions to the implanted device for storage. The stored information and images may then be referred to as a reference point.

The programmer may be based on any of a personal digital assistant (PDA), tabletop computer, and laptop computer. Communication between the programmer and the device may be via, for example, RF, magnetic wireless telemetry, and/or any other of the communication methods described herein. The implantable device may store many parameters in addition to "oncograms" such as, battery internal resistance, unloaded and loaded voltages, output therapeutic currents, therapeutic voltages, stored therapeutic waveforms, and data obtained from additional sensors supported by the implanted device.

The programmer may send commands to change waveform morphology, enable and disable the programming functions, and interrupt or tune the closed loop control (as described hereinbelow). Additionally, the programmer may enable a sensor driven open loop function (the transfer function may be linear or non-linear).

In another embodiment, the programmer may download whole waveform descriptors. The descriptors may be abbreviated mathematical descriptors or continuous analog-like descriptors such as an MIDI file or an MP3 file.

The device of FIG. 23 may be controlled by a magnet or a patient notification device. The magnet may be used by a patient or health care practitioner to turn off therapy or to provide other controlling signals to the implantable device by placing the magnet in the proximity of the implanted device. This procedure may be performed if a patient feels that the therapy is too painful, is concerned for other reasons, or is providing some additional control inputs to the implanted device.

The patient-controller can be used by the patient with very simple commands to make modifications to therapy. Patients can increase the current of the therapy. Alternatively, if the increased current is causing too much pain then the patient can reduce the current temporarily until the next follow-up visit. Further, the patient can increase the level of TENS (transcutaneous electrical nerve stimulation) to optimize the blocking of pain. This TENS stimulation is generated by the implanted device. Also, the patient can increase the level of drug infusion (as described hereinbelow).

The patient can also command the device to go into a nocturnal mode. While in nocturnal mode the device will deliver high current therapy only during the night when the patient is less likely to be sensitive to internal pain. Alternatively, the patient may request a circadian rhythm approach. During a circadian rhythm cycle critical high-current therapies are administered during the best times of day for the patient's type of cancer. This method is advantageous because, as known by those of ordinary skill in the art, different types of cancer respond to chemotherapeutic agents much better at different times of day. Other options include a push button indicating the presence or absence of pain and a number correlating to the pain level. Additionally, the patient may have access to a medication button showing when medications and/or meals were taken. These data may be stored in the implanted device or the external patient control unit for later downloading.

The device may also generate an audible or electrical stimulation reminding the patient to take their medications and to eat. The device may also generate a warning signal (audible or electrical stimulation) if the patient does not take their medication or meals within a certain time frame.

Low battery condition may also alert the patient with an appropriate tone. This tone signifies to the patient that they must go into the clinic to have the device recharged or replaced depending upon the model. The patient control unit may communicate to the device to verify that the device is on to reassure the patient. The patient can also be alerted to lead breakage or other electrode contact problems so that he/she can return to the clinic to have the problem checked.

The system may alert the patient through a device signal and/or through the patient control that the appropriate therapeutic goal has been achieved. This signal may signify that a certain pH has been attained for a given length of time or that by sensed oxygen level and/or temperature level that the tumor appears to have shrunk significantly. These conditions may indicate to the patient that they should return to their clinic for a follow-up exam.

Figure 24:
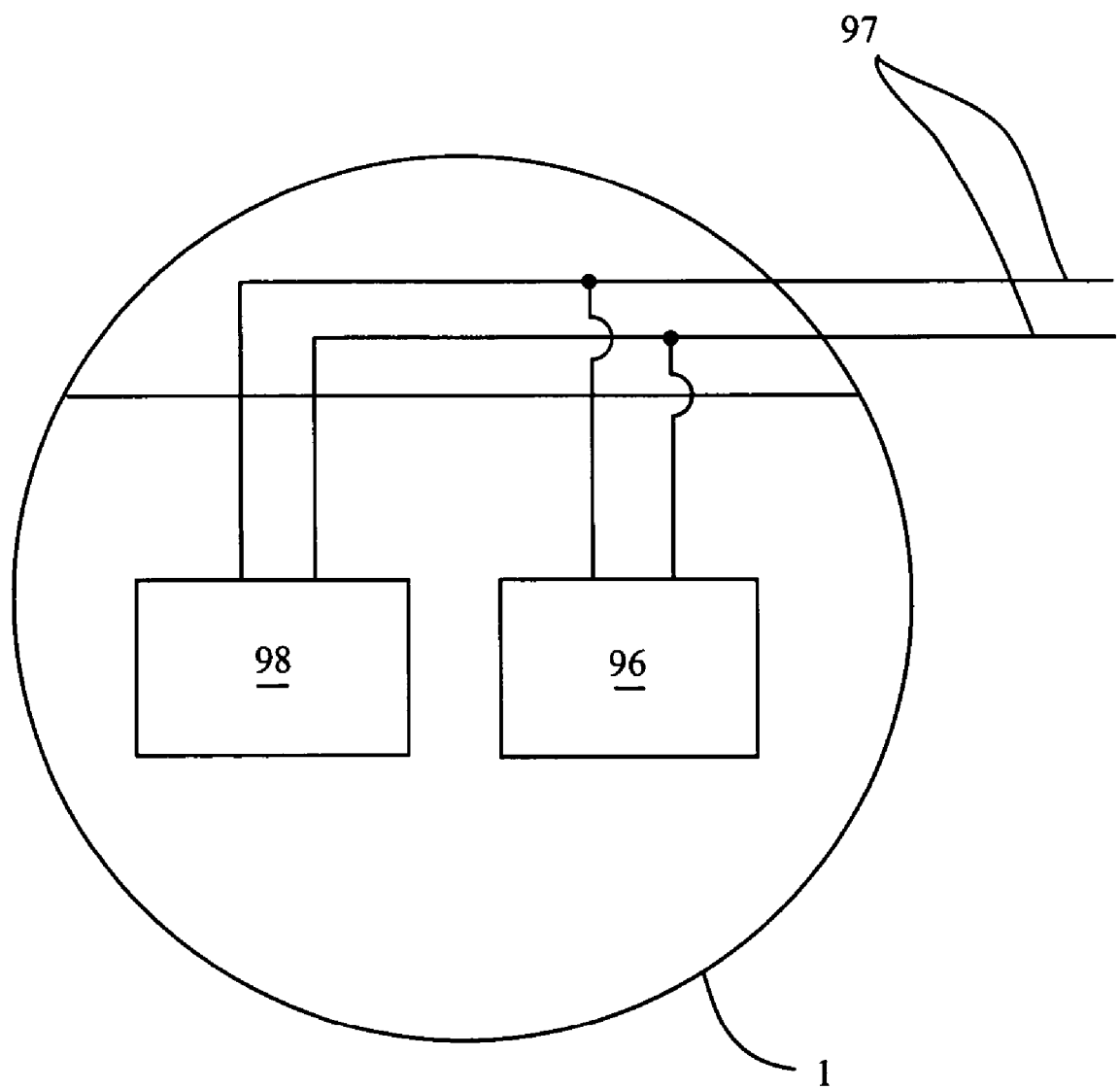
FIG. 24 is a block representation of an exemplary generator comprising a port such as may be utilized in an electrical therapy system.

Shown in FIG. 24 is a generator comprising a port. Shown are a port 96, leads 97, drive circuits 98, and a generator 1. The port 96 is built into the generator 1 electrically between the drive circuits 98 and the leads 97. The port 96 can accept electrical input from a source other than the generator 1. In a preferred embodiment, the electrical source is located outside the body. The location of the port 96, between the drive circuits 98 and the leads 97, allows electrical input from a source other than the generator 1 to be directly connected to the leads 97. The port 96, positioned as such is useful to modify electrical therapy as needed from an outside source. Modified electrical therapy may be in the form of electroporation therapy with or without additional chemotherapy, specialized electrical therapy regimens, and electrical programs otherwise altered from an internal system.

Figure 25:
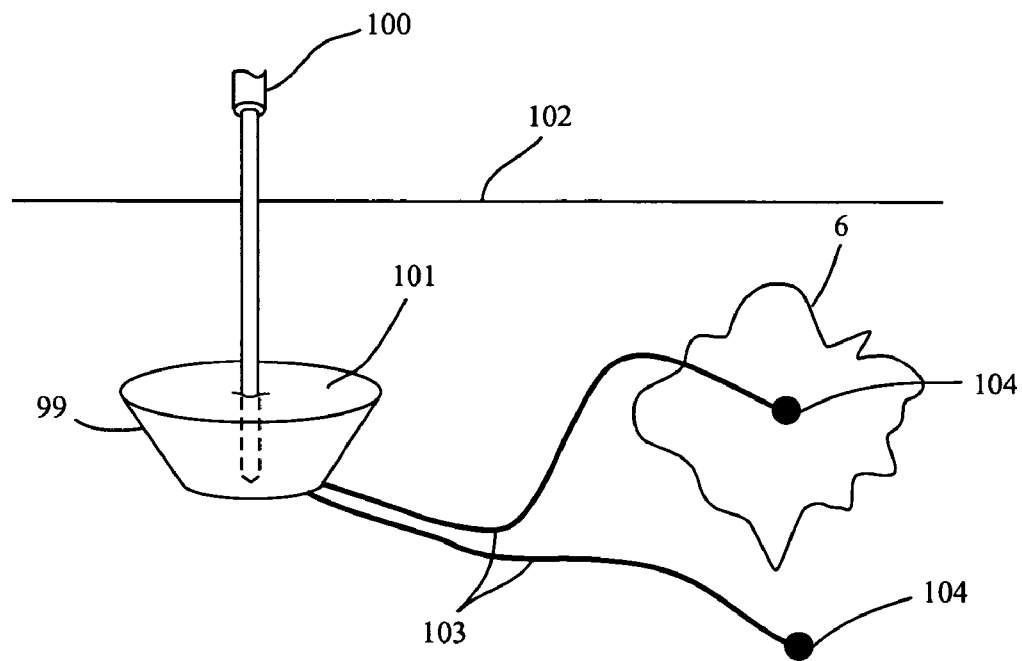
FIG. 25 is an illustration depicting an example of a port for use in an electrical therapy system.

Illustrated in FIG. 25 is an example of a port for use in electrical therapy. Shown are a port 99, a conducting needle 100, a self-sealing diaphragm 101, skin 102, a tumor 6, leads 103, and electrodes 104. The port 99 is implanted below the skin layer 102. The port 99 is coupled to the leads 103. At the distal end of leads 103, opposite the port 99, are the electrodes 104. The electrodes 104 are positioned in or around the tumor 6. The conducting needle 100 can be inserted into the port 99 through the self-sealing diaphragm 101 to make an electrical connection to the leads 103. The self-sealing diaphragm 101 can be made of any type of material useful for excluding body fluid. In a preferred embodiment the self-sealing diaphragm is made of silicone. In another preferred embodiment, the conducting needle 100 is coupled to an external electrical source such as an external generator (not shown). In this way, the external generator can make a direct electrical connection to the leads 103 and the electrode 104 via port 99. However, the leads 103 may additionally be coupled to an internal power source (not shown). The conducting needle 100 can be any useful for cleanly penetrating self-sealing diaphragm 101. In a preferred embodiment, a Huber point needle may be used.

The port 99 can be used in electrical therapy systems with or without an implanted generator and with or without an external electrical source. For example, means of powering an electrical therapy system of the preferred embodiment may comprise an implanted system which is powered solely by an external source when coupled to the internal electrical therapy system counterpart; the external power source may be coupled to the internal counterpart by a port as described in FIG. 25 or any other means useful for powering the internal electrical therapy system. Alternatively, the electrical therapy system of the preferred embodiment may be powered by an internal electrical source until such time an external power source is coupled to the internal electrical therapy system in such a way as to bypass the internal power source, such a port as described in FIG. 25. The previous examples are for illustration purposes only and are in no way limiting to the numerous ways an external power source may be coupled to an internal electrical therapy system.

Figure 26:
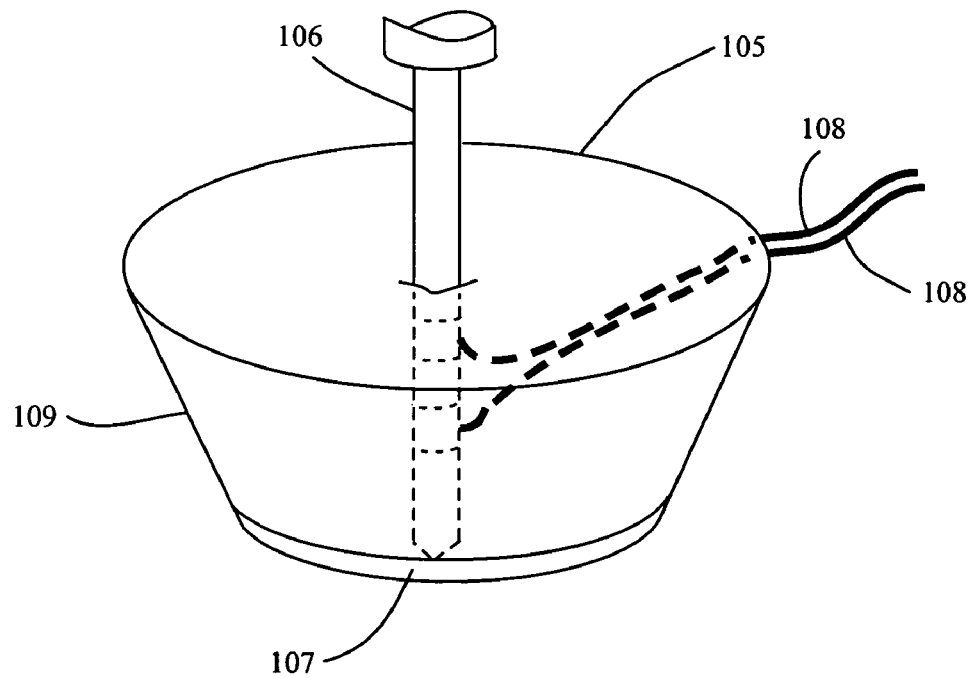
FIG. 26 is an up close diagram of a needle inserted into a port during electrical therapy.

Turning now to FIG. 26 an up close diagram of a conducting needle 106 inserted into a port 109 is depicted. Shown are a diaphragm 105, a conducting needle 106, a needle stop 107, lead ends 108, and a port 109. The conducting needle 106 is shown inserted into the port 109. The needle stop 107 prevents the conducting needle 106 from puncturing the bottom of the port 109. Additionally, the needle stop 107 may serve as a positioning guide for correctly inserting the conducting needle 106 into the port 109. As inserted into the port 109, the conducting needle 106 completes an electrical circuit between an electrical source and the leads 108 which are connected to the electrodes. The electrical source may be an implanted generator or external generator. In a preferred embodiment, the electrical source is an external generator. Needle contact may be electrically checked by measuring impedance between electrodes or of a resistor temporarily placed across the output. It is envisioned that by including a port, short in-patient sessions of electroporation and/or high current/voltage DC ablation may be provided by an outside electrical source while consistent or long term electrical therapy may be achieved by an implanted electrical source. Advantageously, by eliminating electroporation generating means from an internal generator, need for high voltage generation circuitry and high power supply is reduced; thereby reducing the cost and size of the device. According to this embodiment, electroporation may be used with or without chemotherapy. However, both electroporation and electrical therapy could be provided internally as well as externally from the same electrical source.

4. Method of the Preferred Embodiments

Figure 27A:
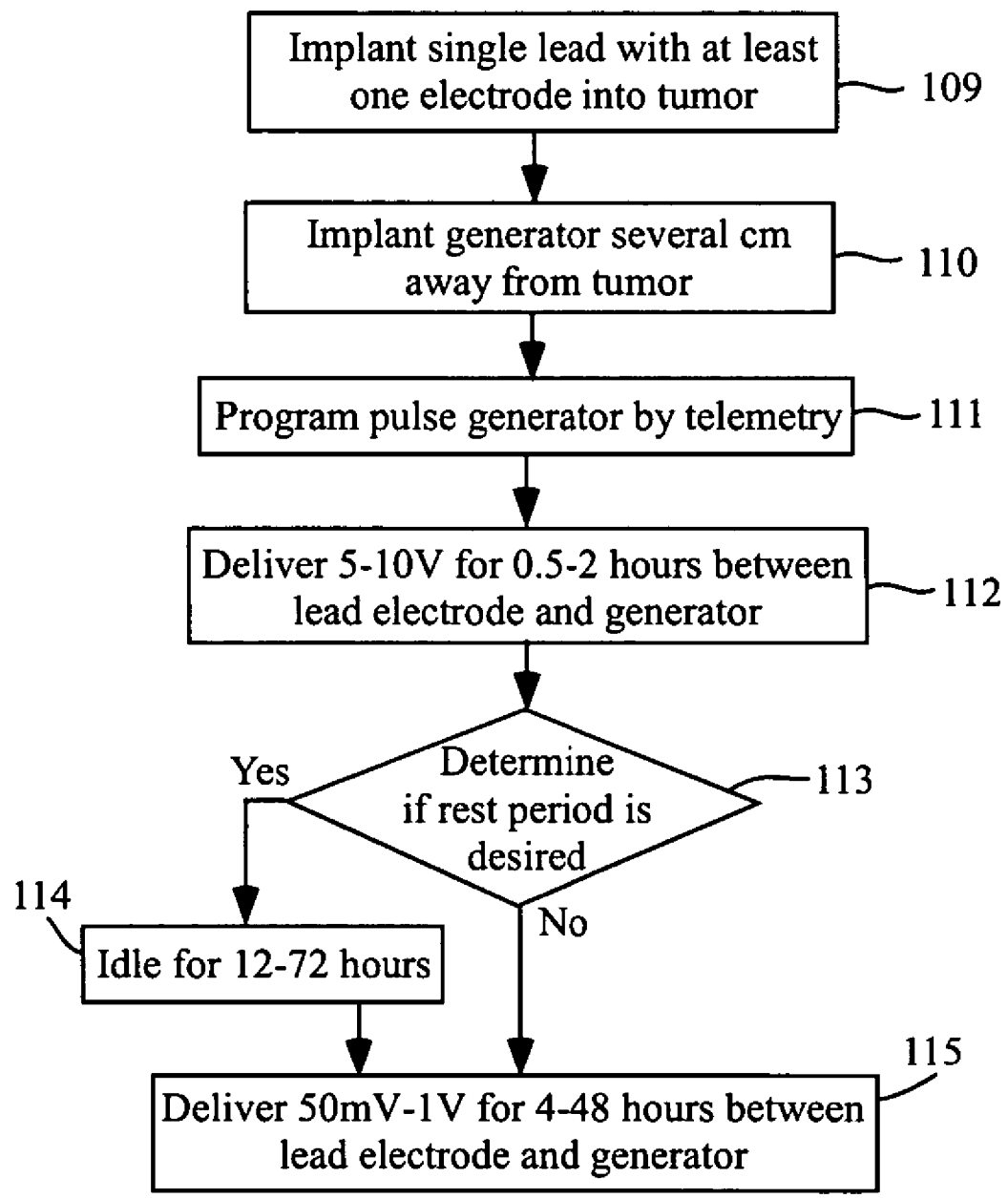
FIG. 27a-27f are flow charts representing exemplary methods of the preferred embodiment.
Figure 27B:
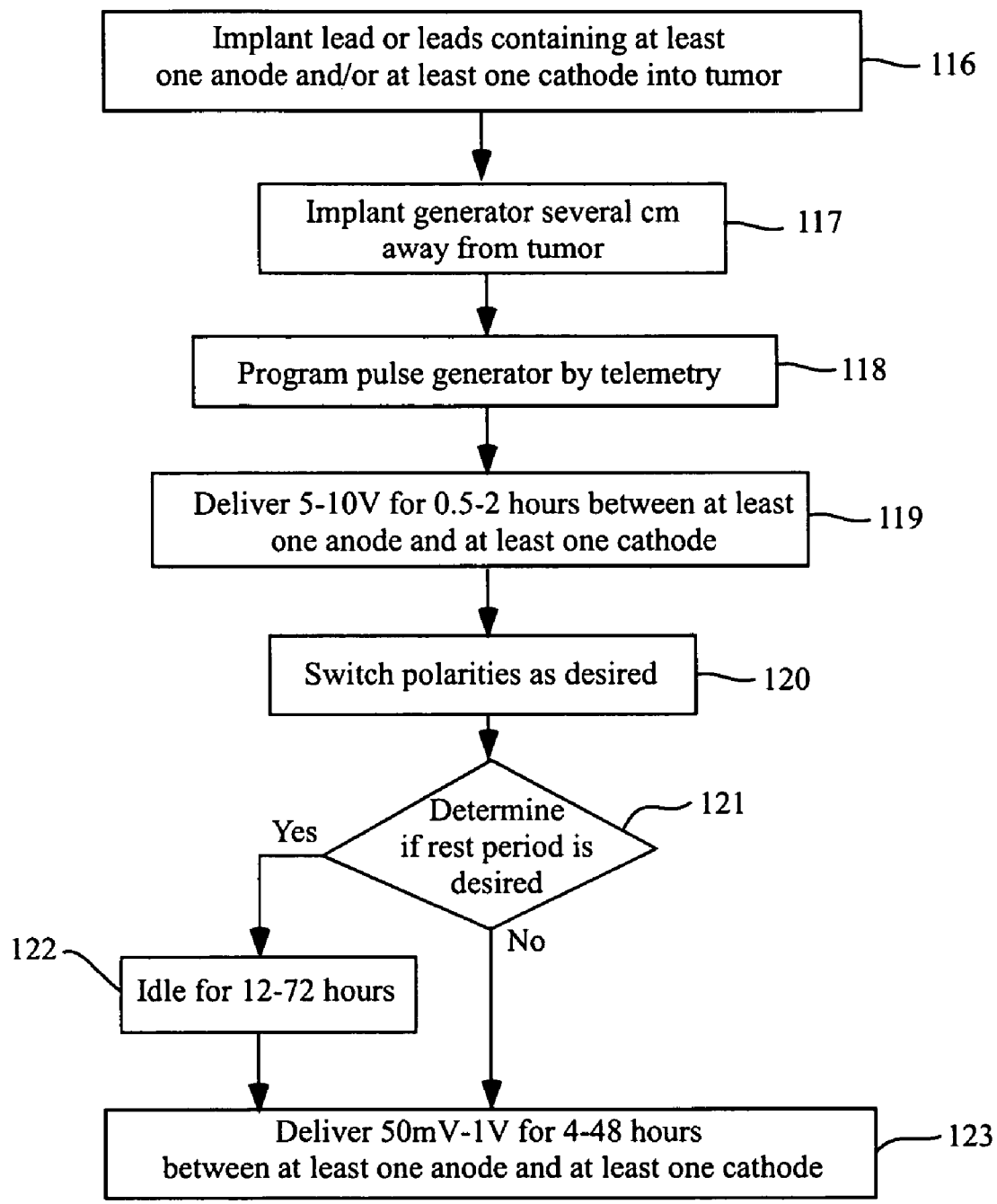
Figure 27C:
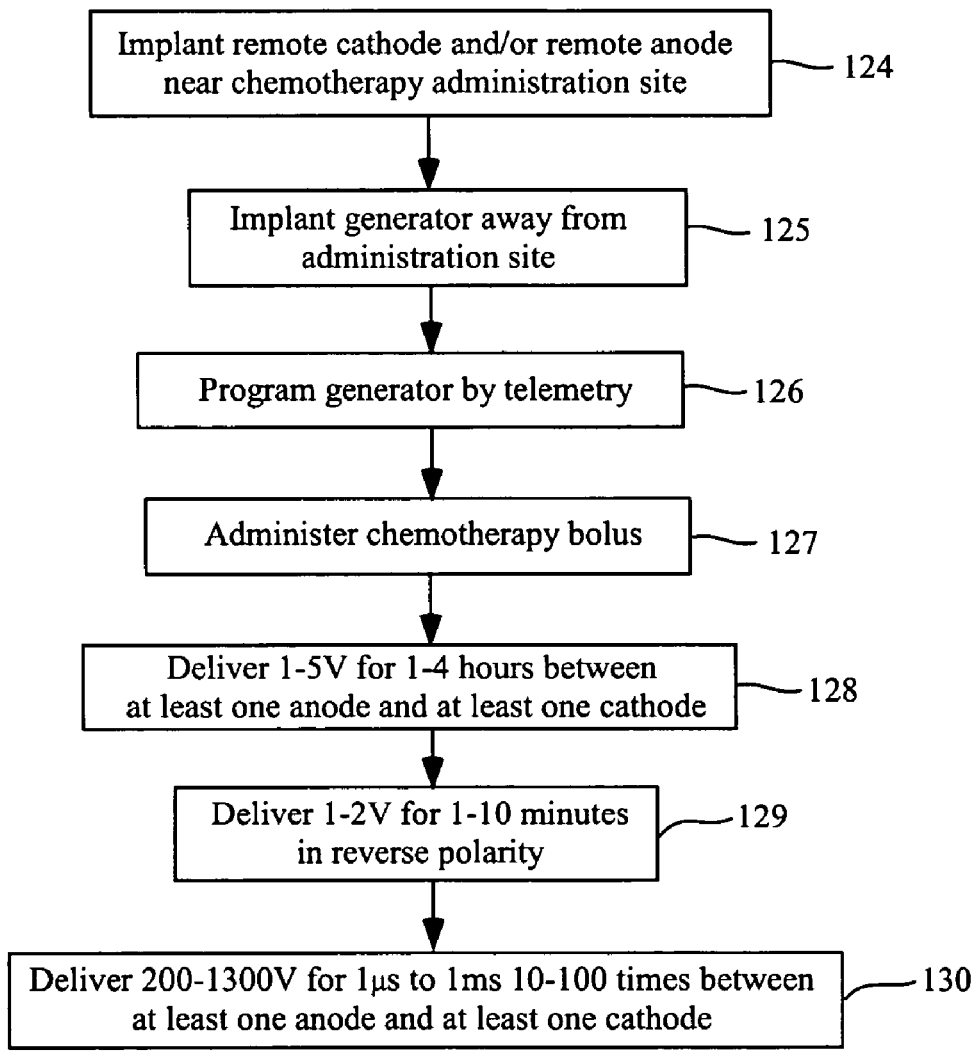
Figure 27D:
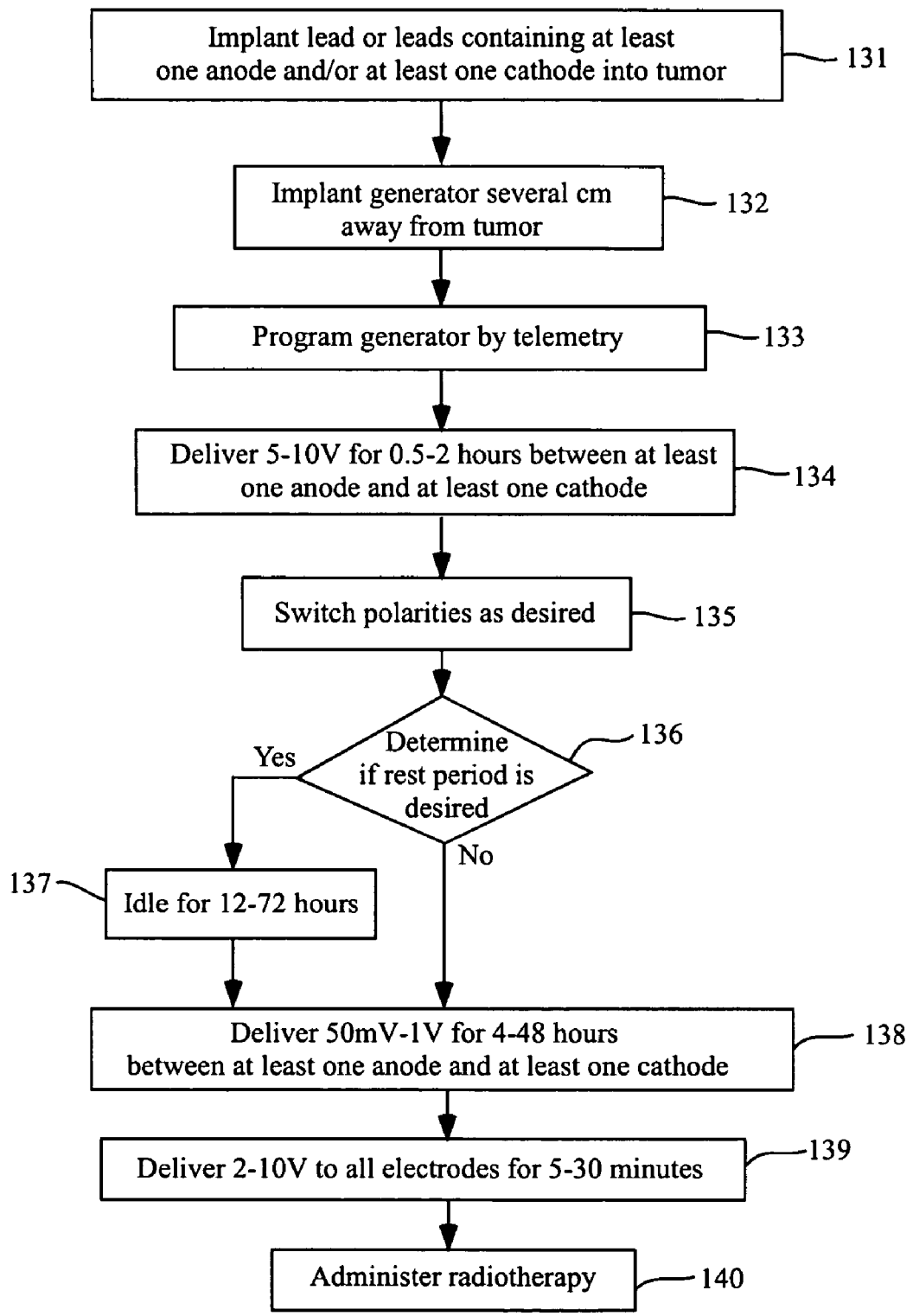
Figure 27E:
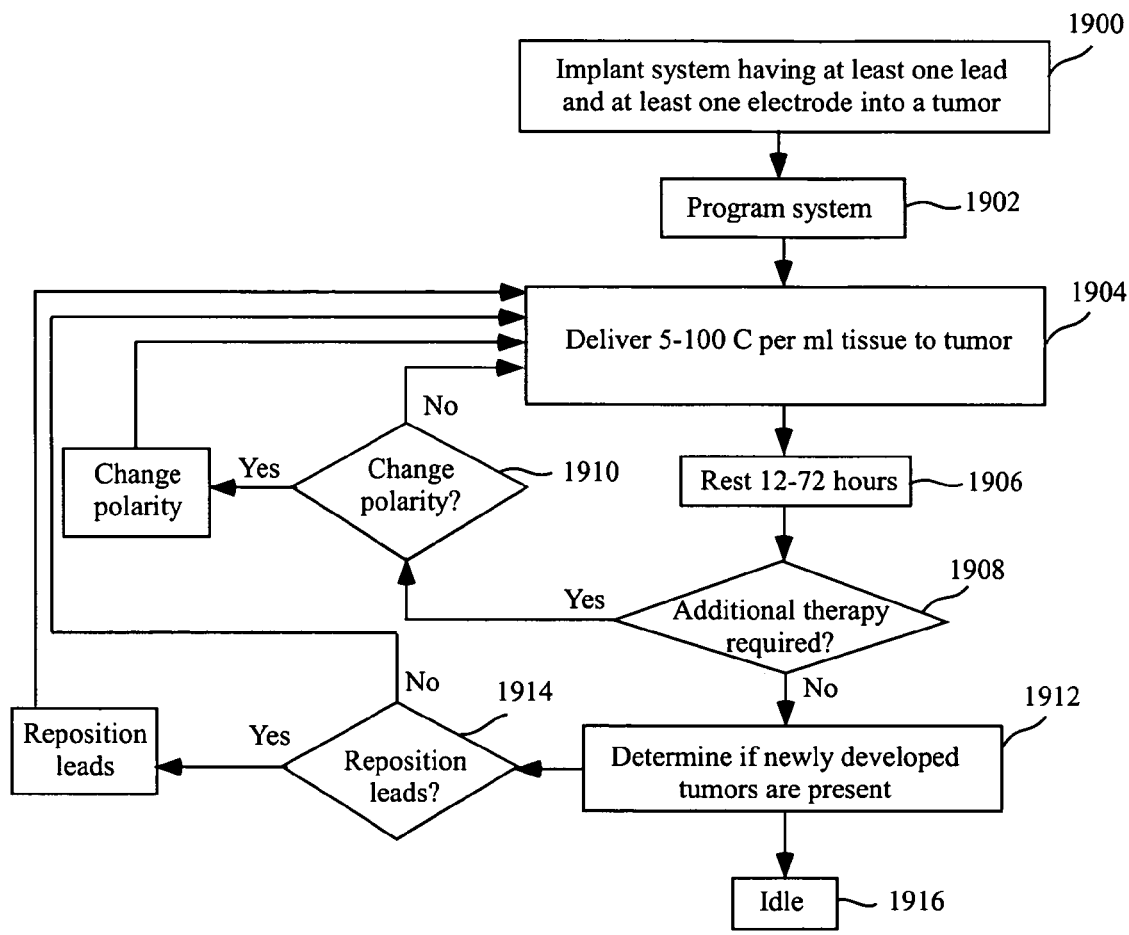
Figure 27F:
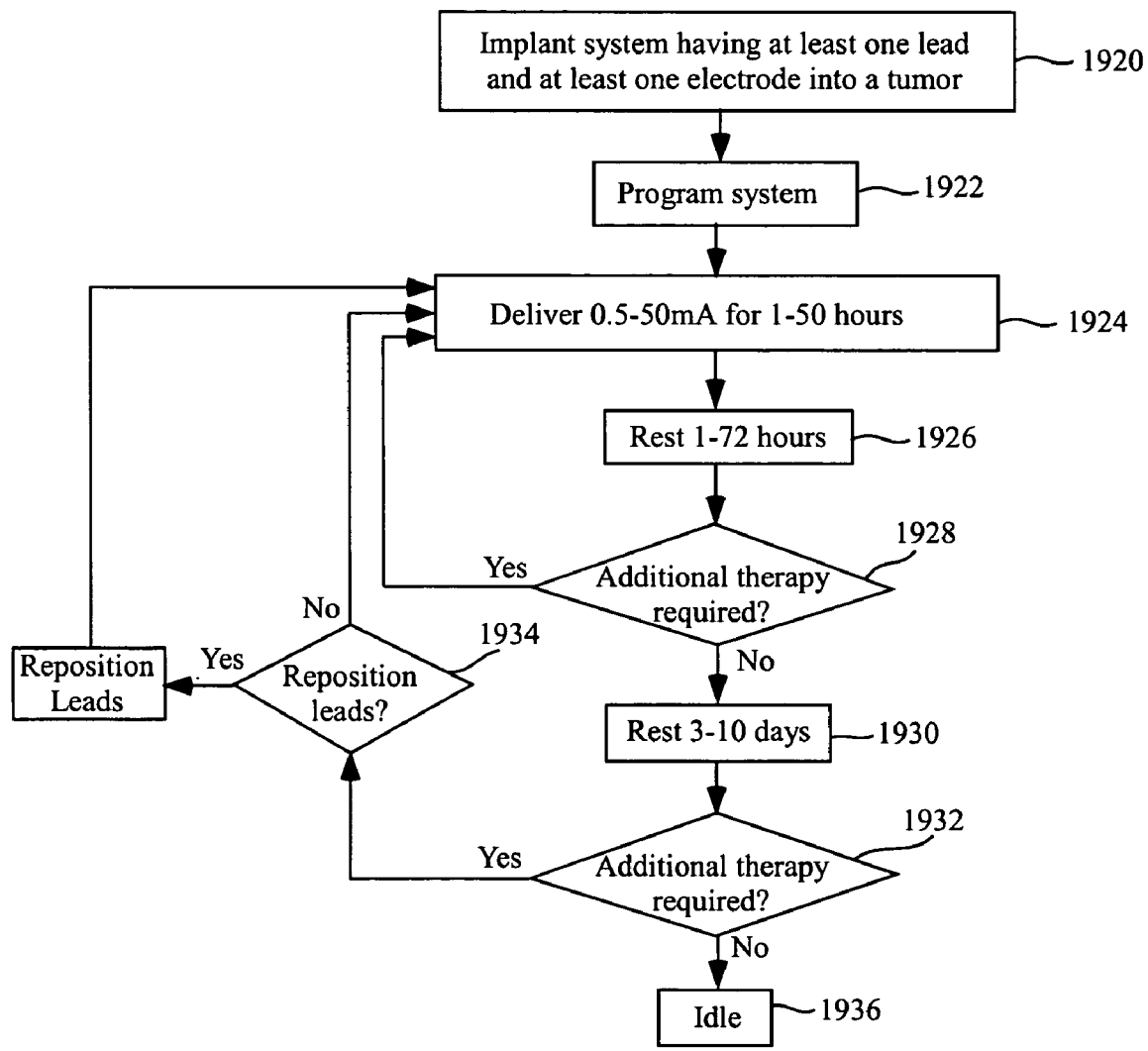

Referring now to FIG. 27a-27f, methods of the preferred embodiment are depicted. FIG. 27a relates to an electrical therapy regimen for use with a basic unipolar configuration of the preferred embodiment. FIG. 27b relates to an electrical therapy regimen for use with a bipolar configuration of the preferred embodiment. FIG. 27c relates to an electrical therapy regimen for use with chemotherapeutic agents. FIG. 27d relates to an electrical therapy regimen for use with radiation therapy. FIG. 27e relates to an electrical therapy method using coulombs. FIG. 27f is an electrical therapy method using current.

Looking now to a basic unipolar configuration of the preferred embodiment depicted in FIG. 27a, a method of the preferred embodiment is depicted. Beginning at step 109 a lead with at least one electrode is implanted into, nearby, or adjacent to a tumor. In a preferred embodiment, the electrode is anodal and is implanted into a tumor and the generator housing serves as a cathode.

At step 110 a generator is implanted away from the tumor. Determination of the implantation site for a generator is dependent on a number of factors. For example, a generator may be implanted directly on a tumor without any leads. However, in some cases, such as when electrical therapy is used in conjunction with radiotherapy, this option may not be desirable because the device may be damaged by ionizing radiation (although in another embodiment the device may be protected with radiation shielding). Moreover, implanting a generator remotely may be safer for the patient and surgically more convenient. For example, in the case of a brain tumor, it may not be feasible or desirable to implant a generator in the head whereas the shoulder area may be more appropriate. Although the inventors contemplate a generator implanted directly at the tumor site, in practice the generator is often implanted several cm away. In a preferred embodiment, the generator is implanted 10 cm away; however, distances from 0 to 40 cm are acceptable. At step 111 the generator is programmed by telemetry. Many parameters can be programmed such as duration of therapy, duty cycle, pulse width, voltage, current, total coulombs delivered, anode/cathode switching, and the like. The specific parameters described below are only one sequence of an infinite number of settings, and therefore, should be seen as illustrative only and in no way limiting.

In this example, directed to a basic unipolar configuration of the preferred embodiment, at step 112 5-10 V are delivered between the lead electrode and generator housing for 0.5 to 2 hours. In a preferred embodiment, the lead electrode is anodal while the generator housing serves as the cathode. However, in another embodiment, the lead electrode may serve as a cathode while the generator housing serves as an anode. Moreover, the polarities of the lead electrode and generator housing may be designed to switch as desired during therapy.

Step 112 changes the pH in the tumor and begins rapid destruction. pH changes down to about 2 and up to about 13 may be found at the anode and the cathode, respectively. The pH change will be less at the housing since the current density there is significantly lower relative to its large surface area. A change in pH of at least 2 may begin destruction. In a preferred embodiment, voltages in the range of 3 to 25 V and durations in the range of 10 minutes to 2 hours are useful for changing the internal tumor pH.

At step 113 the generator may optionally begin monitoring voltage between the anode and the pulse generator housing. If an internal intrinsic healing current is detected or a rest period is desired for any other reason, no further therapy is provided until the device is reprogrammed. As result, the system remains in idle mode at step 114. Alternatively, the device may automatically restart electrical therapy after a preset amount of time. In a preferred embodiment, the system remains in idle mode for 12 to 72 hours. The use of a rest period is set through the programmer at the judgment of the health practitioner.

However, if no internal healing current is detected or a rest period is not desired for any other reason, therapy will immediately enter step 115 where 50 mV to 1 V is delivered for 4-48 hours between the lead electrode and the generator housing. This low voltage field applied at step 115 may attract leukocytes (white blood cells) to the tumor in order to clean up destroyed cells caused by step 112. A voltage of 50 mV is typically high enough to attract leukocytes, but below the electrolysis level. In a preferred embodiment, voltages ranging from 50 mV to 1 V and durations ranging from 4 to 48 hours are useful for attracting leukocytes.

Referring now to FIG. 27b, another method of the preferred embodiment is shown. The method of FIG. 27b represents a bipolar configuration of the preferred embodiment. Beginning at step 116 one or more leads containing at least one anode electrode and at least one cathode electrode are implanted into, nearby, or adjacent to a tumor. The lead or leads and bipolar electrodes comprised therein may be of any configuration.

At step 117 a generator is implanted away from the tumor. In a preferred embodiment, the generator is implanted several cm away with a preferred distance of 10 cm while distances of 0 to 40 cm are acceptable. At step 118 the generator is programmed by telemetry. Many parameters can be programmed such as duration of therapy, duty cycle, pulse width, voltage, current, total coulombs delivered, anode/cathode switching, and the like. The specific parameters described below are only one sequence of an infinite number of settings, and therefore, should be seen as illustrative only and are in no way limiting.

In this example, directed to a bipolar configuration of the preferred embodiment, at step 119 5-10 V are delivered between any combination and configuration of anode electrode or electrodes and any combination and configuration of cathode electrode or electrodes for 0.5 to 2 hours. This step 119 changes the pH in the tumor and begins rapid destruction. pH changes down to about 2 and up to about 13 may be found at the anode and cathode, respectively. A change in pH of at least 2 may begin destruction. In a preferred embodiment, voltages in the range of 3 to 25 V and durations in the range of 10 minutes to 2 hours are useful for changing the internal tumor pH.

At step 120 the polarities of anode electrodes and cathode electrodes may switch as desired during therapy. Polarities may advantageously switch because tumors may respond differently to one polarity versus the other (e.g. anodic versus cathodic). A sensor or imaging may determine the level of shrinkage which will positively correspond to the efficacy of treatment.

At step 121 the generator may optionally begin monitoring voltage between the anode and the pulse generator housing. If an internal intrinsic healing current is detected or a rest period is desired for any other reason, no further therapy is provided until the device is reprogrammed. As a result, the system remains in idle mode at step 122. Alternatively, the device may automatically restart electrical therapy after a preset amount of time. In a preferred embodiment, the system remains in idle mode for 12 to 72 hours. The use of a rest period is set through the programmer at the judgment of the attending health practitioner.

However, if no internal healing current is detected or a rest period is not desired for any other reason, therapy will immediately enter step 123 where 50 mV to 1 V is delivered for 4 to 48 hours between an anode and a cathode. This low voltage field applied at step 123 may attract leukocytes (white blood cells) to the tumor in order to clean up destroyed cells caused by step 119. A voltage of 50 mV is typically high enough to attract leukocytes, but below the electrolysis level. In a preferred embodiment, voltages ranging from 50 mV to 1 V and durations ranging from 4 to 48 hours are useful for attracting leukocytes.

Referring now to FIG. 27c, another method of the preferred embodiment is shown. The method of FIG. 27c is useful when using chemotherapy in conjunction with electrical therapy. Beginning at step 124 a remote cathode and/or anode electrode is implanted near the chemotherapy administration site.

At step 125 a generator is implanted away from the tumor. In a preferred embodiment, the generator is implanted at least 10 cm away. By placing the generator further away from the tumor than in FIG. 27a and FIG. 27b, a chemotherapeutic agent may be more effectively directed to a tumor site. At step 126 the generator is programmed by telemetry. Many parameters can be programmed such as duration of therapy, duty cycle, pulse width, voltage, current, total coulombs delivered, anode/cathode switching, administration regimen of the chemotherapeutic agent, and the like. The specific parameters described below are only one sequence of an infinite number of settings, and therefore, should be seen as illustrative only and is in no way limiting.

At step 127 a chemotherapy bolus is administered. Administration of a chemotherapeutic agent may be by way of any of a catheter, implanted drug pump, an injection, an oral dosage, a suppository, a skin patch and any other type of bolus. In a preferred embodiment, a catheter may be implanted to non-invasively administer drugs to a patient. An implanted catheter advantageously decreases risk of infection because the skin barrier is not punctured. Numerous types of catheters may be used in conjunction with the present embodiment and a number of them are described later in the application. Any of the catheters described therein may be used with the method of the preferred embodiment described herein. Any drug which enhances amelioration of cancer may be used. In a preferred embodiment bleomycin, mitoxantrone, melphalan, dactinomycin, adriamycin, and/or doxorubicin are used. Selection of the specific chemotherapeutic agent should be made in conjunction with an electrical therapy treatment regimen. Alternatively, a drug with specific properties may be chosen and then an electrical therapy regimen can be adjusted appropriately. For example, designing an electrical therapy regimen to reduce oxygen, which can be accomplished by making all of the electrodes slightly or briefly cathodic, will enhance the effect of doxorubicin.

At step 128 1 to 5 V are delivered between at least one anode and at least one cathode for 1 to 4 hours. The at least one cathode may be any of an electrode and a generator housing. The electrical field created between an anode and a remote cathode attracts a (negatively charged) chemotherapeutic agent to the tumor. A chemotherapeutic agent may be attracted to the tumor when the agent is administered in any way. For example, the agent may be administered systemically by any means and/or directly by any means to the site. By applying the appropriate polarity to a tumor site a charged chemotherapeutic agent is drawn via iontophoresis to the site, whether systemically or locally administered. In order to effectively attract a charged chemotherapeutic agent to the tumor, the polarity of the tumor should be made opposite of the chemotherapeutic agent's charge. For example, for a negatively charged drug, the tumor electrode polarity should be positive and for a positively charged drug (such as, for example, bleomycin and adriamycin), the tumor electrode polarity should be negative. In other words, in the case of a negatively charged chemotherapeutic agent, electrical therapy may be applied between an anode electrode implanted in a tumor and a remote cathode. Because the anode electrode draws negative charge, the negatively charged chemotherapeutic agent will migrate towards the anode electrode, thus increasing the concentration of negatively charged chemotherapeutic agent in the tumor. Alternatively, in the case of a positively charged chemotherapeutic agent, electrical therapy may be applied between a cathode electrode implanted in a tumor and a remote anode. Because the cathode electrode draws positive charge, the positively charged chemotherapeutic agent will migrate towards the cathode electrode, thus increasing the concentration of positively charged chemotherapeutic agent in the tumor mass.

At step 129 1 to 2 V may be applied in reverse polarity as step 128 for 1 to 10 minutes to disperse a chemotherapeutic agent throughout a tumor mass. For example, in the case of a negatively charged chemotherapeutic agent, electrical therapy may be advantageously applied between an anode implanted into a tumor and a remote cathode as described in step 128. Following concentration of the negatively charged chemotherapeutic agent around an anode implanted in the tumor as described in step 128, polarity may reverse such that electrical therapy is applied between a cathode implanted in the tumor and a remote anode. This step 128 advantageously disperses a negatively charged chemotherapeutic agent throughout the peripheral tumor tissue. In another example, in the case of a positively charged chemotherapeutic agent, electrical therapy may be advantageously applied between a cathode implanted into a tumor and a remote anode as described in step 128. Following concentration of the positively charged chemotherapeutic agent by, for example iontophoresis, around a cathode electrode implanted in the tumor as described in step 128, polarity may reverse such that electrical therapy is applied between an anode implanted in the tumor and a remote cathode. This step 128 advantageously disperses a positively charged chemotherapeutic agent throughout the peripheral tumor tissue.

Following step 128 wherein an ionically charged substance is concentrated in the tumor area, by for example iontophoresis, and step 129, wherein the charged substance is optionally dispersed throughout the local tumor area by, for example, reversing polarity, cellular membranes are rendered permeable via high voltage pulses, such as in electroporation. In this manner, the ionic substance, such as a chemotherapeutic agent is concentrated in a tumor and then the cancerous cells are forced to accept the agent via electroporation.

At step 130 cell membranes are forced open by electroporation with an appropriate electrical therapy regimen. Although there are numerous electrical ways to force open a cellular membrane, the following is an example of an appropriate voltage and time duration. At step 130 200 to 1300 V for 1 μs to 1 ms may be delivered in repetition 10 to 100 times between at least one anode and one cathode. In one embodiment, the duty cycle may range from 20 percent to 80 percent. Step 130 forces open cancer cell membranes to facilitate entry of drug molecules into cancer cells. Electroporation as described in step 130 allows molecularly small and large chemotherapeutic agents through the cell membrane. However, this step 130 is particularly advantageous for large chemotherapeutic agents because of their size. The device may also be constructed so that the device housing can be used as the remote electrode when appropriate with consideration of patient comfort, safety (e.g. avoiding cardiac fibrillation), and electroporation effectiveness. In another embodiment, electroporation may be achieved via an external power source. An external power source may be coupled to the leads of the implanted electrical system by a port or any other coupling means for the purpose of supplying appropriate voltages, pulse widths, spacing periods, and repetitions appropriate for electroporation. This embodiment may advantageously reduce the need for high voltage generation circuitry and high power supply needed for electroporation.

Referring now to FIG. 27*d*, another method of the preferred embodiment is shown. The method of FIG. 27*d* is useful when using radiation therapy in conjunction with electrical therapy. Beginning at step 131 one or more leads containing at least one anode electrode and/or at least one cathode electrode is implanted into, nearby, or adjacent to a tumor. The lead or leads and electrodes comprised therein may be of any configuration.

At step 132 a generator is implanted away from the tumor. In a preferred embodiment, the generator is implanted several cm at least 5 cm and preferably 10 cm away while a distance of 3 to 40 cm is workable. The generator should be implanted such that it will not be in the way of ionizing radiation. Alternatively, the generator can be made of radiation hardened circuitry that can survive the strong radiation. At step 133 the generator is programmed by telemetry. Many parameters can be programmed such as duration of therapy, duty cycle, pulse width, voltage, current, total coulombs delivered, anode/cathode switching, and the like. The specific parameters described below are only one sequence of an infinite number of settings and, therefore, should be seen as illustrative only and in no way limiting.

At step 134 5-10 V are delivered between any combination and configuration of anode electrode or electrodes and any combination and configuration of cathode electrode or electrodes for 0.5 to 2 hours. This step 134 changes pH in the tumor and begins rapid destruction. pH changes down to about 2 and up to about 13 may be found at the anode and cathode, respectively. A change in the pH of at least 2 may begin destruction. In a preferred embodiment, voltages in the range of 3 to 25 V and durations in the range of 10 minutes to 2 hours are useful for changing the internal tumor pH.

At step 135 polarities of anode or anodes and cathode or cathodes may optionally switch as desired during therapy. By switching polarities more consistent tumor destruction may ensue by ensuring that each electrode serves as both an anode and as a cathode. Moreover, some tumors shrink more quickly with one polarity versus the other (e.g. anode versus cathode).

At step 136 the generator may optionally begin monitoring voltage between the anode and the generator housing. If an internal intrinsic healing current is detected or a rest period is desired for any other reason, no further therapy is provided until the device is reprogrammed. As a result, the system remains in idle mode at step 137. Alternatively, the device may automatically restart electrical therapy after a preset amount of time. In a preferred embodiment, the system remains in idle mode for 12 to 72 hours as determined by the health practitioner preference and the patient response.

However, if no internal healing current is detected or a rest period is not desired for any other reason, therapy will immediately enter step 138 where 50 mV to 1 V is delivered for 4 to 48 hours between an anode and a cathode. This low voltage field applied at step 138 may attract leukocytes (white blood cells) to the tumor in order to clean up destroyed cells caused by step 134. A voltage of 50 mV is typically high enough to attract leukocytes, but below the electrolysis level. In a preferred embodiment, voltages ranging from 50 mV to 1 V and durations ranging from 4 to 48 hours are useful for attracting leukocytes.

At step 139 2 to 10 volts are applied to all electrodes, thereby rendering them anodic for 5 to 30 minutes. (As is readily understood by those of ordinary skill in the art, the housing or another large remote electrode must serve as a current return and hence will be cathodic.) This step 139 increases molecular oxygen concentration. In this case, radiation therapy and/or brachytherapy may be advantageously used in conjunction with increased molecular oxygen to enhance the effects of both radiation therapy and/or brachytherapy. Additionally, certain oxygenating substances such as, for example, nitromidazoles and perfluorocarbons, and/or any of the other oxygenating substances described hereinbelow, may be administered to the tumor site to increase oxygen concentration.

At step 140 a radioactive material is administered. In a preferred embodiment, the radioactive material may be cobalt-60, iodine-125, iodine-131, iridium-192, strontium-89 (metastron), and samarium-153.

Turning now to FIG. 27*e*, another method for use in electrical therapy is described. Beginning at step 1900 an electrical therapy system having at least one lead and at least one electrode is implanted into and/or in the periphery of a tumor. At the minimum, the system has a power source, at least one lead, and at least one electrode. However, the system may also include any of the numerous types and variations of options such as, for example, power sources (internal and/or external), electrodes, electrode arrays, leads, fixation means, electrical ports, and drug infusion devices described herein.

At step 1902 the system is programmed. The system may be programmed by any of the means described herein, such as by RF. The system may be programmed according to any of the options and parameters described herein. At step 1904 5 to 100 C per ml tumor tissue is administered. The 5 to 100 C may be delivered in any amount of time desired. For example, in DC ablation, the time period may be longer whereas in electroporation, the time period may be shorter. Following at step 1906, the system may rest for 12-72 hours. Following the rest period, a medical practitioner may review various parameters, such as, for example, internal pH, oxygen concentration, temperature, and any of the other parameters described herein to determine if additional therapy is required. Alternatively, the device, using a closed-loop mechanism, may determine if additional therapy is required. The closed-loop parameters may be any as described herein. If additional therapy is required (or desired) the system may change polarity at step 1910. Again, a medical practitioner may determine if polarity reversal is needed or desired for any reason. Alternatively, the device may determine if polarity reversal is needed or advantageous based on the closed-loop system described herein. At this point, the anodes may switch to cathodes (and vice versa) dependent on the system and/or medical practitioner's assessment. However, the system and/or medical practitioner may determine that polarity reversal in not necessary or desirable. In any case, the system enters step 1904 where 5-100 C per ml tissue is delivered to a tumor again.

If additional therapy is not needed or desired according to the system and/or medical practitioner at step 1908 the system enters step 1912. At step 1912 the system and/or medical practitioner determines if newly developed tumors are present. The system and/or medical practitioner may use imaging, such as described herein, to determine the existence (and location if any) of newly generated tumors. If more tumors are detected then the system enters step 1914. At step 1914 the system and/or medical practitioner determines if the leads should be repositioned. Leads may need to be repositioned if additional tumors are located so that the newly generated tumors may be subjected to electrical therapy. However, if a new tumor is substantially in the same area as an electrode, it may not be necessary to reposition the lead or leads. In either case, the system enters step 1904 where 5-100 C per ml tissue is delivered to a tumor again. However, if at step 1912 no new tumors are present, the system idles at step 1916 until the system recycles due to closed-loop programming, a medical practitioner reprograms the system, or a patient reprograms the system, which may be accomplished by using the patient control mechanisms described herein.

The method of FIG. 27e may be used in conjunction with chemotherapy and radiation therapy as desired.

Turning now to FIG. 27f an electrical therapy method using current is depicted. Beginning at step 1920 an electrical therapy system having at least one lead and at least one electrode is implanted into and/or in the periphery of a tumor. At the minimum, the system has a power source, at least one lead, and at least one electrode. However, the system may also include any of the numerous types and variations of options such as for example, power sources (internal and/or external), electrodes, electrode arrays, leads, fixation means, electrical ports, and drug infusion devices described herein.

Following at step 1922 the system is programmed. The system may be programmed by any of the means described herein, such as by RF. The system may be programmed according to any of the options and parameters described herein. At step 1924 0.5 to 50 mA are applied to a tumor for 1-50 hours. However, step 1924 may be broken up into repeated sequences of shorter therapies. The period of the shorter therapies may be from 5 minutes to an hour and have a duty cycle of 20 to 80 percent. For example, 0.5 to 50 mA may be administered using a 20 minute period and a 50 percent duty cycle which would result in ten minute increments of current delivery interspaced with a five minute off period for a total of 25 hours. This turn off period may allow the healthy peripheral tissue to return to a normal pH, whereas the cancerous tissue, due to its poor buffering capability, would remain at a high or low pH. Less current over longer periods of time may be advantageous in certain circumstances whereas higher current over shorter periods of time may be advantageous in other circumstances. For example, in DC ablation, current is likely to be lower than in electroporation. Additionally, DC ablation is likely to be applied over a longer period of time than electroporation.

Following administration of electrical therapy at step 1924, the system may rest for 1-72 hours. This rest period may be desirable to allow the tumor to return to a normal pH. This in turn, should allow macrophages, dendritic cells, and other components of the immune system to enter the tumor, ingest dead tumor cells, and possibly present the cancer cell antigens to T cells and other components of the immune system. Following the rest period, the device, using a closed-loop mechanism, may determine if additional therapy is required. The closed-loop parameters may be any as described herein. Alternatively, a medical practitioner may review various parameters, such as, for example, internal pH, oxygen concentration, temperature, and any of the other parameters described herein to determine if additional therapy is required. If additional therapy is required (or desired) the system reenters step 1924 where 0.5 to 50 mA are delivered to a tumor for 1 to 50 hours.

However, if additional electrical therapy is not required or desired as determined by a closed-loop mechanism or a medical practitioner at step 1928, the system enters a rest period for 3 to 10 days at step 1930. Following this second rest period at step 1930 the system again determines by way of a closed-loop mechanism or by way of a medical practitioner if additional therapy is required or desired for any reason at step 1932. If additional therapy is required or desired, the system will determine, through a closed-loop mechanism or by a medical practitioner, if the leads should be repositioned at step 1934. Lead or leads may need to be repositioned if the tumor has changed shape or size and/or if new tumors are located. In either case, whether the lead or leads are repositioned or not, the system reenters the electrical therapy step at 1924 where 0.5 to 50 mA are delivered to a tumor for 1 to 50 hours. Importantly, the electrical therapy need not be the same each time.

Alternatively, if, at step 1932, no additional electrical therapy is required or desired, the system idles at step 1936 until the system recycles due to closed-loop programming, a medical practitioner reprograms the system, or a patient reprograms the system, which may be accomplished by using the patient control mechanisms described herein.

At any time following the rest period and for a period of up to a few months, adjuvants and cytokines may be administered to the patient to support the immune system. Examples of agents may include granulocyte-macrophage colony-stimulating factor (GMCSF), colony-stimulating factors (CSFs), poly-inosinic, cytidylic acid (poly-IC), interleukin-2 (IL-2), and CPG.

The method of FIG. 27f may be used in conjunction with chemotherapy and radiation therapy as desired.

Electrical therapy can be used separately without the addition of chemotherapeutic agents, radiation therapy, and brachytherapy. However, electrical therapy in conjunction with chemotherapeutic agents, radiation therapy, and brachytherapy may be advantageous to ameliorate cancer more effectively and/or more efficiently than electrical therapy alone. Each of the previously described methods and method steps illustrated in FIGS. 27a-27f may be used in conjunction with each other for increased effectiveness. For example, chemotherapy and radiation therapy may be used in conjunction with the method for unipolar and/or bipolar treatments.

Importantly, the present embodiment disclosed in each of the preferred methods is distinct from pacemakers because durations of more than a microsecond are not attainable by pacemakers. In this case, the present embodiment requires nearly 1000 times the energy as a typical pacemaker. For example, a 100 mV voltage for one day, with a system impedance of 1000 Ohms requires 864 mJ in comparison to a typical pacemaker which generates 1 mJ pulses.

Shown in FIG. 28a-28b and FIG. 29a-29b are current level profiles which vary from those described in the preferred embodiments of FIG. 27a-27d. The abscissa in each of FIG. 28a-28b and FIG. 29a-29b represents time, such that a point nearer to the ordinate is less time and a point further away from the ordinate is more time. The ordinate in each of FIG. 28a-28b and FIG. 29a-29b represents current, such that a point nearer to the abscissa is less current and a point further away from the abscissa is more current. Each of FIG. 28a-28b and FIG. 29a-29b start at a baseline 141 which may be described as the normal, unique body current detected in each patient. Dependent on each patient's unique baseline current level 141, a therapeutic current level 143 of between 50 µA and 25 mA or 50 mV to 25 V will be attained by increasing the current 142. Due to the unique circumstances of each patient, current may be increased relatively quickly up to 1 A per second or 1 mA per ms or more gradually at 1 µA per second but more typically around 1 mA per second.

Figure 28A:
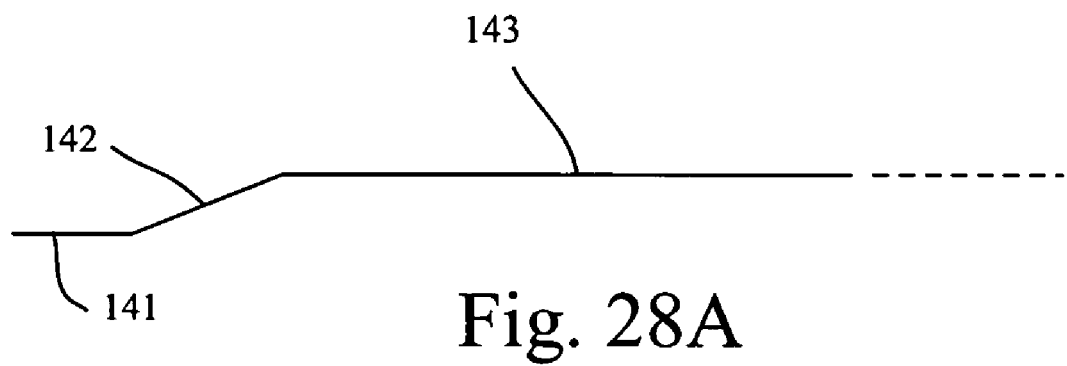
FIG. 28a-28b are graphs representing exemplary current levels for use in electrical therapy.
Figure 28B:
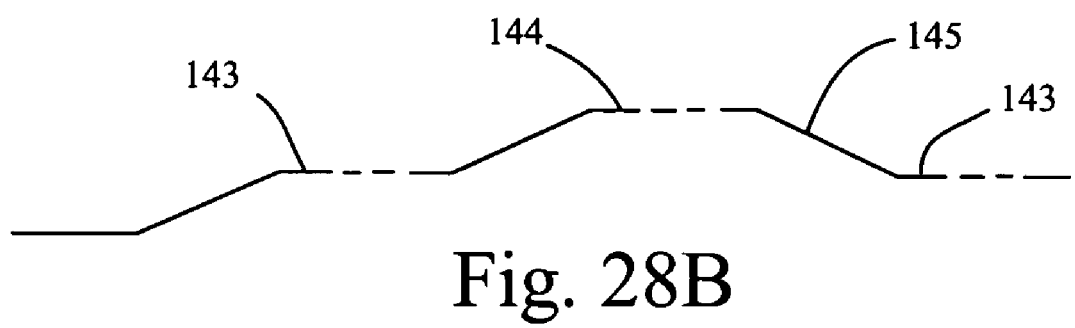

In FIG. 28a the therapeutic current level 143 is attained by gradually increasing the current 142 from the initial baseline 141. Gradually increasing current may be advantageous to reduce any potential pain experienced by a patient. In FIG. 28b therapeutic current 143 is increased to level 144 between 100 µA and 50 mA in response to an input from a microprocessor and is later restored gradually 145 to its original value 143. These changes may be in response to a sensor input, to circadian or other body rhythms, and to changes in measured heart rate variability.

Figure 29A:
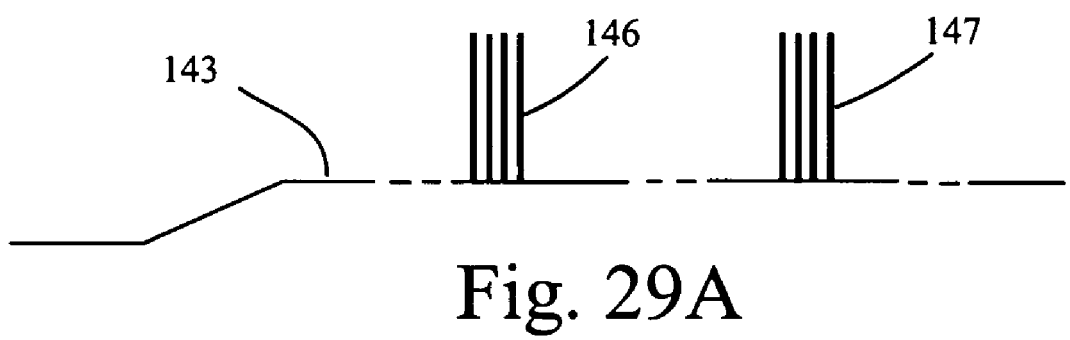
FIG. 29a-29b are graphs representing exemplary current levels for use in electrical therapy.
Figure 29B:
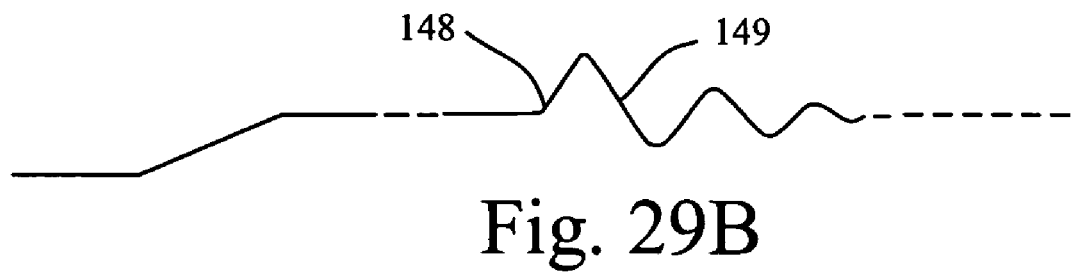

FIG. 29a shows a therapeutic current level 143 and at least one electroporation therapy 146 and 147 with an exemplary level of about 2 amperes applied at desired times. In a preferred embodiment, electroporation therapies 146 and 147 may be performed in conjunction with chemotherapy sessions. Furthermore, electroporation pulses may be biphasic and may be applied synchronously with a detected heartbeat in order to reduce the risk of inducing cardiac arrhythmias. Feedback may also be used to adjust electroporation parameters. For example, the electrical consequences of electroporation may be used to adjust the distribution of the electrical field at the electrodes. FIG. 29b represents the use of electrical therapy with a healing signal 149 generated within the device. At step 148 the tumor is destroyed. In response, the device applies a healing current 149 to the former tumor site. The previous examples are only several illustrations of potential variations in current level for the present embodiment and are in no way limiting. Each therapy will vary in terms of current level and/or voltage level and rate of achieving current level depending on the specific circumstances, including the patient, therapy regimen, options and variations in the device, and other types of therapy used concurrently with electrical therapy.

Figure 30:
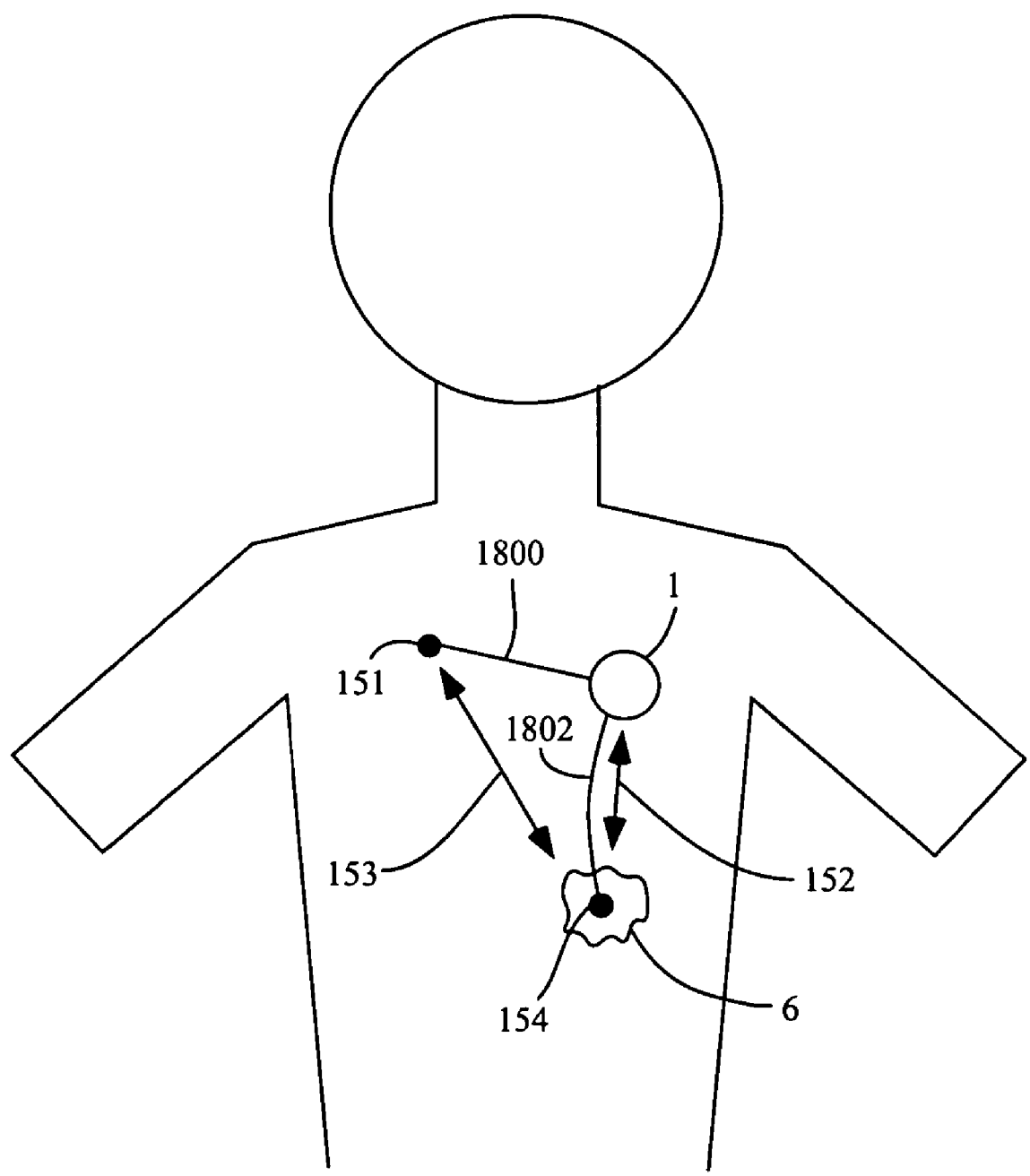
FIG. 30 is a diagram representing exemplary therapeutic pathways in a human body during electrical therapy.

Illustrated in FIG. 30 are examples of therapeutic current paths for a tumor located in the upper abdominal region of a human. In this example, the tumor may be located specifically in the liver. Shown are a generator 1, a tumor 6, a remote cathode 151, an exemplary primary therapeutic current 152, an exemplary secondary therapeutic current 153, and anode 154, and leads 1800 and 1802. Although the anode 154, the remote cathode 151, and the generator 1 can be placed in various locations depending on where the tumor 6 is located, the following are examples of the preferred placements for the anode 154, the remote cathode 151, and the generator 1 for the tumor 6 located in the upper abdominal cavity of a human as shown in FIG. 30. The primary therapeutic current 152 flows between the anode 154, located inside tumor 6, and the generator housing 1, which acts as the primary cathode. The secondary therapeutic current 153 flows between the anode 154 and the remote cathode 151, which is located in the upper right thoracic region. More specifically, the remote cathode 151 may be specifically located directly below the right clavicle. The generator 1 is preferably located near the tumor 6 approximately 6-10 cm away and is the cathode for all currents except for a current used to direct a chemotherapeutic agent to the tumor 6. However, if the generator is being used as the remote electrode to attract the chemotherapeutic agent to the tumor 6 then it should be farther away such as 1 to 40 cm away. The generator 1 is located in the upper left thoracic region, and more specifically may be located directly below the left clavicle. In this embodiment, it may be advantageous to locate a remote cathode 151 further away from the tumor than the generator 1 (cathode) to better direct chemotherapeutic agents to the anode 154, thereby creating a secondary therapeutic current 153.

5. Chemotherapy and Radiation Therapy

Although electrical therapy alone is useful in treating cancer, in some cases amelioration of cancer is more effective and/or more efficient in conjunction with chemotherapy and/or radiation therapy. Periodic chemotherapy may be supplied by traditional means independent of any implant designed to deliver chemotherapeutic agents. Alternatively, an implant may be designed to supply chemotherapy treatment as well as electrical stimulation. In one embodiment, a generator contains a subcutaneous port for penetration by a hypodermic needle. A drug can be infused real time through the port and through a delivery tube into a tumor. The delivery tube may be built into a lead or it may be a separate tube. In another embodiment, a generator contains a reservoir for storing a drug or drugs. Under control of a timing circuit, the drug, or drugs, may be released through a tube into a tumor. The technology of implantable drug infusion pumps, ports, and tubes is well known to those of ordinary skill in the art. However, the combination of infusion pumps, ports, and tubes has not been used in conjunction with electrical therapy as described herein. A general benefit of combined electrical therapy and drug infusion is that, in the practice of implantable drug infusion pumps, reservoir and flow limitations dictate that chemotherapy drugs be highly concentrated. Electrical therapy can advantageously increase the effectiveness and efficiency of chemotherapy drugs, thus permitting lower concentrations or less frequent reservoir refilling.

Figure 31:
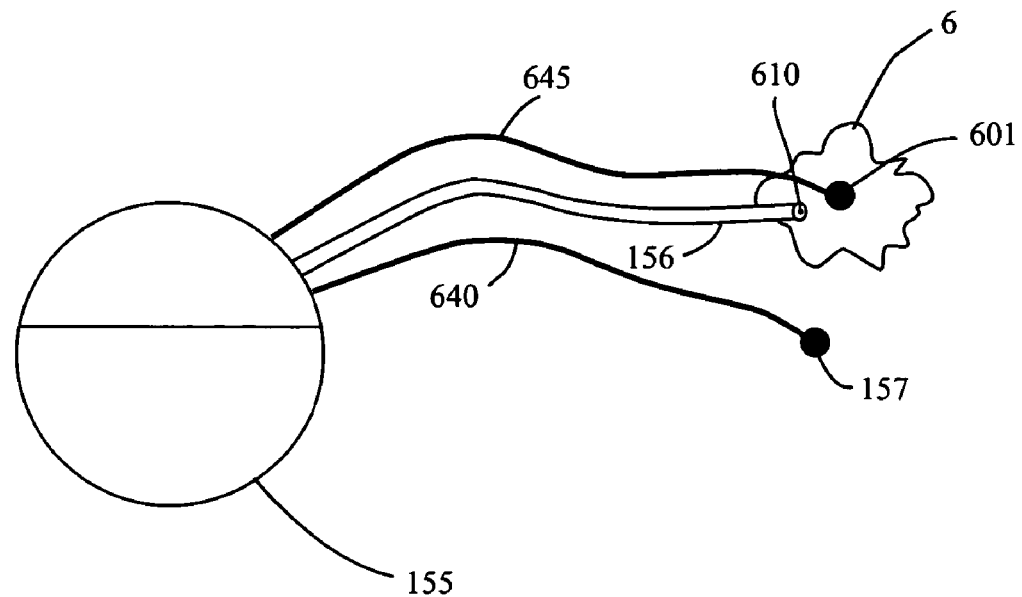
FIG. 31 is an illustration depicting an example of a generator/infusion device that infuses chemotherapeutic agents to a tumor such as may be employed with an electrical therapy system.
Figure 32:
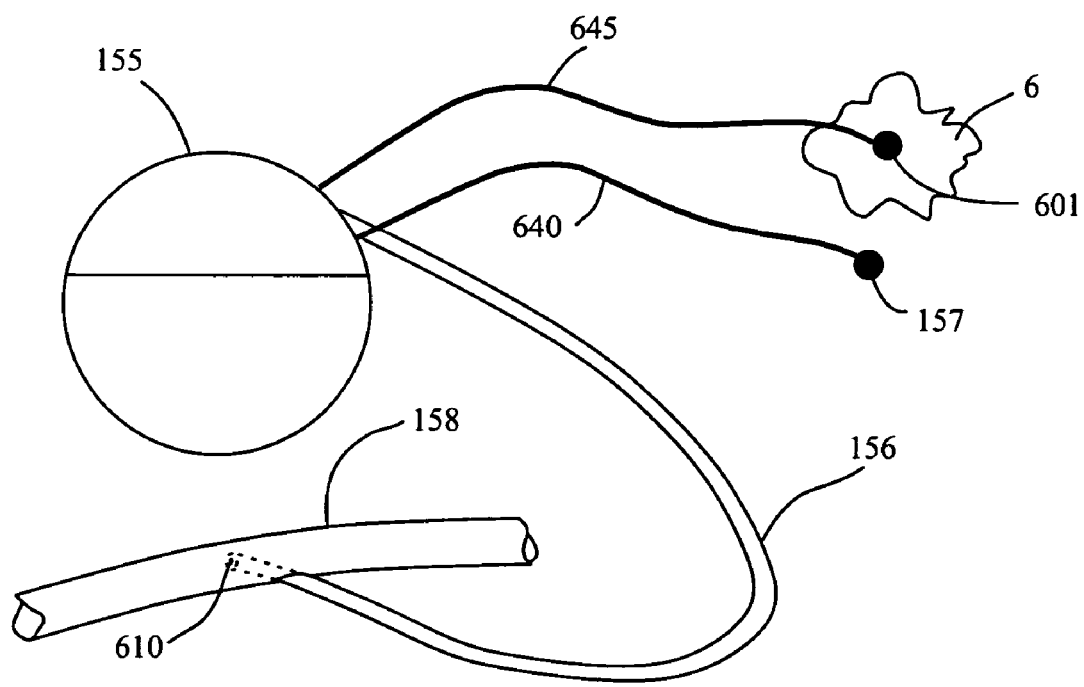
FIG. 32 is an illustration depicting an example of a generator/infusion device that infuses chemotherapeutic agents to the circulatory system such as may be employed in an electrical therapy system.

Turning now to FIG. 31-32, a generator/infusion device 155 is depicted. Shown are a tumor 6, the generator/infusion device 155, an infusion catheter 156, electrodes 157 and 601, a circulatory system 158, a catheter tip 610, and leads 640 and 645. The generator/infusion device 155 is coupled to the infusion catheter 156 and leads 640 and 645. The lead 640 terminates at the end opposite the generator/infusion device 155 with electrode 157 and the lead 645 terminates at the end opposite the generator/infusion device 155 with electrode 601.

The infusion catheter 156 is coupled to an internal reservoir (not shown) of a drug inside the generator/infusion device 155. The generator/infusion device 155 discharges a drug, or drugs, into the catheter 156. The drug, or drugs, flows through the catheter 156 to the catheter tip 610 where the drug, or drugs, is delivered to the tumor 6 or the circulatory system 158.

The electrodes 157 and 601 are electrically connected to the generator/infusion device 155 via leads 640 and 645 such that the electrodes 157 and 601 may be of either polarity, i.e. anode or cathode. Additionally, electrodes 157 and 601 may switch polarities as previously described hereinabove. In one embodiment, the generator/infusion device 155 may switch the polarities of electrodes 157 and 601 via internal circuitry such as described in FIG. 2e-2f hereinabove. Moreover, the generator/infusion device 155 may additionally serve as the anode or cathode, in place of, or in addition to electrodes 157 and 601. The electrodes 157 and 601 are located inside or peripheral to tumor 6. In the present embodiment, the electrode 157 is located at the tumor 6 periphery and the electrode 601 is located inside of tumor 6. However, electrodes 157 and 601 may be placed in any location relative to the tumor 6 useful for the treatment of cancer via electrical therapy. Furthermore, any combination of unipolar, multipolar, electrode arrays, and/or any other variation and configuration available for use with electrical therapy is contemplated by the inventors for use with the generator/infusion device 155 of the present embodiment.

The infusion catheter 156 can be inserted directly into the tumor 6, as shown in FIG. 31. Alternatively, as shown in FIG. 32, the infusion catheter 156 can be positioned to infuse drugs to remote locations, such as into a vein or artery of the circulatory system 158. In another embodiment, hepatic artery infusion can be used for liver malignancies, whereas venous infusion is preferred for many other cancers.

To ameliorate pain associated with cancer, morphine may be administered intrathecally with the device of the present embodiment. Moreover, subdural and intra-peritoneal infusion may also be used.

In another embodiment, more than one drug reservoir can be utilized to administer several drugs or to store increased amounts of the same drug. More than one drug reservoir may be inserted into a single generator/infusion device by separating the drug reservoir compartments, whereas a separate infusion device may also be used in conjunction with a generator/infusion device containing a single drug. In the case of administering more than one drug, the drugs can be infused on separate schedules and the patient may be given control over one drug but not the other. For example, the patient may have control over administration of a pain killer, such as morphine. However, the patient may not have control over the chemotherapeutic agent. Alternatively, several drug reservoirs may be used to increase the amount of chemotherapeutic agent on reserve, which leads to less frequent reservoir refilling.

Figure 33:
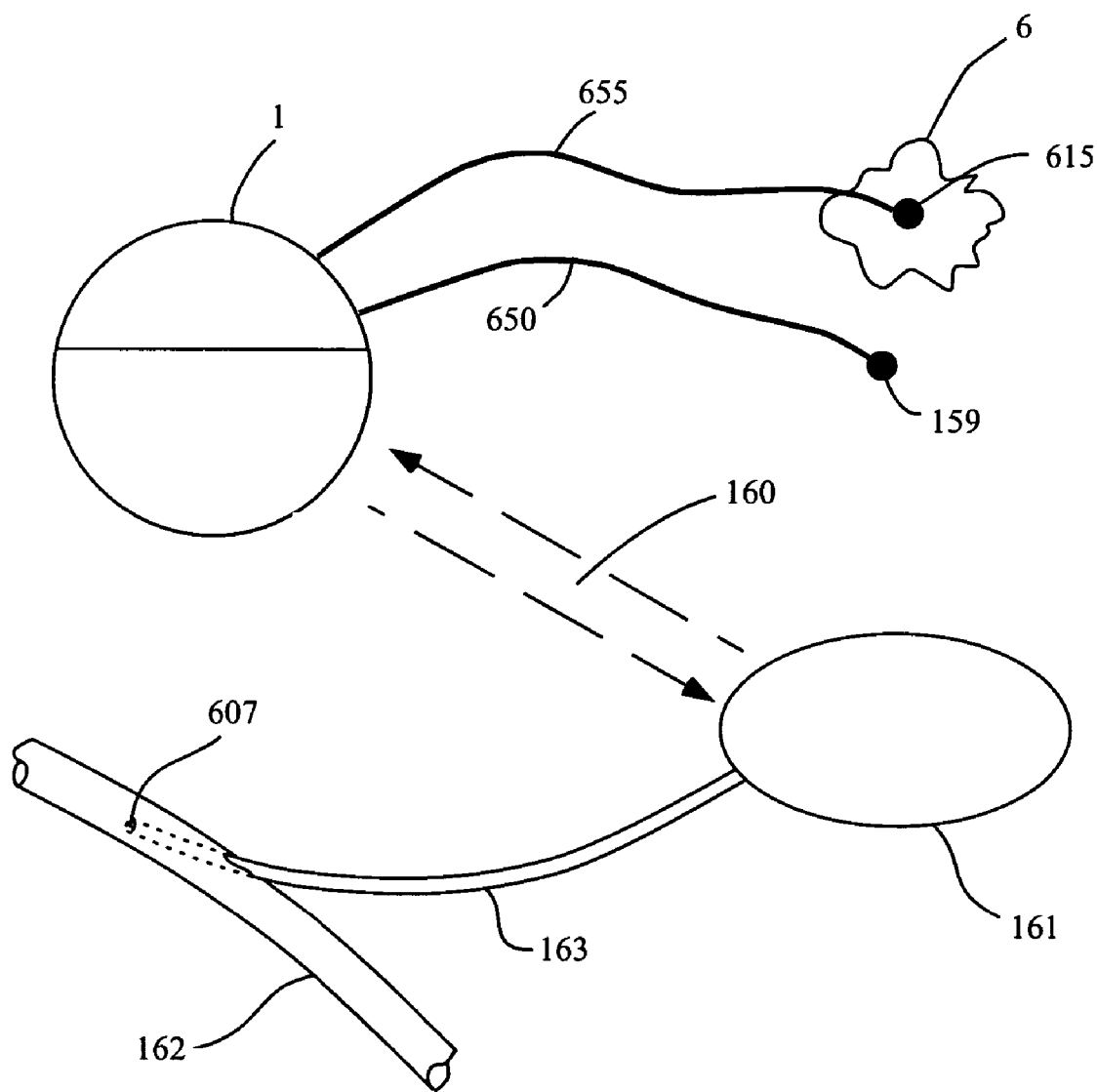
FIG. 33 is an illustration depicting an example of a drug infusion device that is physically separated from a generator such as may be utilized in electrical therapy systems.

Depicted in FIG. 33 is a drug infusion device 161 that is physically separated from a generator 1. Shown are the generator 1, a tumor 6, electrodes 159 and 615, a control/communication path 160, an infusion device 161, a target site 162, a catheter 163, a catheter tip 607, and leads 650 and 655.

The generator 1 is coupled to leads 650 and 655. The lead 650 terminates at the end opposite the generator 1 with electrode 159 and the lead 655 terminates at the end opposite the generator 1 with electrode 615. The electrodes 159 and 615 are electrically connected to the generator 1 such that the electrodes 159 and 615 may be of either polarity, i.e. anode or cathode. Additionally, electrodes 159 and 615 may switch polarities as previously described hereinabove. In one embodiment, the generator 1 may switch the polarities of electrodes 159 and 615 via internal circuitry such as described in FIG. 2e-2f hereinabove. Moreover, the generator 1 may additionally serve as the anode or cathode, in place of, or in addition to electrodes 159 and 615. The electrodes 159 and 615 are located inside or peripheral to the tumor 6. In the present embodiment, the electrode 159 is located at the tumor 6 periphery and the electrode 615 is located inside of tumor 6. However, electrodes 159 and 615 may be placed in any location relative to the tumor 6 useful for the treatment of cancer via electrical therapy. Moreover, any combination of unipolar, multipolar, electrode arrays, and/or any other variation and configuration available for use with electrical therapy is contemplated by the inventors for use with the present embodiment.

The catheter 163 is coupled to an infusion device 161. The infusion device 161 contains a drug reservoir (not shown), or reservoirs—for the administration of one or more drugs as described hereinabove). The infusion device 161 discharges a drug, or drugs, into the catheter 163. The drug, or drugs, flows through the catheter 163 to the catheter tip 607 where the drug, or drugs, is delivered to the target site 162. The target site 162 can be any of a vein, artery, hepatic artery, the tumor 6, and the tumor 6 periphery.

The generator 1 can control the infusion device 161 via the control/communication path 160 or vice versa. For example, the generator 1 may communicate a start or stop function to the infusion device 161 via control/communication path 160 in order to synchronize chemotherapy with electrical therapy. In one embodiment, synchronization can be programmed into each of the generator 1 and the infusion device 161 whereby each performs a function at a given time. The generator 1 can sense the infusion device 161 activity by monitoring various types of sensors. For example, in the case that the infusion device 161 catheter tip 607 is at the tumor 6 (not shown), a fluid sensor in the lead tip near the electrode 615 can sense the amount of chemotherapeutic agent infused. Alternatively, a pH sensor can be used to detect the amount of chemotherapeutic agent administered. Or, in another embodiment, as pH is sensed, certain chemotherapeutic agents may be advantageously administered. For example, the chemotherapeutic agent mitoxantrone is effective at basic pH values. Therefore, a pH sensor of the present embodiment may detect a basic or acidic pH value and appropriately send a signal to the infusion device 161 to automatically administer mitoxantrone when pH values are basic and stop administration of mitoxantrone when pH values are acidic. Alternatively, a pH sensor of the present embodiment may advantageously signal an operator when a high enough pH has been reached to manually administer mitoxantrone. Because many chemotherapeutic agents are charged, either positively or negatively, the sensed charge is proportional to the amount of drug effectively reaching the tumor. This type of detection can be used in closed-loop control. In another embodiment, the sound of a pump, such as peristaltic rollers and solenoid action, associated with infusion device 161 can be detected by a sound sensor. In yet another embodiment, the physiological effects of the chemotherapeutic agent are detected. Conversely, the infusion device 161 may be designed to sense the generator 1. Or, both the infusion device 161 and the generator 1 can simultaneously sense each other. Communication between the devices is achieved with a program code which is sent from one device to the other via the control/communication path 160. Alternatively, a hardwired electrical connection is made at tumor site 6.

Although synchronizing a generator and an infusion device during electrical therapy may be advantageous, other types of synchronization are also envisioned for use in another preferred embodiment. For example, numerous closed-loop approaches are available for use in electrical therapy, such as controlling therapy based on sensed parameters including oxygen levels, impedance across or within a tumor, pH levels, and internal voltages measured in electrodes employed in electrical therapy.

With regard to sensed oxygen levels, therapy may be modified based on the concentration of oxygen in and around a tumor. Oxygen may be monitored and measured with any of the devices and methods described above, such as by using optical fibers; however, any other device and method useful to quantify oxygen concentration may be used. For example, another method includes tracking DC voltage and/or current between the system electrodes (which may be made of various types of precious metal such as gold and platinum) and an implanted device housing (which may be made of a partial carbon surface, partial platinum surface, and/or a partial titanium surface) that serves as a reference point. In practice, DC voltage and/or current may be tracked in and around a tumor between a gold electrode (inserted in or around the tumor) and a device housing partially surfaced with carbon.

In the case of sensed impedance, electrical therapy may be modified based on the impedance measured across or within the tumor as a function of frequency. Impedance may be sensed by having a driver, such as the ones depicted in FIG. 22 and FIG. 23, emit a small AC current for the measurement of impedance (when electrical therapy is in DC current). Alternatively, AC current may be used to measure impedance when electrical therapy is briefly turned off. In one example, atomic oxygen in the gaseous form can be measured by impedance spectrum due to the differing frequency dependent impedances generated by various gases and fluids. Therefore, by examining impedance as a function of frequency, oxygen level may be determined. If in the case that a high level of "free" or gaseous oxygen is measured, the system may be programmed to decrease the amount of current applied. This is largely because excess gas can cause pain and/or bloating in a patient. Alternatively, in another circumstance, increased oxygen may be indicative of growing tumors as they tend to have a large oxygen supply. Sensing oxygen for this purpose will allow electrical therapy to be adjusted accordingly.

Electrical therapy may also be modified or adjusted in relation to a sensed pH. pH may be sensed with any of the devices and methods described herein above, as well as any other devices and methods useful for sensing pH. In practice, sensors may measure pH during applications of persistent, high current electrical therapy, such as, for example, during application of 5-10 V for 0.5 to 2.0 hours as described in FIGS. 27a, 27b, and 27d. The system may increase current slowly and steadily over a period of time while simultaneously measuring pH. At the point when the sensed pH is equal to a predetermined level (e.g. 2.0) the system may modify current such that the sensed pH stays at exactly 2.0 by increasing or decreasing current or, alternatively, may modify current such that the sensed pH is increased or decreased below 2.0 by increasing or decreasing current. In another embodiment, when the sensor detects a pH of 2.0, electrical therapy may quickly start applying persistent, low current electrical therapy, such as, for example, applications of 50 mV to 1 V for 4-48 hours as described in FIGS. 27a, 27b, and 27d. Current regulation may require careful PID (position, integral, derivative) controls due to time dependence of the pH on the current application history.

In another embodiment, electrical therapy may be adjusted based on internal voltages detected inside a tumor. A tumor is generally electronegative in comparison to healthy tissue. For example, tumor tissue has been described as being approximately 5 to 8 mV more electronegative than normal or healthy tissue. Therefore, implanted electrodes may sense the internal tumor voltage and adjust electrical therapy accordingly. For example, if tumor voltage is more electronegative than the surrounding healthy tissue, electrical therapy may be increased (e.g. increase total coulombs delivered, current, and/or voltage). However, if tumor voltage is neutral or positive in comparison to healthy tissue, then electrical therapy may be reduced or halted locally or globally (e.g. decrease total coulombs delivered, current, and/or voltage).

Figure 34:
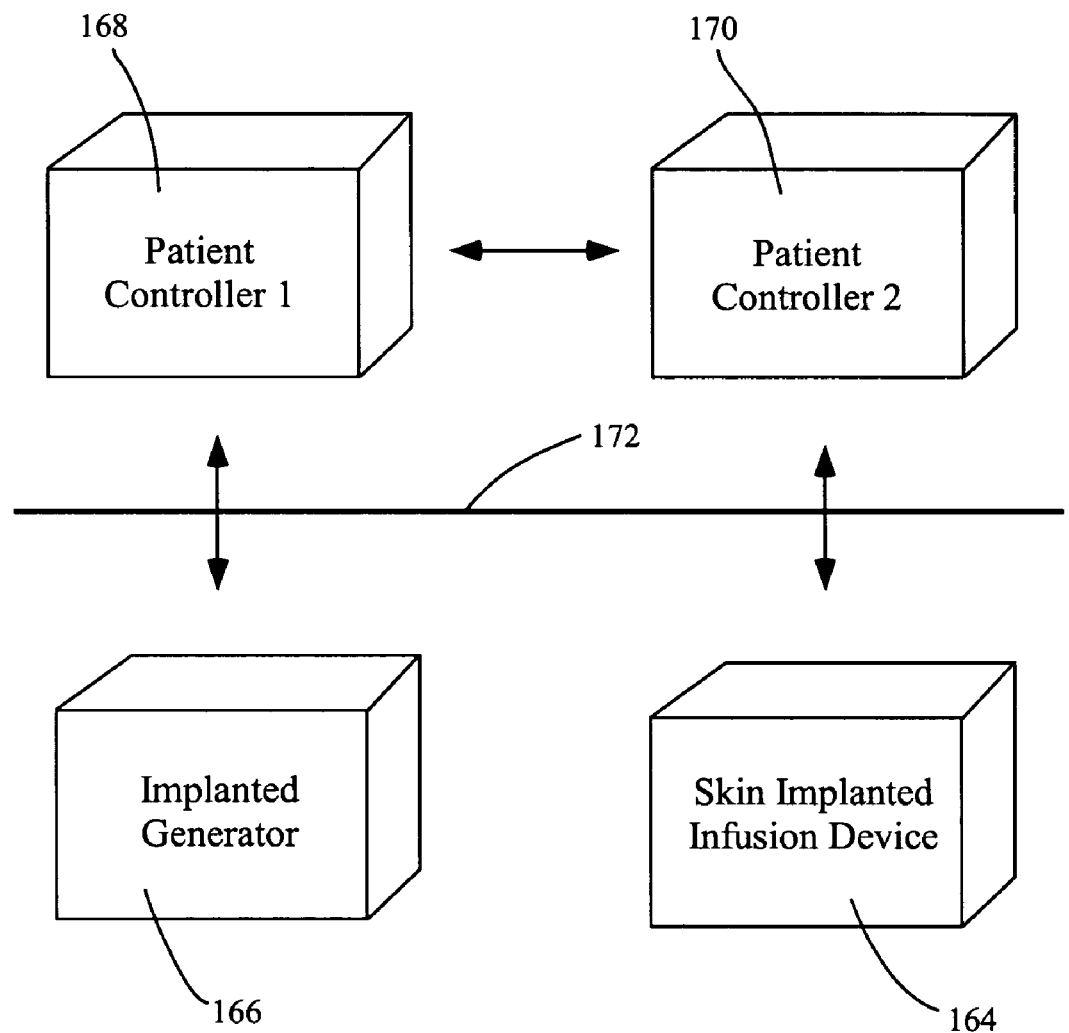
FIG. 34 is a diagram representing an exemplary method of passive synchronization which may be employed with an electrical therapy system.

A method of passive synchronization is depicted in FIG. 34. Passive synchronization can be achieved by cycling the infusion device 164 at regular intervals so that the implanted generator 166 can measure the first interval and then start its output prior to the start of the next interval. The passive synchronization model described in FIG. 34 is designed with external patient controllers 168 and 170, so that the infusion device 164 and implanted generator 166 can be adjusted non-invasively through the skin 172. In another embodiment, the external patient controllers 168 and 170 can be designed to communicate with one another and thus control synchronization of the infusion device 164 and implanted generator 166. In yet another embodiment, the controllers 168 and 170 can be combined into one unit. In another embodiment synchronization can also be applied in continuous or bolus mode.

Chemotherapeutic agents and other pharmaceuticals to be used in conjunction with the present embodiment can be administered variably according to circadian rhythms. As is known to those of ordinary skill in the art, efficacy and toxicity of commonly used chemotherapeutic agents correspond to the time of administration. For example, dosages capable of killing tumor cells may also kill or severely injure normal tissues. However, the susceptibility of normal tissues to powerful chemotherapeutic agents varies rhythmically depending on the circadian cycle, while tumor cells display a different time-related response. Thus, the timing of drug delivery is important for achieving therapeutic specificity. Therefore, administering chemotherapeutic agents and/or other pharmaceuticals may be advantageous because this practice maximizes dosage with minimal toxicity. Electrical therapy can also be adjusted according to the same circadian rhythm for maximum effectiveness. In a preferred embodiment, patients are treated with a consistent dosage of chemotherapeutic agent and electrical therapy on a regular schedule. As is known by those of ordinary skill in the art, these factors, consistent dosage and regular schedule, are important to the ultimate success of chemotherapy.

Turning now to FIG. 35a-35f, several catheter designs used to deliver drugs at a target site are illustrated. Shown are a fixation means 171, a catheter 172, a catheter tip 173, an electrode 174, an internal lead 175, an external lead 176, an electrode array 177, and apertures 178. Each of the catheters depicted in FIG. 35a-35f are coupled to an infusion device (not shown). The infusion device may be implanted into a patient or located externally to the patient. Additionally, the infusion device may have a single drug reservoir or multiple reservoirs for the administration of various pharmaceuticals. The infusion device (not shown) discharges a drug, or drugs, into the catheter 172. The drug, or drugs, flows through the catheter 172 to the catheter tip 173 where the drug, or drugs, is delivered to the target site. The target site may be any of a tumor, tumor periphery, a vein, an artery, a hepatic artery, and the like.

Figure 35A:
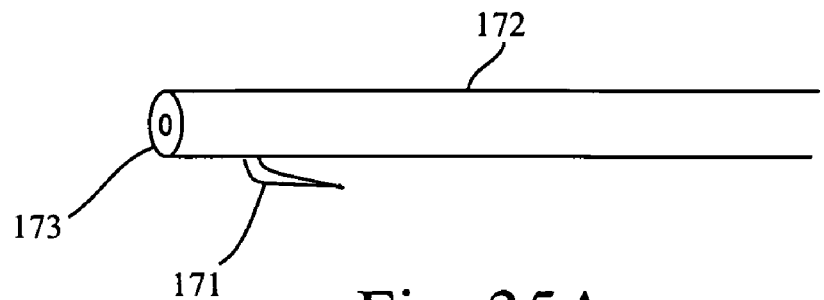
FIG. 35a-35f are illustrations depicting several examples of catheters used to infuse drugs at a target site such as may be employed with an electrical therapy system.

The catheter of FIG. 35a has a fixation means 171 coupled to the catheter tip 173 end. The fixation means 171 may be any means sufficient to directly or indirectly anchor a catheter to tissue, such as a hook, needle, suture, clamp, screw, prong, telescoping regions, and the like.

Figure 35B:
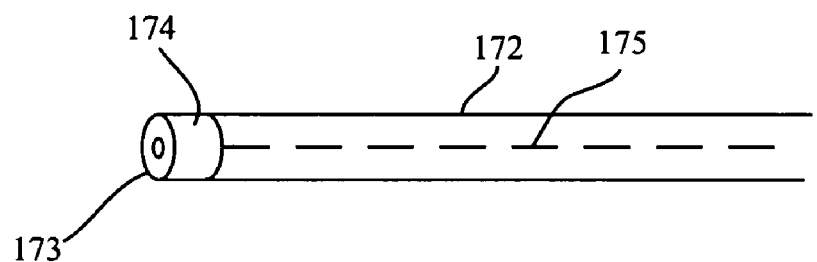

The catheter of FIG. 35b combines the electrode 174 with the catheter 172. The catheter 172 of FIG. 35b is capable of concomitantly delivering chemotherapy and electrical therapy. The electrode 174 is electrically coupled to an internal and/or external power source (not shown) via the internal lead 175; the lead 175 runs internally through the catheter 172.

Figure 35C:
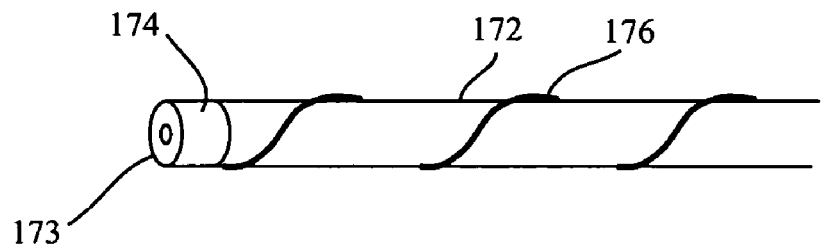

Alternatively, the electrode 174 may be electrically coupled to a power source via an external lead 176 as shown in FIG. 35c. The external lead 176 may be wrapped around the catheter 172, as shown. In another embodiment, the external lead 176 may run parallel to the catheter 172. An external lead 176 may be sufficient in cases where little mechanical stress is expected on the catheter 172 and/or lead 176 post-implant. The catheter 172 of FIG. 35c is capable of concomitantly delivering chemotherapy and electrical therapy. The electrode 174 is electrically coupled to an internal and/or external power source (not shown) via the external lead 176.

Figure 35D:
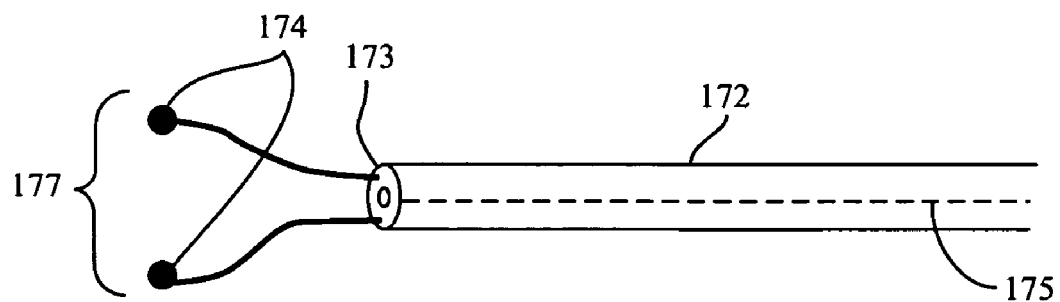

An electrode array 177 may be used in combination with a catheter 172, as shown in FIG. 35*d*. The electrode array 177 is electrically coupled to an internal and/or external power source (not shown) via an internal lead 175. However, an external lead 176, as shown in FIG. 35*c*, may also be used to couple the electrode array 177 to a power source (not shown). Although two electrodes 174 are shown in the electrode array 177 of FIG. 35*d*, any number and configuration of electrodes may be used.

Figure 35E:
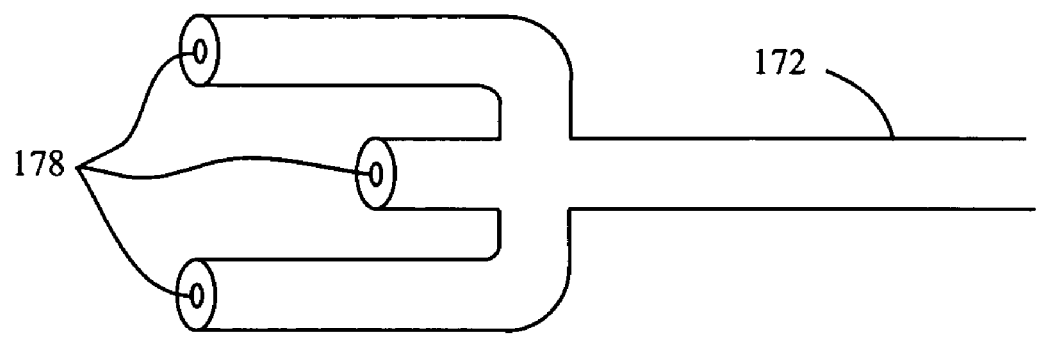
Figure 35F:
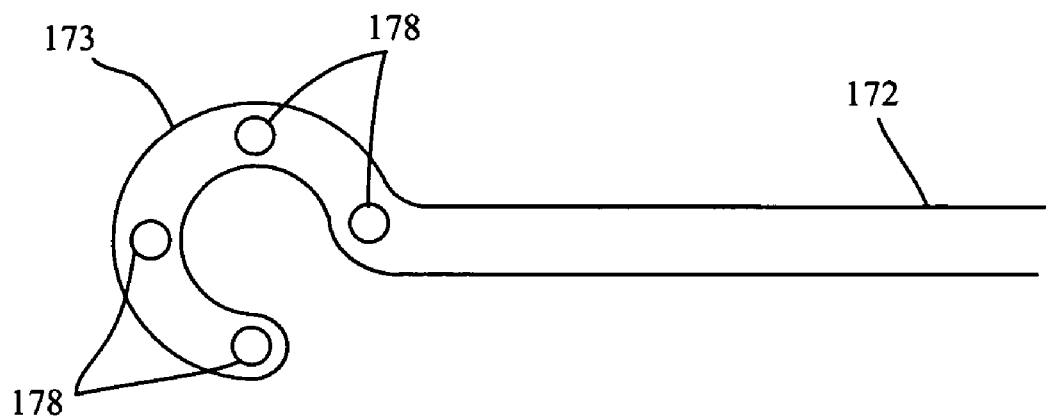

The catheter 172 of FIG. 35*e* is designed with multiple apertures 178 for access to different parts of a target site. In a preferred embodiment, the target site of FIG. 35*e* is a tumor or tumor periphery. In one embodiment, the catheter of FIG. 35*e* may be advantageously used in the tumor area to deliver varying amounts of a drug to different sites in and around the same tumor according to the size, shape, and other characteristics of the tumor. However, the branches and/or apertures 178 may be designed to provide the same, or different, amounts of drug at each site. Any number of apertures 178 and/or branches can be used. Additionally, any number of apertures 178 may be used on various shaped catheter tips 173 to deliver a drug, or drugs, such as the partial ring structure catheter tip 173 with four apertures 178 shown in FIG. 35*f*.

Any combination of the previously described variations and features may be used in combination with electrical therapy. The above should be viewed as examples of the numerous variations available and in no way limiting. The catheter of the present embodiment may be used in combination with electrodes or separate from electrodes and any number and configuration of electrodes may be used. Leads may be internal or external to the catheter. Multiple apertures and fixation means may be used interchangeably between various types of catheters.

Figure 36A:
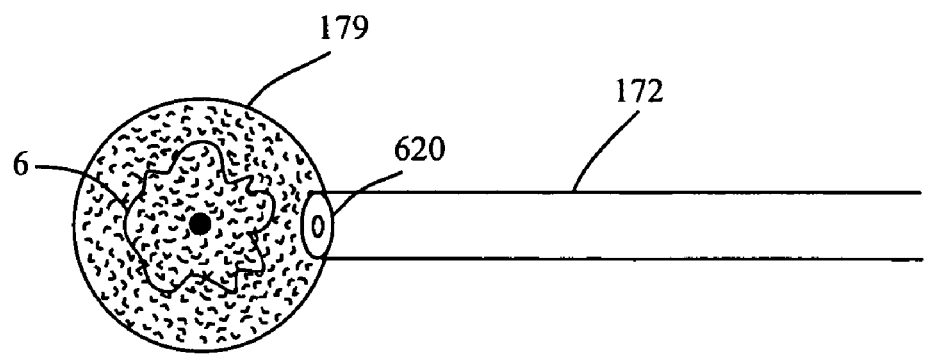
FIG. 36a-36c are illustrations depicting examples of catheters comprising porous drug-absorbing material, which can be laid out over a tumor and may be employed with an electrical therapy system.
Figure 36B:
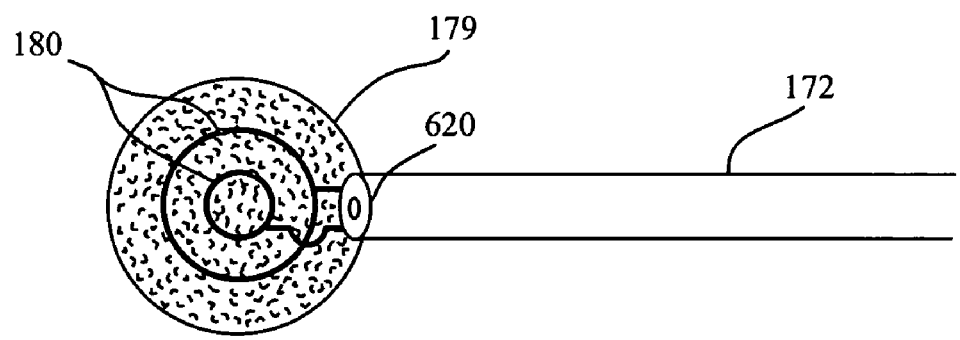
Figure 36C:
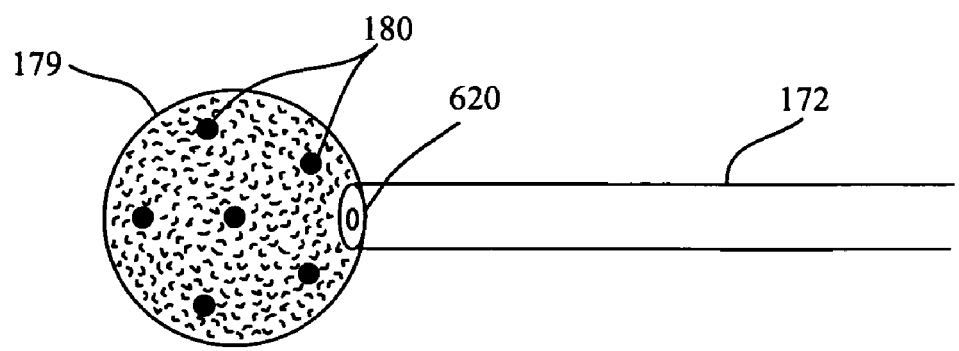

The catheter designs illustrated in FIG. 36*a*-36*c* include porous drug-absorbing material, which can be laid out over a tumor. Shown are a tumor 6, a catheter 172, porous material 179, electrodes 180, and catheter tip 620. The catheters of FIG. 36*a*-36*c* are coupled to an infusion device (not shown). The infusion device (not shown) may be implanted into a patient or located externally to the patient. Additionally, the infusion device (not shown) may have a single drug reservoir or multiple reservoirs for the administration of various pharmaceuticals. The infusion device (not shown) discharges a drug, or drugs, into the catheter 172. The drug, or drugs, flows through the catheter 172 to the catheter tip 620 where the drug, or drugs, is delivered to the porous material 179. The electrodes 180 of FIG. 36*b*-36*c* are electrically coupled to an internal and/or external power source (not shown) via a lead or leads (not shown). The lead, or leads, may be electrically coupled with any number and configuration of electrodes 180. The lead, or leads, (not shown) may be internal and/or external to the catheter.

To aid in dispersing a drug, or drugs, from the catheter 172, porous material 179 is laid over the tumor 6, as shown in FIG. 36*a*. The drug, or drugs, dispersed by the catheter 172 is partially absorbed by the porous material 179. In this manner, the tumor 6 remains in contact with the drug, or drugs, for a longer period of time. In FIG. 36*b* the porous material 179 is used in combination with electrodes 180. The electrodes 180 may be organized into concentric rings for electrical treatment, such as illustrated in FIG. 36*b*. In another embodiment, multiple point electrodes 180 may be spread on porous material 179, as shown in FIG. 36*c*.

The porous material 179 of the present embodiment may comprise any shape and size appropriate for each circumstance dependent on factors such as, but not limited to, location and size of tumor. Additionally, the porous material 179 may or may not be used in combination with electrodes 180. Electrodes 180 used in combination with the porous material 179 may comprise any number and configuration of electrodes.

Figure 37A:
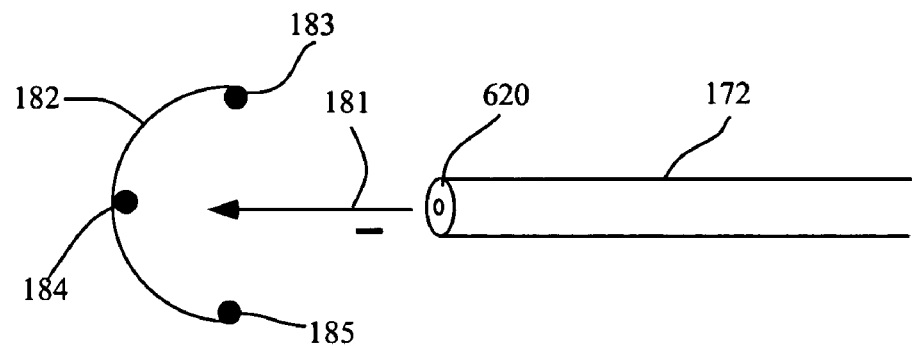
FIG. 37a-37c is a drawing illustrating an example of an electrode array that can be used to steer or spread charged drugs in electrical therapy systems.
Figure 37B:
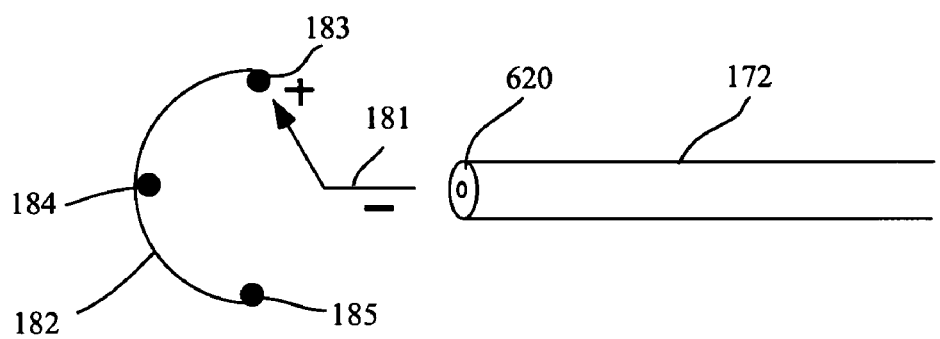
Figure 37C:
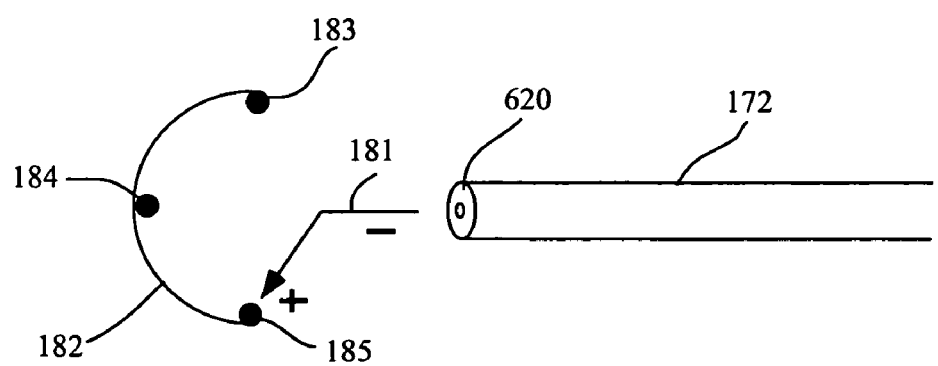

As illustrated in FIG. 37*a*-37*c*, an electrode array 182 can be used to steer or spread charged drugs, which are provided by a catheter 172. Shown are the catheter 172; a negatively charged drug 181; the electrode array 182; individual electrodes 183, 184, and 185; and a catheter tip 620. In each of FIG. 37*a*-37*c* the catheters 172 are coupled to an infusion device (not shown). The infusion device (not shown) may have a single drug reservoir or multiple reservoirs for the administration of various pharmaceuticals and/or other solutions. The infusion device (not shown) may be implanted into a patient or located externally to the patient. The infusion device (not shown) discharges a drug, or drugs, into the catheter 172. The drug, or drugs, flows through the catheter 172 to the catheter tip 620 where the drug, or drugs, is delivered to a target site. In one embodiment, the pharmaceutical is a negatively charged drug 181 or a positively charged drug (not shown).

The electrodes 183, 184, and 185 of FIG. 37*a*-37*c* are electrically coupled to an internal and/or external power source (not shown) via a lead or leads (not shown). The lead, or leads (not shown), may be electrically coupled with any number and configuration of electrodes. The lead, or leads, (not shown) may be internal and/or external to the catheter. The electrodes 183, 184, and 185 may be of either polarity, i.e. anode or cathode. Additionally, electrodes 183, 184 and 185 may switch polarities as previously described hereinabove. In one embodiment, the generator 1 may switch the polarities of electrodes 183, 184 and 185 via internal circuitry such as described in FIG. 2*e*-2*f* hereinabove. Moreover, the generator 1 may additionally serve as the anode or cathode, in place of, or in addition to electrodes 183, 184 and 185. The electrodes 183, 184 and 185 may be located inside or peripheral to the tumor 6. Furthermore, any combination of unipolar, multipolar, electrode arrays, and/or any other variation and configuration available for use with electrical therapy is contemplated by the inventors for use with the present embodiment.

In FIG. 37*a* a negatively charged drug 181 flows from catheter 172 towards the center of electrode array 182, in the direction of positively charged electrode (anode) 184. However, by altering electrical output to various electrodes 183, 184, and 185 in the electrode array 182, charged drugs can be steered to a desired location. For example, in FIG. 37*b*, positively charged electrode 183 is turned on, while electrodes 184 and 185 are turned off or are turned on as cathodes. Thus, the negatively charged drug 181 is attracted to the electrode 183. Alternatively, to direct the negatively charged drug 181 in the opposite direction, positively charged electrode 185 is turned on, while electrodes 183 and 184 are turned off (or are turned on as cathodes). Thus, the negatively charged drug 181 is redirected to electrode 185, as shown in FIG. 37*c*. Although the previous examples were explained in context of a negatively charged drug, it should be understood that a positively charged drug can also be directed according to altering charges in an electrode array. While the negatively charged drug will be attracted to a positively charged electrode (anode) and repelled by a negatively charged electrode (cathode), a positively charged drug will behave in the opposite fashion. That is, a positively charged drug will be attracted to a negatively charged electrode (cathode) and will be repelled by a positively charged electrode (anode). Additionally, any number, arrangement, and configuration of electrodes can be used to direct charged chemotherapeutic agents and/or other charged pharmaceuticals.

Figure 38A:
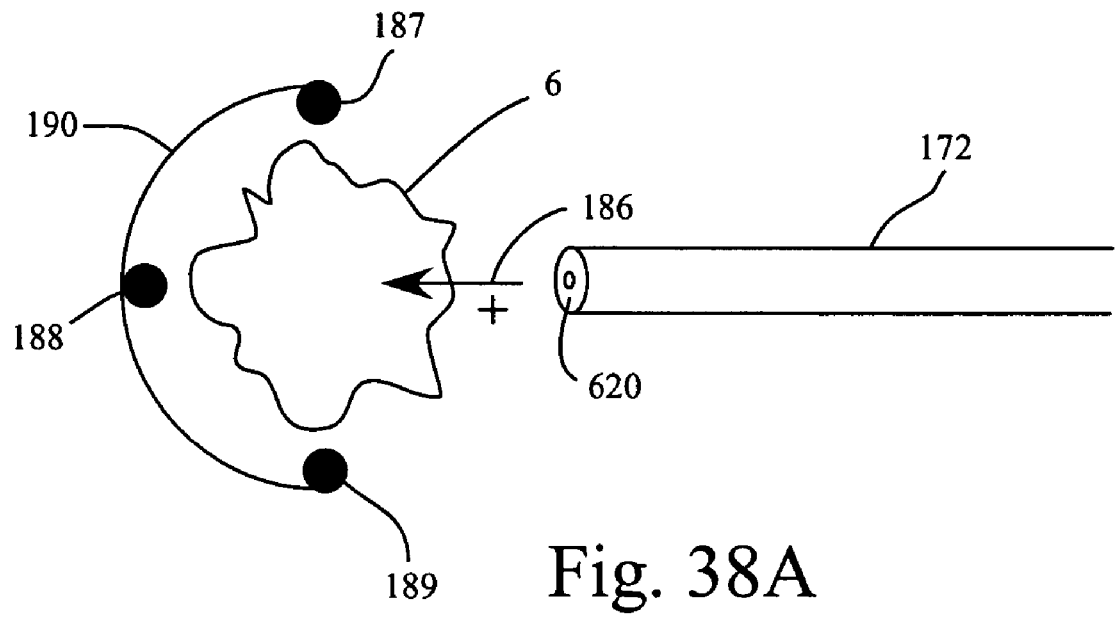
FIG. 38a-38b is a drawing depicting an application of the electrode array/catheter design of FIG. 37a-37c.
Figure 38B:
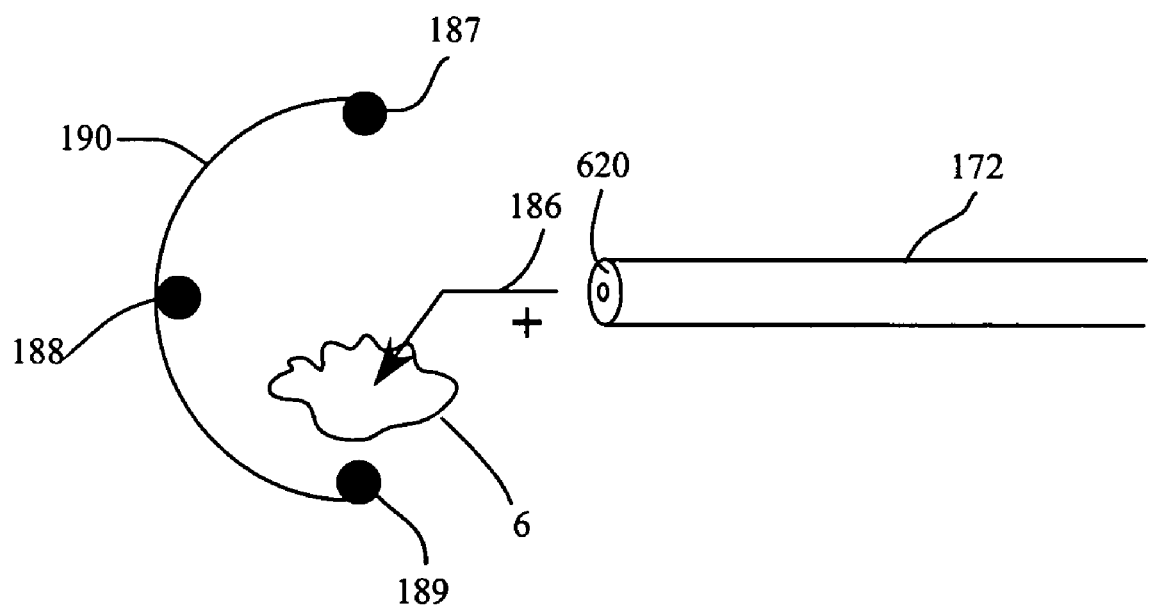

An application of the electrode array/catheter design of FIG. 37a-37c is illustrated in FIG. 38a-38b. Shown are a tumor 6; a catheter 172; a positively charged drug 186; individual electrodes 187, 188, and 189; an electrode array 190; and a catheter tip 620.

The catheter 172 is coupled to an infusion device (not shown). The infusion device (not shown) may have a single drug reservoir or multiple reservoirs for the administration of various pharmaceuticals. The infusion device (not shown) may be implanted into a patient or located externally to the patient. The infusion device (not shown) discharges a drug, or drugs, into the catheter 172. The drug, or drugs, flows through the catheter 172 to the catheter tip 620 where the drug, or drugs, is delivered to a target site. In one embodiment, the pharmaceuticals are a positively charged drug 186 or a negatively charged drug; shown in this example is a positively charged drug 186. The electrode array 190 of FIG. 38a-38b is electrically coupled to an internal and/or external power source (not shown) via a lead or leads (not shown). The lead, or leads, may be electrically coupled with any number and configuration of electrodes, although in the present embodiment the electrode array 190 is comprised of three individual electrodes 187, 188, and 189. The lead, or leads, (not shown) may be internal and/or external to the catheter.

In FIG. 38a the positively charged drug 186 initially flows from the catheter 172 to the center of the electrode array 190 where the tumor 6 is located. As therapy continues, the tumor 6 shrinks and its mass is no longer located at the center of the electrode array 190. Therefore, the negatively charged electrode (cathode) 189 is turned on and electrodes 187 and 188 are either turned off (or are turned on as anodes). Thus, the positively charged drug 186 is directed to tumor 6, which is located near electrode 189.

Detection of tumor shrinkage may be detected by sensors contemplated hereinabove. Also, the presence of the drug changes may alter tumor impedance and, therefore, electrical load on the generator. These sensed parameters can be used in locating optimum locations for drug steering. The embodiment of electrode drug steering can also be applied to drug infusion for non-cancer applications.

Figure 39:
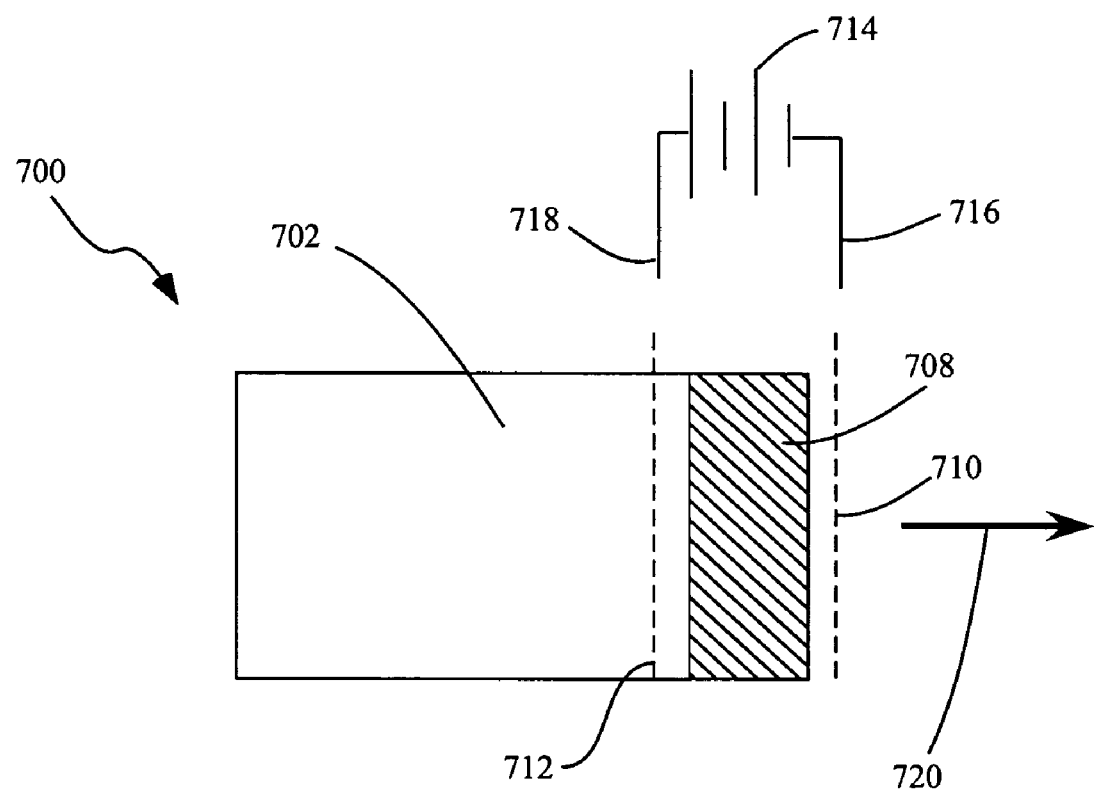
FIG. 39 (prior art) is an illustration of an example electrophoretic drug pump such as may be used with any of the catheters described in FIG. 35a-35f and FIG. 36a-36c.

Depicted in FIG. 39 is an electrophoretic drug pump 700, which is further explained in U.S. Pat. No. 4,639,244 granted to Rizk in 1987 entitled, *Implantable electrophoretic pump for ionic drugs and associated methods*, incorporated herein by reference. Shown are a reservoir 702, a membrane 708, electrodes 710 and 712, a power source 714, an anode lead 716, a cathode lead 718, and drug flow 720.

The reservoir 702 is sealed and contains a drug or drugs to be dispensed. In a preferred embodiment, the drug, or drugs, is ionic (i.e. a drug with an overall positive or negative charge). The drugs may conventionally be in the form of a suspension. The membrane 708 will permit ions to pass therethrough. However, the membrane 708 preferably resists the passage of bacteria therethrough. The membrane 708 may be a cellulose membrane. Among the preferred materials that are suitable for use as the membrane 708 are those made from cellulose esters, nylon polyvinylidene flouride, polytetrafluoroethylene, cellulose nitrate and acetate and mixtures thereof. The membrane 708 of the preferred embodiment may have pore sizes from about 0.025 to 8 microns and are from about 100 to 200 microns thick. The diameter of the membrane 708 is preferably between about 13 and 293 millimeters. In general, many types of microfiltration membranes may be employed. Among the preferred materials are those sold under the trade designations "MF" (Millipore); "Celotate" (Millipore); "Durapore" (Millipore); "Diaflow" (Amicon); "Mitex" (Millipore); and "Fluoropore" (Millipore).

The electrodes 710 and 712 may be composed of any of the materials described hereinabove and/or selected from any of the group consisting of silver/silver chloride, carbon, carbon mesh, and platinum.

Disposed on opposite sides of the membrane 708 and operatively associated therewith is a pair of porous electrodes 710 and 712. A power source 714 is coupled to the anode lead 716 and the cathode lead 718, which thereby energizes the respective electrodes 710 and 712. In this arrangement, if a negatively charged drug is contained within the reservoir 702 the membrane 708 will permit passage of the negatively charged drug through the membrane 708. The direction of drug flow 720 caused by electrophoresis with the electrodes energized as shown is indicated by the drug flow 720 arrow.

Under normal circumstances, the buildup of a concentration of ions in the reservoir 702 will result in passage of the material through the membrane 708 in the direction indicated by the arrow representing drug flow 720 even when the electrodes are not energized. This diffusion flow may be relied upon, in some instances, as establishing a basic rate for ongoing delivery of the ionic drugs. In some cases it may be desirable to provide a greater flow than would occur through diffusion in which case energizing the electrodes 710 and 712 serves to increase the rate of delivery of the material. If desired, for certain materials, means may be provided for reversing the polarity of electrodes 710 and 712 (as described hereinabove) thereby causing the electrophoresis to retard the amount of ionic flow effected through diffusion. Also contemplated is reversing the polarities of the electrodes 710 and 712 to permit diffusion of a positively charged drug. As will be appreciated by those of ordinary skill in the art, the polarities of the electrodes 710 and 712 may be either anodic or cathodic in order to allow drug flow 720 of a negatively or positively charged drug.

The electrophoretic pump of FIG. 39 is contemplated by the inventors for use with several embodiments described herein.

Figure 40:
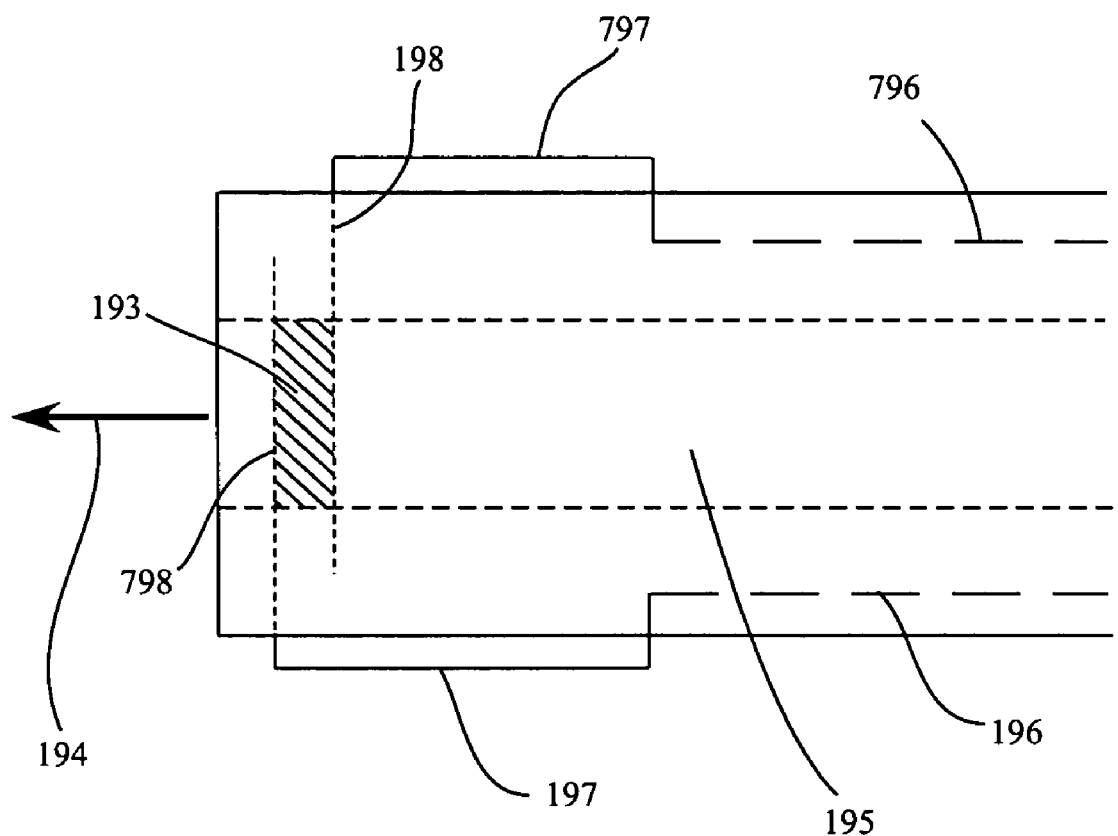
FIG. 40 is an illustration depicting an application of the electrophoretic drug pump of FIG. 39 into an electrical therapy system.

Represented in FIG. 40 is an example of an incorporation of the electrophoretic drug pump 700 of FIG. 39 into an electrical therapy and electrochemotherapy device. Shown are a reservoir 195, leads 196 and 796, electrodes 197 and 797, porous extensions 198 and 798, a membrane 193, and drug flow 194.

FIG. 40 illustrates an example of an implantable drug pump for use with electrical therapy. The electrodes 197 and 797 are electrically coupled to a power source (not shown) via leads 196 and 796. The power source (not shown) may be located internally and/or externally to a patient. The electrodes 197 and 797 may be of either polarity, i.e. anode or cathode. Additionally, electrodes 197 and 797 may switch polarities as previously described hereinabove. In one embodiment, the power source (not shown) may switch the polarities of electrodes 197 and 797 via internal circuitry such as described in FIG. 2e-2f hereinabove.

The reservoir 195 is sealed and contains a positively or negatively charged drug. The membrane may be of any of the specifications described hereinabove as well as any other useful variation.

The porous extensions 198 and 798 of electrodes 197 and 797 frame the membrane 193 periphery on opposite sides thereby permitting or retarding drug flow 194. The electrodes may be of any of the specifications described hereinabove as well as any other useful variation.

The ionic drug (that is either positively or negatively charged) will flow through the membrane 193 in the direction of the drug flow 194 arrow according to the amount of current supplied, the polarities of electrodes 197 and 797, and the charge density of the drug to be dispersed, and type of charge of the drug to be dispersed (i.e. positive, negative, or neutral).

The inventors contemplate using the same principles described herein with any other electrode configuration including the numerous configurations described hereinabove.

Figure 41A:
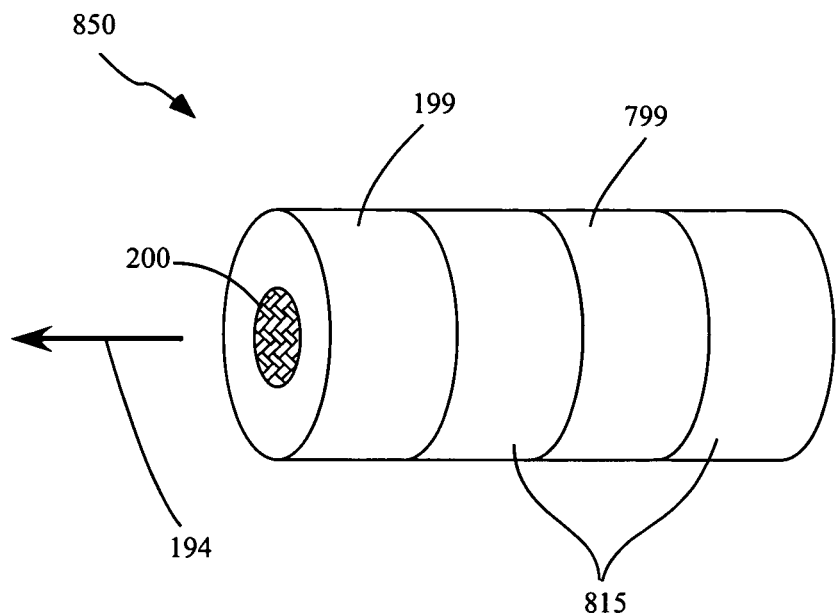
FIG. 41a-41b is an illustration representing an application of FIG. 40, whereby the electrodes are in the form of bands arranged around the circumference of a cylindrical implantable device for use in an electrical therapy system.
Figure 41B:
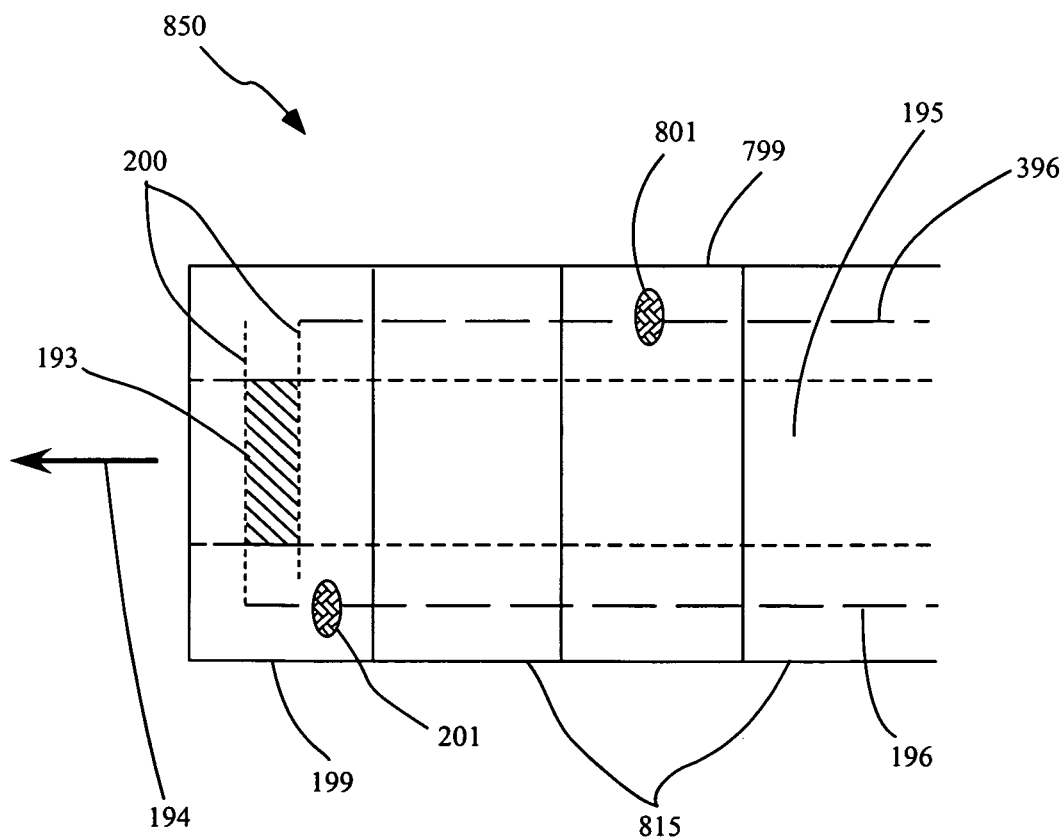

Turning now to FIG. 41a-41b, an example of a catheter 850 with an electrophoretic drug pump is described. FIG. 41a is in side view and FIG. 41b is in cross-sectional side view. Shown are a membrane 193, drug flow 194, a reservoir 195, electrodes 199 and 799, leads 196 and 396, electrode-lead contact 201 and 801, the catheter 850, polymer coated sections 815, and porous extensions 200.

Shown in FIG. 41a electrodes 199 and 799 are bands encircling the circumference of the catheter 850. Interposed between electrodes 199 and 799 are polymer coated sections 815. Both electrodes 199 and 799 may be inserted into tissue or, alternatively, only electrode 199 may be inserted into tissue. In a preferred embodiment the tissue is a tumor. Covering the end of the catheter 850 is the porous extension 200 of electrode 199 that regulates the rate of drug flow 194.

Shown in FIG. 41b the electrodes 199 and 799 are coupled to leads 196 and 396 at the electrode-lead contact 201 and 801, respectively. The electrode-lead contact 201 and 801 may be a weld or any other means sufficient to couple the electrodes 199 and 799 to the leads. The end of leads 196 and 396, opposite the electrodes 199 and 799, is coupled to a power source (not shown). The power source (not shown) may be located internally and/or externally to a patient. The electrodes 199 and 799 may be of either polarity, i.e. anode or cathode. Additionally, electrodes 199 and 799 may switch polarities as previously described hereinabove. In one embodiment, the power source (not shown) may switch the polarities of electrodes 199 and 799 via internal circuitry such as described in FIG. 2e-2f hereinabove.

The catheter contains a reservoir 195 of a drug. The reservoir 195 is sealed and contains a positively charged drug, a negatively charged drug, or a neutral drug. The membrane 193 is located behind the porous extension 200 of electrode 199. The membrane 193 may be of any of the specifications described hereinabove as well as any other useful variation. The porous extension 200 of electrode 199 regulates the rate of drug flow 194.

The liquid emitted by the infusion pumps need not necessarily be a drug. For example, an ionized solution, such as saline solution, can be introduced into a tumor via the infusion pumps as described hereinabove in order to lower the electrical impedance between electrodes and thus increase the current flow for a given applied voltage.

In the case of the present invention, electrochemical therapy may be applied using lower levels of electrical energy if an ionized solution, such as for example, a saline solution, is maintained at the tumor for the duration of the therapy, which may be months. Electrical therapy, applied briefly at wide intervals, may benefit from the increased conductivity at the time of application of the pulses via the use of less electrical energy and possibly less patient discomfort, if there is any. The ionized solution may be stored in liquid form in an implanted pump, such as described hereinabove, and delivered via catheters or needle electrodes in the manner described hereinabove for drugs, either continuously or intermittently depending upon the desired therapy. Alternatively, a solid ionized substance, such as for example, sodium chloride, may be introduced into the tumor environment and dissolved in the water and other fluids present in the tumor prior to and during the therapy.

Figure 42A:
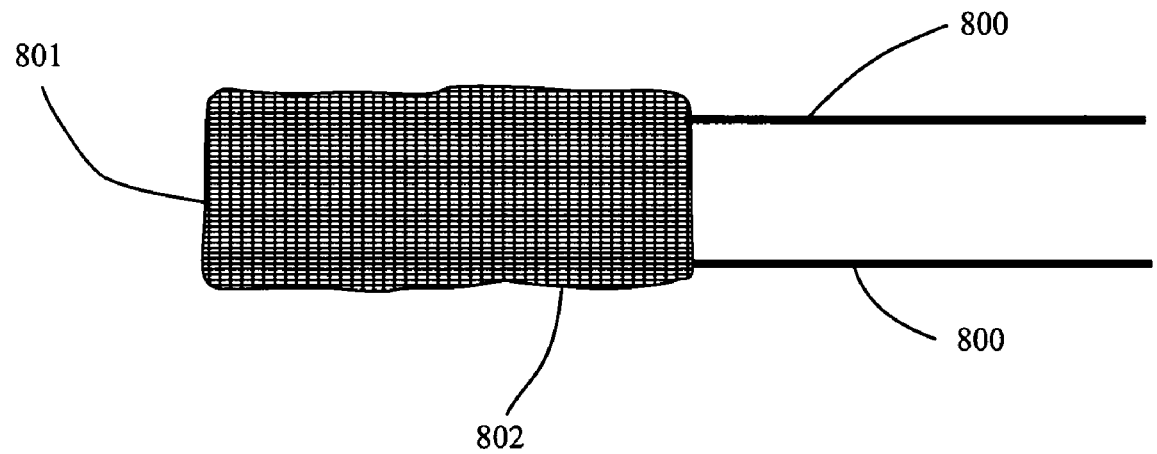
FIG. 42a-42b is an illustration of a device for infusing a solid ionized substance for increased conductivity and reduced impedance in a tumor for use in an electrical therapy system.
Figure 42B:
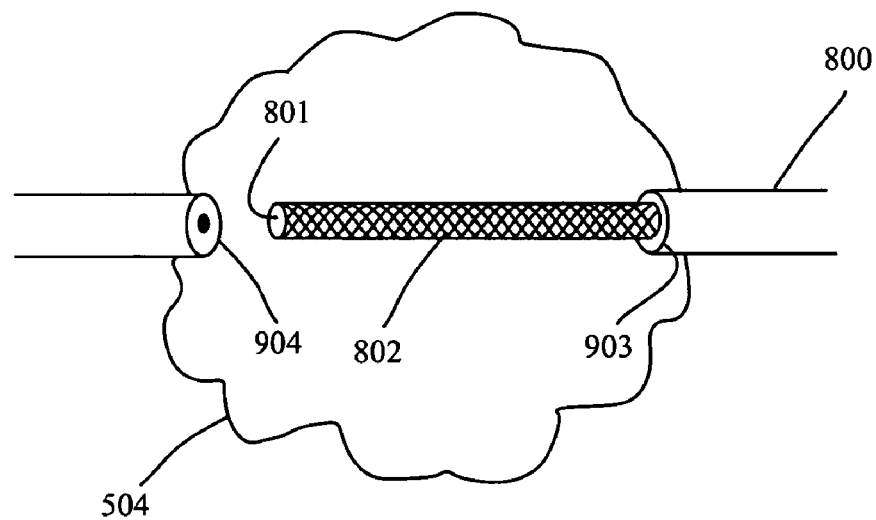

Shown in FIG. 42a-42b is a device for infusing a solid ionized substance, such as sodium chloride (NaCl) for increased conductivity and reduced impedance in a tumor. Shown are a tumor 504, a lead and/or electrode 800, a tip 801, solid ionized substance 802, lead and/or catheter outlets 903 and 904. Turning to FIG. 42a, the tip 801 of a lead or electrode 800 is coated with solid ionized substance 802. When the tip 801 is placed in an aqueous tumor environment, the solid ionized substance 802 slowly dissolves to maintain a higher electrical conductivity in the area. The tip 801 may be designed to assure that all of the solid ionized substance 802 will not be dissolved for months. This may be accomplished by mixing in or coating the solid ionized substance 802 with an agent that inhibits dissolving. In another embodiment, the density of the solid ionized substance 802 may be increased to retard dissolving.

Turning now to FIG. 42b a device and method useful to direct the ionized substance 802 to the center of the tumor 504 is depicted. The tip 801 is extended beyond electrode and/or drug infusion outlets 903 and 904 which are placed in the tumor 504 periphery. Therefore, the solid ionized substance 802, separated electrically from the electrode and/or drug infusion outlets 903 and 904 will dissolve in the center of the tumor 504 between the electrode and/or drug infusion outlets 903 and 904. This will effectively increase the conductivity along the current path through the tumor 504. Alternatively, tip 801 may be supplied with orifices for infusing ionized substance through a catheter.

Figure 43:
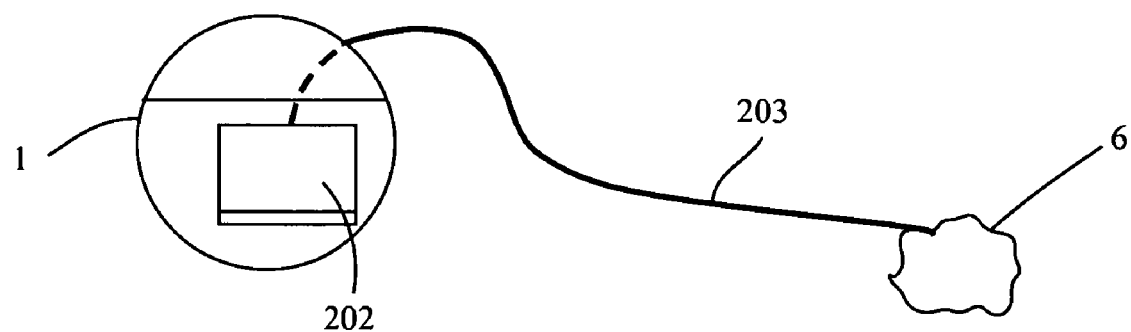
FIG. 43 is an illustration depicting an example of a device for treatment of tumors with an optical fiber such as may be employed in an electrical therapy system.

Shown in FIG. 43 is a device for using electrical therapy on tumors with an optical fiber. Shown are a generator 1, a tumor 6, a light source 202, and an optical fiber 203. The light source 202 is housed in the generator 1. The light source 202 is coupled to the optical fiber 203. The generator 1 powers the light source 202, such that light is transmitted to the tumor 6 by way of the optical fiber 203.

The light transmitted to the tumor 6 from light source 202 may activate a photosensitive drug. For example, a photosensitive cytotoxic drug can be administered to the tumor 6 by any means, including, but not limited to, an injection and any of the catheters described herein. Then, at the tumor 6, where light is provided by the light source 202 via the optical fiber 203, the photosensitive cytotoxic drug is activated; thereby, destroying cancerous cells while preserving healthy cells.

Importantly, it is not necessary for the light source 202 to be housed inside generator 1. That is, the light source 202 may be located externally to the generator 1.

An apparatus and method for treating a neoplasm with an optical fiber pipe is described in U.S. Pat. No. 6,021,347 entitled, Electrochemical treatment of malignant tumors, granted to E. Herbst et al, on Feb. 1, 2000, which is incorporated herein by reference. However, Herbst does not describe using an optic fiber in conjunction with an implantable device or electrical therapy as is described herein.

Figure 44:
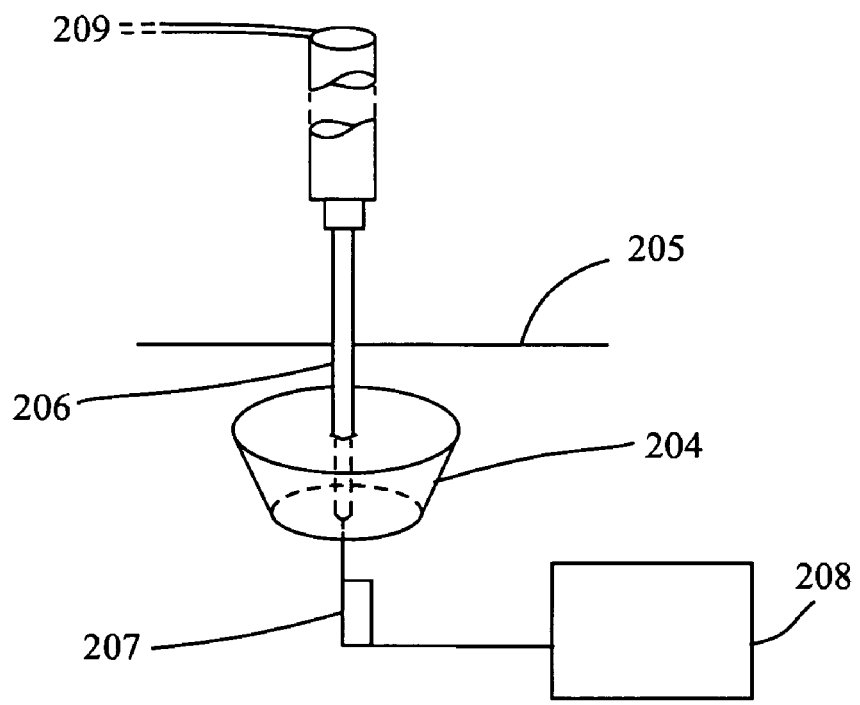
FIG. 44 is side-view illustration depicting an example of a generator useful for providing power to a light source that activates photosensitive drugs in an electrical therapy system.

The device of FIG. 44 represents a cross-sectional side view of a connection means useful for providing power to a light source, which may activate photosensitive drugs. Shown are a port 204, skin 205, a conducting needle 206, a needle contact 207, a light source 208, and a connection to a power supply 209.

The connection to a power supply 209 is coupled to a power source (not shown). In a preferred embodiment, the power source (not shown) is an external generator. The port 204 is implanted subcutaneously, below the skin 205 layer. The port 204 is electrically coupled to the light source 208. When a conducting needle 206 is inserted into the port 204 and contacts the needle contact 207 an electrical connection is made between power supply connection 209 and the light source 208, thereby powering light source 208. The powered light source 208 is then capable of delivering light to a tumor. Light may be delivered to a tumor by way of an optical fiber, or any other means useful for transmitting light.

This system of powering a light source through an external source may be advantageous in certain circumstances because light requires a lot of energy. This device may conserve an internal power supply. Additionally, if photosensitive drugs are cytotoxic to all cells, including healthy cells, close control should be maintained over the light source which may be accomplished via an external power supply.

The implantable device may be used in conjunction with radiation and chemotherapy. By employing electrical therapy over a long period of time it helps kill some malignant cells that have developed resistance to radiation and/or to anticancer drugs. The implant can be used to aid in gene transfer therapy and electroimmunotherapy as well as in conjunction with vasoconstriction drugs. The implantable device can be used with hyperthermia therapy, ultrasonics, and magnetotherapy as well.

In the case of radiation therapy and/or brachytherapy, the electrodes of the present embodiment can be adjusted to enhance the effects of radiation therapy and/or brachytherapy. At certain points in electrical therapy, especially in those cases involved with conjunctive radiation therapy and/or brachytherapy, all electrodes may be forced anodal, thereby generating molecular oxygen. By increasing the concentration of molecular oxygen, tissue will be more sensitive to radiation therapy and/or brachytherapy. Additionally, electrical therapy may be administered until an appropriate oxygen level to enhance radiation therapy is achieved. The system may detect oxygen level via various methods and sensors described herein. Once the appropriate oxygen level is reached, the system may notify a medical practitioner through a telemetry link to begin radiation therapy.

In another embodiment, tumor cells may be oxygenated with certain oxygenating products such as nitromidazoles (e.g. nimorazole), perfluorocarbons (PFC's) (e.g. Oxyfluor, Oxygent), hypoxic cytotoxins (e.g. tirapazamine, porfiromycin), and RSR13, which is an allosteric inhibitor of hemoglobin. These, or other radiosensitizing/tissue oxygenating substances may be infused via a drug pump such as any of the devices described hereinabove, and/or any other useful device for delivering a radiosensitive/tissue oxygenating substance to a tumor site.

Because the electrodes may be placed entirely in a tumor, as previously described, the cancerous tissue, as opposed to healthy tissue, will be subjected to increased sensitivity to radiation therapy and/or brachytherapy by any of the methods described hereinabove.

As is known in the art, brachytherapy is a type of radiation therapy that involves the placement of radioactive sources either in tumors or near tumors. In this treatment approach, radiation from the radioactive sources is emitted outward and is limited to short distances. Thus, unlike external beam radiotherapy, where radiation must traverse normal tissue in order to reach the tumor, brachytherapy is much more localized and therefore reduces radiation exposure to normal tissue while allowing a higher radiation dose as compared to external beam radiotherapy. Electrical therapy, as previously discussed, may be used in conjunction with placement of radioactive sources as is performed in brachytherapy.

In one example, a radioactive source, such as any of cobalt-60, iodine-125, iodine-131, iridium-192, strontium-89 (metastron), and samarium-153, may be placed on the skin of a patient near a tumor site or in a patient as a radiation seed. As is known by those of ordinary skill in the art, radioactive substances may be placed directly in the tissue or organ afflicted with cancer. For example, radiation seeds may be placed directly in the prostate of those individuals afflicted with prostate cancer.

Electrical therapy may be used in conjunction with hyperthermia therapy wherein the temperature of living tissue is increased for therapeutic purposes. Hyperthermia treatments have for many years been used for treatment of cancers. It is known that raising of the temperature of cells to above about 43 degrees Celsius to 45 degrees Celsius for a sufficient amount of time causes necrosis, and temperatures below about 41.5 degrees Celsius generally do not affect cells. Some types of malignant cells reportedly can be destroyed by raising their temperatures to levels slightly below those injurious to most normal cells. One of the techniques which has been used for hyperthermia is heating of the blood of a patient by an external apparatus, thereby raising the temperature of the entire body or a portion thereof to the therapeutic temperature. This procedure risks substantial injury to the patient if temperature is not carefully controlled, and may fail to raise the temperature of the malignant cells sufficiently for destruction. Any malignant cells which remain undestroyed may cause a recurrence of the tumor. Therefore, the electrical therapy device as described herein may be used to increase temperature of cancerous tissue. Any configuration of leads and electrodes may be used to innervate cancerous tissue. By strategically placing any number and configuration of leads and electrodes in and around cancerous tissue, only cancerous tissue is affected and thus safety in hyperthermia treatment is increased.

6. Corrosion

In situations where current or voltage is relatively large and/or the duration of the therapy is extended, there may be electrochemical degradation (i.e. corrosion) of electrodes over a period of time. However, preventive measures may be taken to lessen any potential corrosion. For example, periodic reversals in polarity of electrodes used in electrical therapy are useful to prevent corrosion. Additionally, periodic reversals in DC polarity or pulse polarity in electrochemotherapy are useful to prevent corrosion. Furthermore, the implantable device may be configured to be more resistant to corrosion by, for example, including redundant electrodes and utilizing multiple electrode segments.

Figure 45:
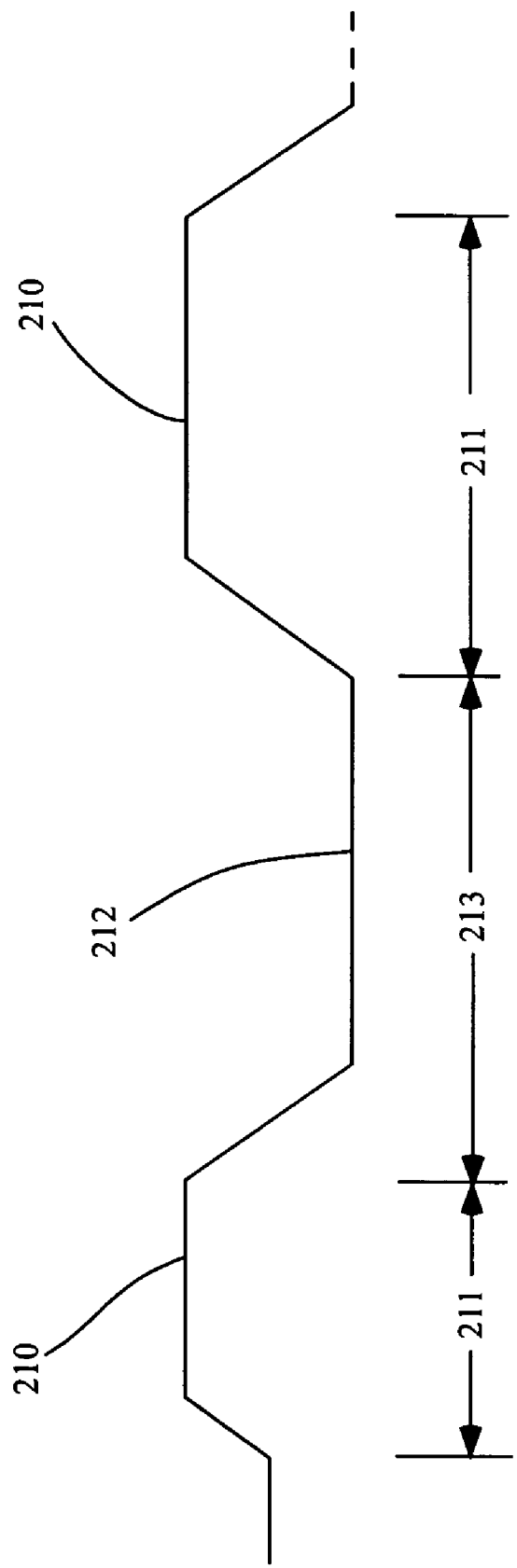
FIG. 45 is a graph depicting examples of time-varying characteristics of an electrical pulse for use in an electrical therapy system.

Referring to FIG. 45, shown are time-varying characteristics of an electrical pulse used for the purpose of electrical therapy produced by a generator. The abscissa in FIG. 45 represents time, such that a point nearer to the ordinate is less time and a point further away from the ordinate is more time. The ordinate in FIG. 45 represents pulse amplitude, such that a point nearer to the abscissa is a negative amplitude pulse and a point further away from the abscissa is a positive pulse amplitude.

Shown are positive amplitude portions of the pulse 210, time span of positive amplitude portion of the pulse 211, negative amplitude portion of the pulse 212, and time span of negative amplitude portion of the pulse 213.

The generator may be designed so that after a time span of positive amplitude pulse 211, the positive amplitude portion of the pulse 210 switches to the negative amplitude portion of the pulse 212. After a time span of negative amplitude pulse 213, the negative amplitude portion of the pulse 212 switches back to the positive amplitude portion of the pulse 210, and this pattern repeats indefinitely. The time span of the positive amplitude portion of the pulse 211, and time span of negative amplitude portion of the pulse 213 may or may not be equal in length. Additionally, the time span of positive amplitude portion of the pulse 211, and time span of negative amplitude portion of the pulse 213 may be on the order of minutes to weeks in length.

Figure 46:
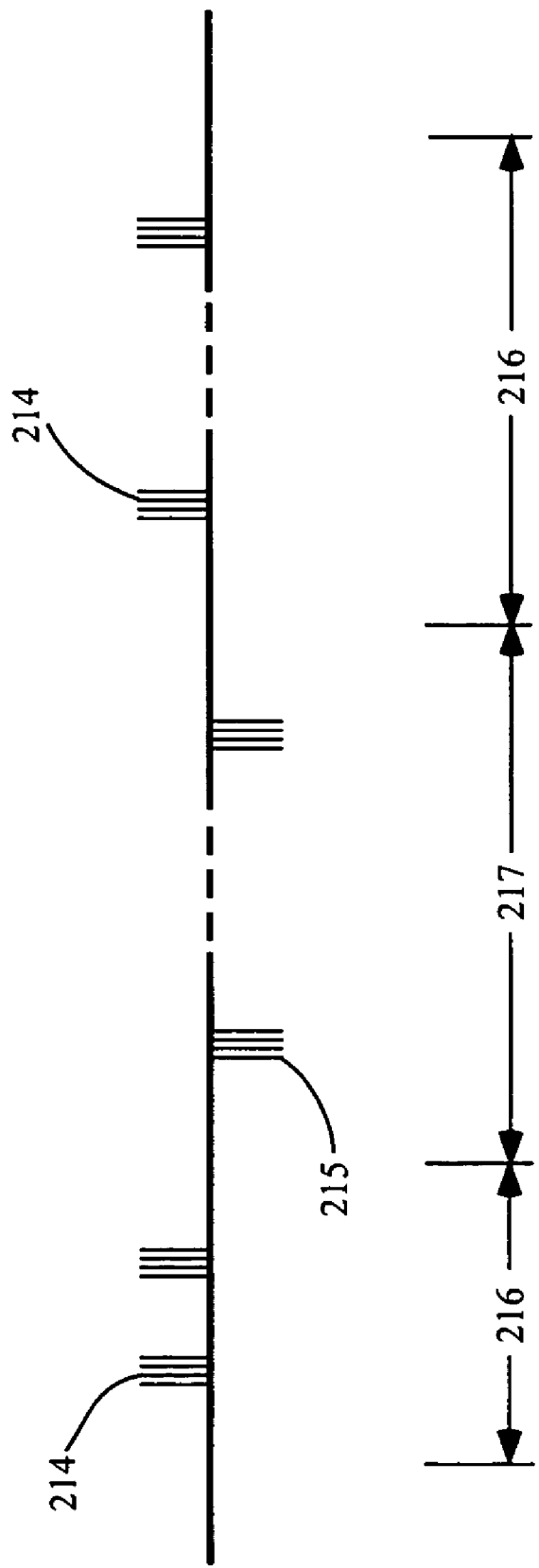
FIG. 46 is a graph representing an exemplary method for use with an electrical therapy system.

FIG. 46 illustrates a method of preventing corrosion for use in electrical therapy. Positive polarity pulse sequences 214 are switched to negative polarity pulse sequences 215 at the end of time interval 216. Negative polarity pulse sequences 215 continue for the duration of time interval 217. Following time interval 217, negative polarity pulse sequences 215 may be switched back to positive polarity pulse sequences 214, as shown in FIG. 46. Time intervals 216 and 217 may be for any length of time and are not necessarily equal.

Figure 47A:
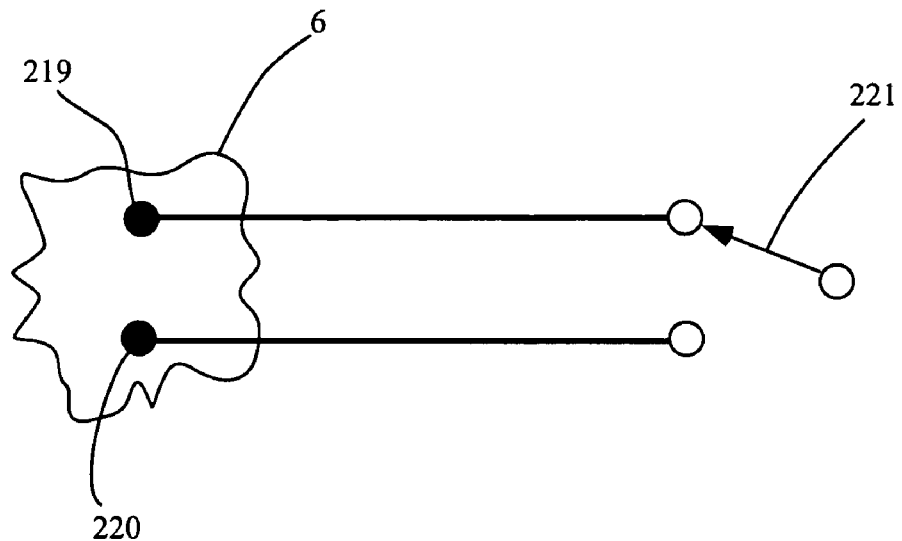
FIG. 47a-47b is a drawing showing examples of redundant electrodes used to prevent adverse effects of corrosion in electrical therapy.
Figure 47B:
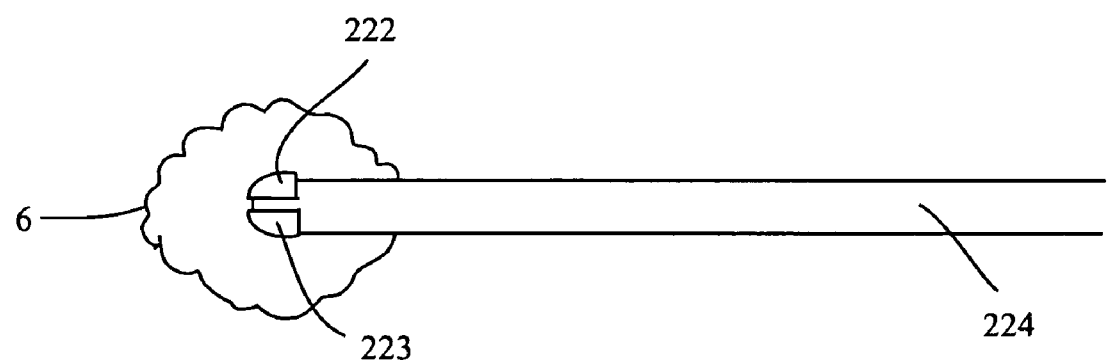

In another embodiment, redundant electrodes can be used as is shown in FIG. 47a-47b to prevent the adverse effects of corrosion. Shown are tumor 6, redundant electrodes 219 and 220, switch 221, electrode segments 222 and 223, and lead 224. In FIG. 47a redundant electrodes 219 and 220 are shown inserted into tumor 6. Electrode 219 may be used in the circuit for a period of time (typically months) and then electrode 220 is used in the place of electrode 219 for a second period of time. Switch 221 is used to switch current between electrodes 219 and 220. Any number or type of electrodes may be used in the present embodiment. In another embodiment sensing the effects of corrosion may automatically cause switching from one corroding electrode to the next uncorroded electrode. The electrodes may be located on separate leads, as shown in FIG. 47a, or on the same lead, as shown in FIG. 47b. Lead 224 is inserted in tumor 6 and has two electrode segments 222 and 223.

7. External Device

As described herein, the preferred embodiment may be used in conjunction with a power source and controlling unit located internally or externally to a patient. In certain circumstances usage of the external version of the preferred embodiment may be advantageous. An external power source and controlling unit may be coupled physically and/or telemetrically to an internal counterpart comprising any combination of lead or leads, electrode or electrodes, internal generator or generators, catheter or catheters, port or ports, drug reservoir or drug reservoirs and any other option, feature, and configuration described previously.

Figure 48:
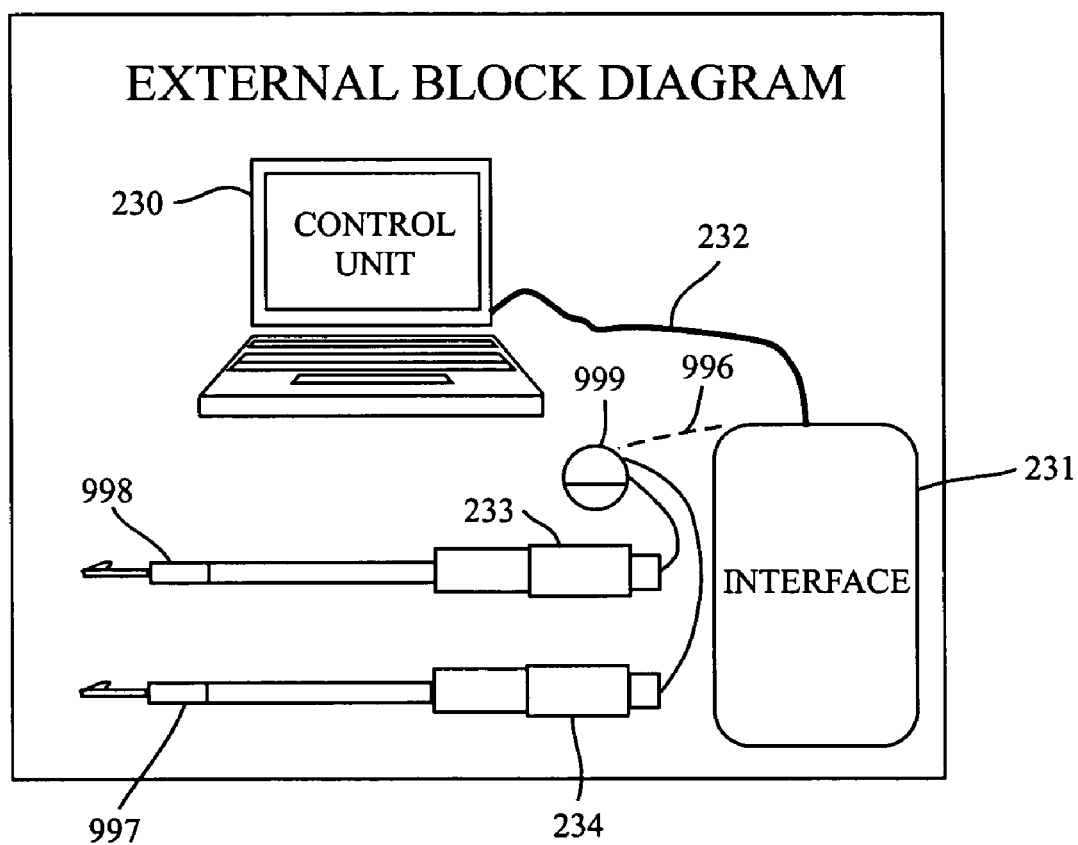
FIG. 48 is an illustration representing an example of a basic form of an external device for use with electrical therapy.

A basic form of the external device is illustrated in FIG. 48. Shown are control unit 230, interface wand 231, coupling means 232, leads 233 and 234, electrodes 998 and 997, radio frequency communication path 996, and can 999. Control unit 230 is coupled to interface wand 231 via coupling means 232 which may be physical and/or telemetric and includes any of a universal serial bus (USB), serial port, Personal Computer Memory Card International Association (PCM-CIA) card, and RF. Interface wand 231 is coupled to the implantable can 999 via radio frequency communication path 996, thereby allowing the electrical therapy system parameters to be reprogrammed non-invasively. The implantable can 999 is electrically coupled to leads 233 and 234, which are coupled to electrodes 998 and 997. A wide variety of options and features are available for use in each component.

The control unit may be a computer and in a preferred embodiment is a laptop computer for ease of use and portability. The control unit may comprise any number of the following programmable features: current (variable or constant), voltage (variable or constant), total charge, time of therapy, polarity selection, and pulse waveforms. Various pulse waveform parameters may be adjusted such as rate, pulsewidth, frequency, duty cycle, and rounded pulses, which may be advantageously used to increase patient comfort. The control system may also comprise a display monitor and data storage component. Any parameter measured or inputted to the device may be reflected on a display monitor and recorded in a data storage component. Any of the following parameters may be displayed and/or stored by the device: current, charge, voltage, impedance, temperature, pH, patient information and therapy record, and imaging. Imaging may be used especially in conjunction with IR or an optical lead. The storage component of the device may be a database. In a preferred embodiment, the database information may be displayed in a user friendly form such as graph, pictures, and charts. For example, the chart of FIG. 49 is an example of a user friendly data chart which can be used to display current information and input changes to the controller. Control means of the control system may include any number of buttons and levers, but may also be adapted to include a foot pedal and/or joystick control. In a preferred embodiment, a joystick control may be used to adjust current.

The interface box may be implanted or located external to a patient. In the present embodiment, the interface box is located externally to a patient. The interface box may be powered by any combination of isolated circuitry, alternating current (AC) line, and battery. The unit may also be rechargeable. Electrode outputs may number three or more. At a minimum the outputs should include 2 percutaneous leads and an external patch electrode. Additional electrode outputs or adapters may be advantageously added. For example, electrodes that have selectable current levels such as one-half nominal current or one-fourth nominal current may be used. In a preferred embodiment, these types of electrodes may be positioned at the tumor periphery to minimize necrosis of healthy tissue.

The leads and electrodes of the external system may include any combination of the features, options, and configurations previously described.

The external device may be used according to the same regimen and treatment schedule as previously described.

The control system and interface components may be completely external to the patient or they may be semi-implantable. For example, a receiving coil with rectifier and lead system may be implanted while the control system and wand are external. Alternatively, a smart semi-implantable device with inductive power transfer may be used. In a preferred embodiment the implant has a microprocessor and programming.

8. Examples

A better understanding of the present embodiment and of its many advantages may be clarified with the following examples, given by way of illustration.

Example 1

Well known for his extensive research and subsequent publications on the topic of electromedicine, Bjorn Nordenstrom of Sweden developed a theory on the nature of bio-electricity and the healing process. He treated cancer in his patients as clinical proof of his theories. His model of control systems was named "biologically closed electric circuits" (BCEC) and sought to explain structural development in tissue injury and particularly around cancers. He found that treatment of cancer with DC electrodes changes the microenvironment of the cancer cells by electrophoresis of water and fat and electro-osmosis of water. The therapy that is based on this principle is called "electrochemical treatment" (ECT). His further experimentation showed that direct current ionizes tissue (as does ionizing radiation). Ionization of tissue via direct electrodes affected normal and malignant tissue differently. Low energy levels built up the therapeutic dose of energy from the inside of the tumor.

The electrodes used by Nordenstrom were introduced through the chest wall (in the case of lung tumors) into the patient under guidance of biplane fluoroscopy or computed tomography under local anesthesia. According to Nordenstrom, the electrodes should present a large surface area but should be easily introducible without causing too much damage.

As reported by Nordenstrom in 1978 (*Preliminary clinical trials of electrophoretic ionization in the treatment of malignant tumors*. IRCS Medical Science 6: 537 (1978)), herein incorporated by reference, non-operable human lung tumors were treated with DC current. 0.2 mm thick Teflon® insulated platinum electrodes wherein the distal 20 mm were free from insulation were implanted percutaneously under local anesthesia. One electrode was placed in the tumor and one in the surrounding tissue or in a vessel supplying the tumor. Ten to 15 volt DC was then applied with the tumor electropositive. An initial current of 5 to 10 mA was then increased gradually to 30 to 40 mA producing intensive ionization. The electropositive tumor tissue turned into a dry gangrene surrounded by diapedetic bleeding, thrombosis, and intensive leukocyte attraction. The tissue around the electronegative electrode became edematous by field induced electroosmosis and some minor tissue destruction and mainly vascular contractions. A gradual decrease in size occurred in the 6 treated tumors at monthly observations.

In addition to the above article, Nordenstrom has other publications of interest including *Biologically closed electric circuits: Activation of vascular interstitial closed electric circuits for treatment of inoperable cancers*. Journal of Bioelectricity 3: 137-153 (1984); *Biologically Closed Electric Circuits: Clinical, Experimental and Theoretical Evidence for an Additional Circulatory System*. Uppsala: Almqvist & Wiksell. (1983); *Electrochemical treatment of cancer I: Variable response to anodic and cathodic fields*. Am. J. Clin. Oncol. 12: 530-536 (1989); *Electrochemical treatment of cancer II: Effect of electrophoretic influence on adriamycin*. Am. J. Clin. Oncol. 13: 75-88 (1990) and; *Survey of mechanisms in electrochemical treatment (ECT) of cancer*. Eur. J. Surg. Suppl. 574: 93-109 (1994), all of which are herein incorporated by reference.

Example 2

Habal and Schauble noted in their 1977 paper (*An implantable DC power unit for control of experimental tumor growth in hamsters*. Medical Instrumentation 7: 305-306 (1977)), incorporated herein by reference, that the study of electrometrics in living organisms revealed the presence of an electropotential difference between non-cancerous organs and tissue and cancerous organs and tissues. Non-cancerous organs were found to be electropositive in both healthy and tumor-bearing animals, while tumors were found to be electronegative. Human tumors from surgical specimens were also found to be more electronegative than normal tissue.

In their experiment, hamsters with cancerous tumors were treated with a current flow of $4.5 \times 10^{-9}$ A. The positive electrode was placed in the cervical region at the tumor injection site, and the negative electrode was positioned on the dorsum of the hamsters. There was a marked decrease in tumor volume and the number of metastases in the experimental group over the positive control group.

In conclusion, the authors hypothesize that a change in the bioelectric milieu from relative electronegativity to relative electropositivity affects tumor growth.

Example 3

Xin et al. published the results of treatment of 386 patients with middle and late-stage lung cancer in *Electrochemical treatment of lung cancer*. Bioelectromagnetics 18:8-13 (1997), herein incorporated by reference. According to the therapeutic regimen, cancerous tumors were treated with a voltage of 6-8 V, a current of 80-100 mA, and an electric charge of 100 coulombs per cm of tumor diameter via anode and cathode platinum electrodes which were inserted transcutaneously or intraoperatively into the tumor mass. Generally, anodes were placed in the tumor center and cathodes in the tumor periphery less than 2 cm from the tumor boundary in order to protect the normal (non-cancerous) tissue from electrical damage, edema, and chemical changes produced by the reaction near the cathodes. The short term effective rate was 72% (278 cases) and the 5 year survival rate was 29.5%.

The authors comment that the effect of ECT with lower current (40-60 mA) and longer duration (2-2.5 hours) is better than that of ECT with higher current (100-150 mA) and shorter duration (1-1.5 hours). Generally, the authors found that 4 V and 20 mA are the minimal limit for ECT. Experimental results showed that about 100 coulombs per 1 cm of diameter of tumor tissue are needed for cytotoxicity. Cicatricial tumor tissue, which has fewer electrolytes, was found to need more electricity. Alternatively, squamous cell carcinomas, which contain more electrolytes than cicatricial tumor tissue, needed a lower amount of electricity. Additionally, the authors comment that based on their experimentation, placing both anodes and cathodes into tumors with anodes in the center and cathodes on the periphery works to protect normal (non-cancerous) tissue and enhances the therapeutic effect. The authors also found that the cytotoxic diameter around each electrode is about 3 cm. Thus, the distance between electrodes should not exceed 3 cm and the number of electrodes should be determined based on the tumor size and shape.

Other relevant articles by Xin et al. include *Effectiveness of electrochemical therapy in the treatment of lung cancers of middle and late stage*. Chinese Medical Journal 110: 379-383 (1997) and *Organization and spread of electrochemical therapy (ECT) in China*. Eur. J. Surg. Suppl. 577:25-30 (1994), which are herein incorporated by reference.

Example 4

In a paper by Li et al. results of ECT on dog liver were reported (*Effects of direct current on dog liver: Possible mechanisms for tumor electrochemical treatment*. Bioelectromagnetics 18:2-7 (1997)). Mechanisms of tumor electrochemical treatment (ECT) were studied using normal dog liver. Five physical and chemical methods were used. Two platinum electrodes were inserted into an anesthetized dog's liver at 3 cm separation. A voltage of 8.5 V DC at an average current of 30 mA was applied for 69 minutes; total charge was 124 coulombs. Concentrations of selected ions near the anode and cathode were measured. The concentrations of $Na^+$ and $K^+$ ions were higher around the cathode, whereas the concentration of $Cl^-$ ions was higher around the anode. Water contents and pH were determined near the anode and cathode at the midpoint between the two electrodes and in an untreated area away from the electrodes. Hydration occurred around the cathode, and dehydration occurred around the anode. The pH values were 2.1 near the anode and 12.9 near the cathode. Spectrophotometric scans of the liver sample extract were obtained, and the released gases were identified by gas chromatography as chlorine at the anode and hydrogen at the cathode. These results indicate that a series of electrochemical reactions take place during ECT. The cell metabolism and its environment are severely disturbed. Both normal and tumor cells are rapidly and completely destroyed in this altered environment. In conclusion, the authors hypothesize that the above reactions are the ECT mechanisms responsible for treating tumors.

Example 5

In a paper by Orlowski et al. (*Transient electropermeabilization of cells in culture: Increase of the cytotoxicity of anticancer drugs. Biochemical Pharmacology* 37:4727-4733 (1988)), herein incorporated by reference, effectiveness of anticancer drugs was tested in conjunction with electroporation. According to Orlowski, electropermeabilization (EPN) of living cells allows the uptake of non-permeant molecules and can reveal the drugs' potential activity on cells without the constraints of the plasma membrane crossing. In their experiment they compared the cytotoxicity of some anticancer drugs on elecropermeabilized (EP) and non-permeabilized (NEP) cultured DC-3F cells exposed to the drugs for a short time. After EPN, the increase in cytotoxicity varied between 1 and more than 700 times, depending on the usual cell uptake pathway of a given drug. The most relevant increase of toxicity was observed with molecules such as netropsin (200-fold) and bleomycin (700-fold) which in ordinary conditions weakly diffuse through the plasma membrane. Only a 3-5 fold increase of cytotoxicity was observed with lipophilic drugs able to rapidly diffuse through the plasma membrane (actinomycin D, NMHE) both in the case of drug-sensitive and resistant cell strains. This increased toxicity is clearly related to a facilitated uptake because, after electropermeabilization, the effects of melphalan (a drug which enters intact cells via leucine transporters) are not modulated by the external leucine concentration. In conclusion, the authors propose that uptake of anti-cancer and other cytotoxic drugs can be modified by EPN.

All references cited herein are incorporated by reference.

What is claimed is:

1. A method of treating abnormal tissue growth, comprising:
    implanting a first electrode at the site of the abnormal tissue growth;
    implanting a generator that functions as a second electrode at a position at least about 5 cm away from the abnormal tissue growth from the abnormal tissue growth;
    administering a therapeutic agent having an electrical charge near the second electrode;
    applying a first form of electrical therapy at a voltage of between about 3V to 5V between the first and second electrodes in which the second electrode is provided with a polarity similar to the charge of the therapeutic agent and the first electrode is provided with a polarity dissimilar to the charge of the therapeutic agent so that the first form of electrical therapy is effective for causing said therapeutic agent to migrate through bodily tissue to the first electrode implanted at the site of the abnormal tissue growth,
    administering a second form of electrical therapy between the first and second electrodes effective for achieving electroporation of cellular membranes, said second form of electrical therapy being delivered at a voltage between about 200 V and about 1300 V;
    wherein the first form of electrical therapy is applied for a sufficient amount of time to cause a change in pH of at least about 2 at the site of the abnormal tissue growth.

2. The method of claim 1, further comprising, after applying the first form of electrical therapy, reversing the polarities of the first and second electrodes and applying about 1 V to about 2 V in reverse polarity to disperse the therapeutic agent throughout the abnormal tissue growth.

3. The method of claim 1 wherein said second form of electrical therapy causing electroporation is delivered for an amount of time ranging from 1 µs to 1 ms.

4. The method of claim 1 wherein said second form of electrical therapy causing electroporation is delivered a number of times ranging from 10 to 1000 times.

5. The method of claim 1 wherein said second form of electrical therapy causing electroporation is delivered after said first electrical therapy causing attraction of the therapeutic agent to the first electrode.

6. The method of claim 1 wherein said first and second forms of electrical therapy are applied at periods of time that do not overlap.

7. The method of claim 1 wherein said first form of electrical therapy causing attraction of said therapeutic agent to an abnormal tissue growth is delivered for an amount of time ranging from one to four hours.

8. The method of claim 1 wherein during said first form of electrical therapy said first electrode functions as an anode and said second electrode functions as a cathode.

9. The method of claim 1 wherein said therapeutic agent is any of the group consisting of bleomycin, mitoxantrone, melphalan, dactinomycin, doxorubicin, and adriamycin.

10. The method of claim 1 wherein said therapeutic agent is administered by an implantable catheter.

11. The method of claim 1 wherein said second form of electrical therapy causing electroporation is delivered at a duty cycle in the range of 50 to 70 percent.

12. The method of claim 1 wherein said electrical therapy causing attraction of said therapeutic agent to an abnormal tissue growth is delivered at a duty cycle in the range of 50 to 70 percent.

13. The method of claim 1 further comprising administering an adjuvant.

14. The method of claim 1 wherein said abnormal tissue growth is a tumor.

15. The method of claim 1 wherein said abnormal tissue growth is of a prostate.

16. The method of claim 1 wherein said abnormal tissue growth is due to hyperplasia.

17. The method of claim 1 wherein said attraction of said therapeutic agent to an abnormal tissue growth is due to dehydration at an anode and local hydration at a cathode.

18. A method of treating abnormal tissue growth, comprising:
    implanting a first electrode at the site of the abnormal tissue growth;
    implanting a second electrode at a position at least about 5 cm away from the abnormal tissue growth;
    implanting a third electrode less than 5 cm away from the abnormal tissue growth;
    administering a therapeutic agent near the second electrode;
    applying a first form of electrical therapy between the first and second electrodes so that the first electrode has a first polarity and the second electrode has a second, opposite polarity, the first form of electrical therapy effective for attracting said therapeutic agent to the first electrode implanted near the site of the abnormal tissue growth, said first form of electrical therapy being delivered at a voltage of between about 1V and about 5Vi
    administering a second form of electrical therapy between the first and third electrodes effective for achieving electroporation of cellular membranes, said second form of electrical therapy being delivered at a voltage between about 200 V and about 1300 Vi and administering a third form of electrical therapy wherein the polarities of the first and second electrodes are reversed and electrical therapy is delivered at about 1 V to about 2 V to disperse the therapeutic agent throughout the abnormal tissue growth, and administering a fourth form of electrical therapy between the first electrode and the third electrode for a sufficient amount of time to cause a change in pH of at least about 2 at the site of the abnormal tissue growth in order to cause ablation.

19. The method of claim 18 wherein said second form of electrical therapy causing electroporation is delivered for an amount of time ranging from 1 μs to 1 ms.

20. The method of claim 19 wherein said second form of electrical therapy causing electroporation is delivered a number of times ranging from 10 to 1000 times.

21. The method of claim 18 wherein said second form of electrical therapy causing electroporation is delivered after said first electrical therapy causing attraction of the therapeutic agent to the first electrode.

22. The method of claim 18 wherein said first and second forms of electrical therapy are applied at periods of time that do not overlap.

23. The method of claim 18 wherein said first form of electrical therapy causing attraction of said therapeutic agent to an abnormal tissue growth is delivered for an amount of time ranging from one to four hours, 24. The method of claim 18 wherein during said first form of electrical therapy said first electrode functions as an anode and said second electrode functions as a cathode.

25. The method of claim 18 wherein said therapeutic agent is any of the group consisting of bleomycin, mitoxantrone, melphalan, dactinomycin, doxorubicin, and adriamycin.

26. The method of claim 18 wherein said therapeutic agent is administered by an implantable catheter.

27. The method of claim 18 wherein said second form of electrical therapy causing electroporation is delivered at a duty cycle in the range of 50 to 70 percent.

28. The method of claim 18 wherein said electrical therapy causing attraction of said therapeutic agent to an abnormal tissue growth is delivered at a duty cycle in the range of 50 to 70 percent.

29. The method of claim 18 further comprising administering an adjuvant.

30. The method of claim 18 wherein said abnormal tissue growth is a tumor.

31. The method of claim 18 wherein said abnormal tissue growth is of a prostate.

32. The method of claim 18 wherein said abnormal tissue growth is due to hyperplasia.

33. A method of treating abnormal tissue growth, comprising:
    implanting a first electrode at the site of the abnormal tissue growth;
    implanting a generator that functions as a second electrode at a position at a distance from the abnormal tissue growth;
    administering a therapeutic agent having an electrical charge near the second electrode;
    applying a first form of electrical therapy at a voltage of between about 3V to 5V between the first and second electrodes in which the second electrode is provided with a polarity similar to the charge of the therapeutic agent and the first electrode is provided with a polarity dissimilar to the charge of the therapeutic agent so that the first form of electrical therapy is effective for causing said therapeutic agent to migrate through bodily tissue to the first electrode implanted at the site of the abnormal tissue growth,
    administering a second form of electrical therapy between the first and second electrodes effective for achieving electroporation of cellular membranes, said second form of electrical therapy being delivered at a voltage between about 200 V and about 1300 V;
    wherein the first form of electrical therapy is applied for a sufficient amount of time to cause a change in pH of at least about 2 at the site of the abnormal tissue growth.

34. The method of claim 33, further comprising, after applying the first form of electrical therapy, reversing the polarities of the first and second electrodes and applying about 1 V to about 2 V in reverse polarity to disperse the therapeutic agent throughout the abnormal tissue growth.

35. The method of claim 33 wherein said second form of electrical therapy causing electroporation is delivered for an amount of time ranging from 1 μs to 1 ms.

36. The method of claim 33 wherein said second form of electrical therapy causing electroporation is delivered a number of times ranging from 10 to 1000 times.

37. The method of claim 33 wherein said second form of electrical therapy causing electroporation is delivered after said first electrical therapy causing attraction of the therapeutic agent to the first electrode.

38. The method of claim 37 wherein said first and second forms of electrical therapy are applied at periods of time that do not overlap.

\* \* \* \* \*